US012623079B1

(12) United States Patent
Kyani et al.

(10) Patent No.: US 12,623,079 B1
(45) Date of Patent: May 12, 2026

(54) SYSTEMS AND METHODS FOR PROVIDING NEUROSTIMULATION THERAPY ACCORDING TO GAIT FEATURES

(71) Applicant: Advanced Neuromodulation Systems, Inc., Plano, TX (US)

(72) Inventors: Anahita Kyani, Plano, TX (US); Erika Ross, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 561 days.

(21) Appl. No.: 18/077,197

(22) Filed: Dec. 7, 2022

Related U.S. Application Data

(60) Provisional application No. 63/287,128, filed on Dec. 8, 2021.

(51) Int. Cl.
*A61N 1/36* (2006.01)

(52) U.S. Cl.
CPC ..... *A61N 1/36135* (2013.01); *A61N 1/36132* (2013.01); *A61N 1/36146* (2013.01)

(58) Field of Classification Search
CPC ............ A61N 1/36135; A61N 1/36132; A61N 1/36146
See application file for complete search history.

(56) References Cited

U.S. PATENT DOCUMENTS

| | | | |
|---|---|---|---|
| 8,224,453 B2 | 7/2012 | De Ridder | |
| 8,682,441 B2 | 3/2014 | De Ridder | |
| 9,579,457 B2 | 2/2017 | Osorio | |
| 10,251,595 B2 | 4/2019 | Heruth et al. | |
| 10,631,777 B2 | 4/2020 | Clark et al. | |
| 11,344,732 B2 | 5/2022 | Moffitt et al. | |
| 12,364,863 B2 | 7/2025 | Lin et al. | |
| 2006/0095088 A1 | 5/2006 | De Ridder | |
| 2018/0085584 A1* | 3/2018 | Thakur | .............. A61N 1/36139 |
| 2020/0152078 A1* | 5/2020 | Caban | ................. G05B 13/028 |
| 2020/0282208 A1 | 9/2020 | Parker | |
| 2020/0391031 A1 | 12/2020 | Min et al. | |
| 2020/0398062 A1 | 12/2020 | Ibarrola et al. | |
| 2020/0398063 A1 | 12/2020 | DeBates et al. | |
| 2020/0402656 A1 | 12/2020 | DeBates et al. | |
| 2020/0402674 A1 | 12/2020 | DeBates et al. | |

OTHER PUBLICATIONS

Al-Kaisy, A. et al., "Sustained Effectiveness of 10 kHz High-Frequency Spinal Cord Stimulation for Patients with Chronic, Low Back Pain: 24-Month Results of a Prospective Multicenter Study," Pain Medicine, Mar. 2014, vol. 15, No. 3, pp. 347-354.

(Continued)

*Primary Examiner* — Carl H Layno

*Assistant Examiner* — Maria Catherine Anthony

(74) *Attorney, Agent, or Firm* — Norton Rose Fulbright US LLP

(57) ABSTRACT

The present disclosure provides systems and methods for providing neurostimulation therapy according to gait features. The gait features may be analyzed to develop a patient model between gait features and optimal settings for a neurostimulation therapy using machine learning operations. The model is used to control ongoing neurostimulation therapy for the patient.

10 Claims, 41 Drawing Sheets

(56) References Cited

OTHER PUBLICATIONS

Asadzadeh, S.. et al., "A Systematic Review of EEG Source Localization Techniques and Their Applications on Diagnosis of Brain Abnormalities," Journal of Neuroscience Methods, Jun. 1, 2020, vol. 339, 21 pages.

Li, F. et al. "Tai Chi and Postural Stability in Patients with Parkinson's Disease," New England Journal of Medicine, 2012, vol. 366, pp. 511-519.

Li, Q. et al., "Tai Chi Versus Routine Exercise in Patients with Early- or Mild-Stage Parkinson's Disease: A Retrospective Cohort Analysis," Brazilian Journal of Medical and Biological Research, 2020, vol. 53, No. 2, 7 pages.

Schu, S. et al., "A Prospective, Randomized, Double-Blind, Placebo-Controlled Study to Examine the Effectiveness of Burst Spinal Cord Stimulation Patterns for the Treatment of Failed Back Surgery Syndrome," Neuromodulation, 2014, vol. 17, pp. 443-450.

Sweet, J. et al., "Paresthesia-Free High-Density Spinal Cord Stimulation for Postlaminectomy Syndrome in a Prescreened Population: A Prospective Case Series," Neuromodulation, Apr. 2016, vol. 19, No. 3, pp. 260-267.

Tass, P. A. et al., "Coordinated Reset Has Sustained Aftereffects in Parkinsonian Monkeys," Annals of Neurology, Nov. 2012, vol. 72, No. 5, pp. 816-820.

Van Den Noort, J. C. et al., "Quantification of Hand Motor Symptoms in Parkinson's Disease: A Proof-of-Principle Study Using Inertial and Force Sensors," Annals of Biomedical Engineering, Jul. 19, 2017, vol. 45, No. 10, pp. 2423-2436.

* cited by examiner

STORE PC DEVICE DATA OR IDENTIFIER(S) FOR IMD TO CONTROL FUTURE COMMUNICATIONS

310

INITIATE BONDING PROCEDURE USING MAGNET OR NEAR FIELD COMMUNICATION

302

ESTABLISH BLUETOOTH COMMUNICATION SESSION BETWEEN IMD AND PC DEVICE

304

CONDUCT AUTHENTICATION OPERATIONS

306

CONDUCT KEY EXCHANGES

308

Figure 4B:
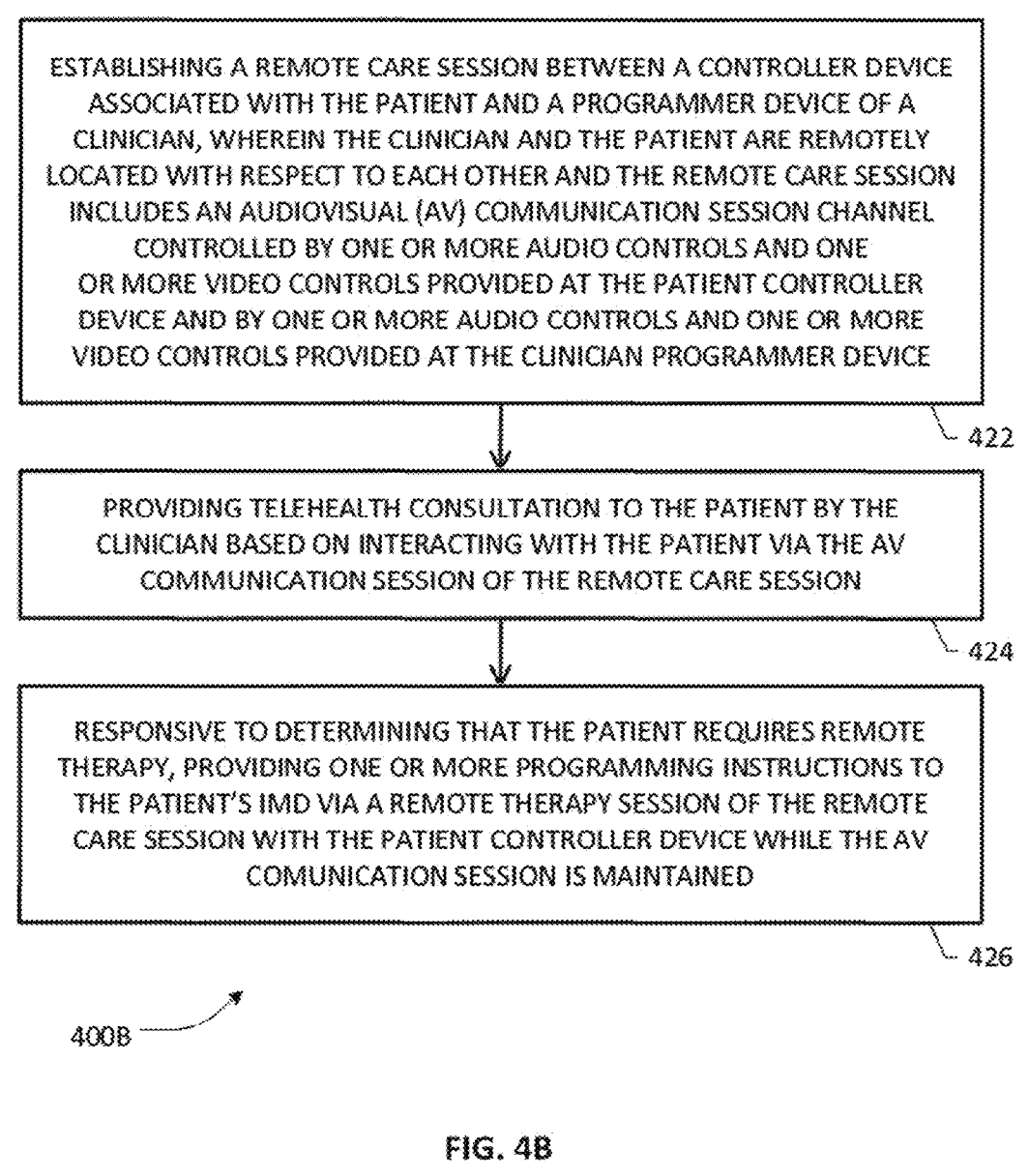

ESTABLISHING A REMOTE CARE SESSION BETWEEN A CONTROLLER DEVICE ASSOCIATED WITH THE PATIENT AND A PROGRAMMER DEVICE OF A CLINICIAN, WHEREIN THE CLINICIAN AND THE PATIENT ARE REMOTELY LOCATED WITH RESPECT TO EACH OTHER AND THE REMOTE CARE SESSION INCLUDES AN AUDIOVISUAL (AV) COMMUNICATION SESSION CHANNEL CONTROLLED BY ONE OR MORE AUDIO CONTROLS AND ONE OR MORE VIDEO CONTROLS PROVIDED AT THE PATIENT CONTROLLER DEVICE AND BY ONE OR MORE AUDIO CONTROLS AND ONE OR MORE VIDEO CONTROLS PROVIDED AT THE CLINICIAN PROGRAMMER DEVICE

⌐ 422

PROVIDING TELEHEALTH CONSULTATION TO THE PATIENT BY THE CLINICIAN BASED ON INTERACTING WITH THE PATIENT VIA THE AV COMMUNICATION SESSION OF THE REMOTE CARE SESSION

⌐ 424

RESPONSIVE TO DETERMINING THAT THE PATIENT REQUIRES REMOTE THERAPY, PROVIDING ONE OR MORE PROGRAMMING INSTRUCTIONS TO THE PATIENT'S IMD VIA A REMOTE THERAPY SESSION OF THE REMOTE CARE SESSION WITH THE PATIENT CONTROLLER DEVICE WHILE THE AV COMUNICATION SESSION IS MAINTAINED

Figure 8:
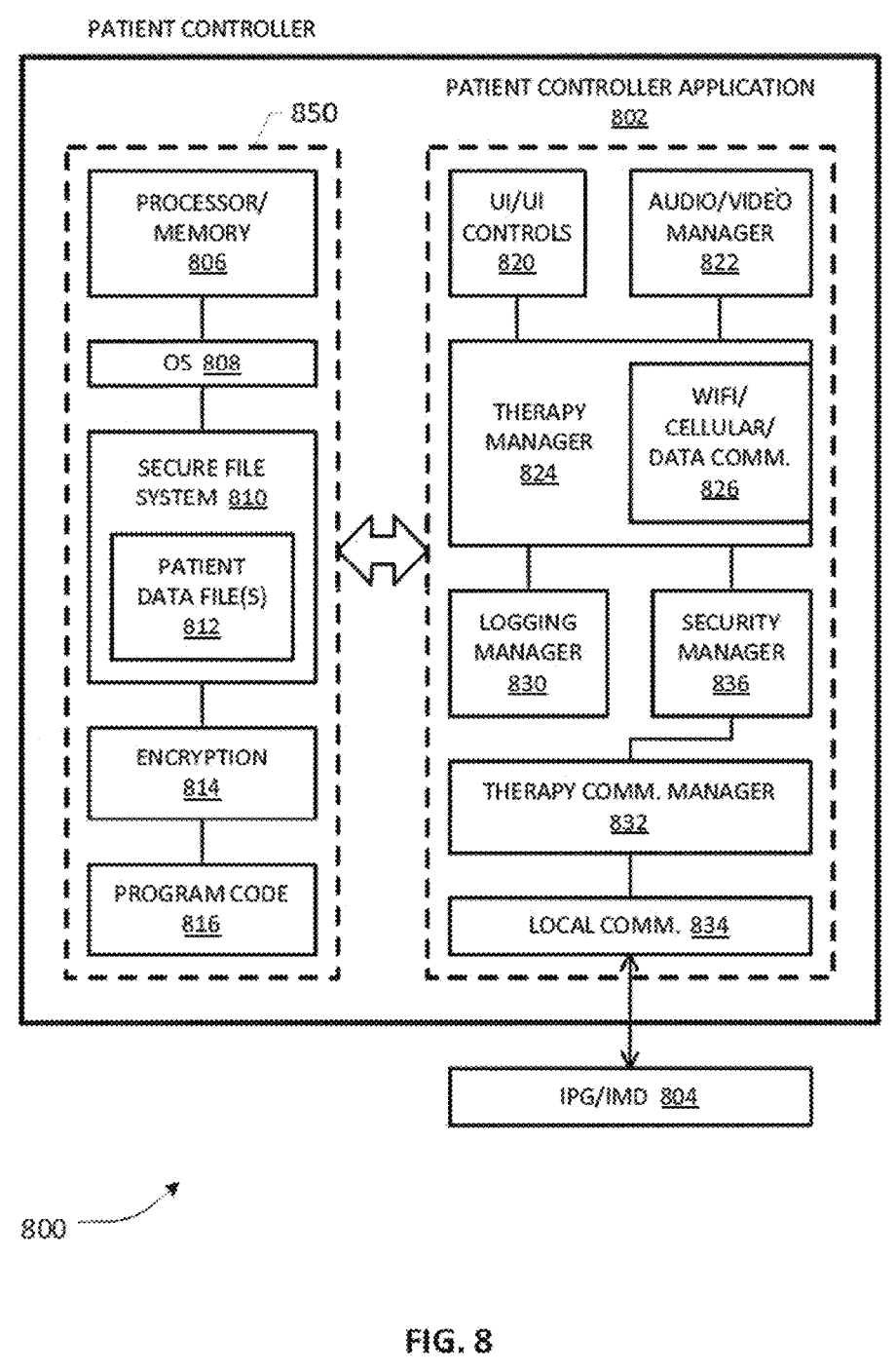

PATIENT CONTROLLER

PATIENT CONTROLLER APPLICATION
802

850

PROCESSOR/
MEMORY
806

OS 808

SECURE FILE
SYSTEM 810

PATIENT
DATA FILE(S)
812

ENCRYPTION
814

PROGRAM CODE
816

UI/UI
CONTROLS
820

AUDIO/VIDEO
MANAGER
822

THERAPY
MANAGER
824

WIFI/
CELLULAR/
DATA COMM.
826

LOGGING
MANAGER
830

SECURITY
MANAGER
836

THERAPY COMM. MANAGER
832

LOCAL COMM. 834

IPG/IMD 804

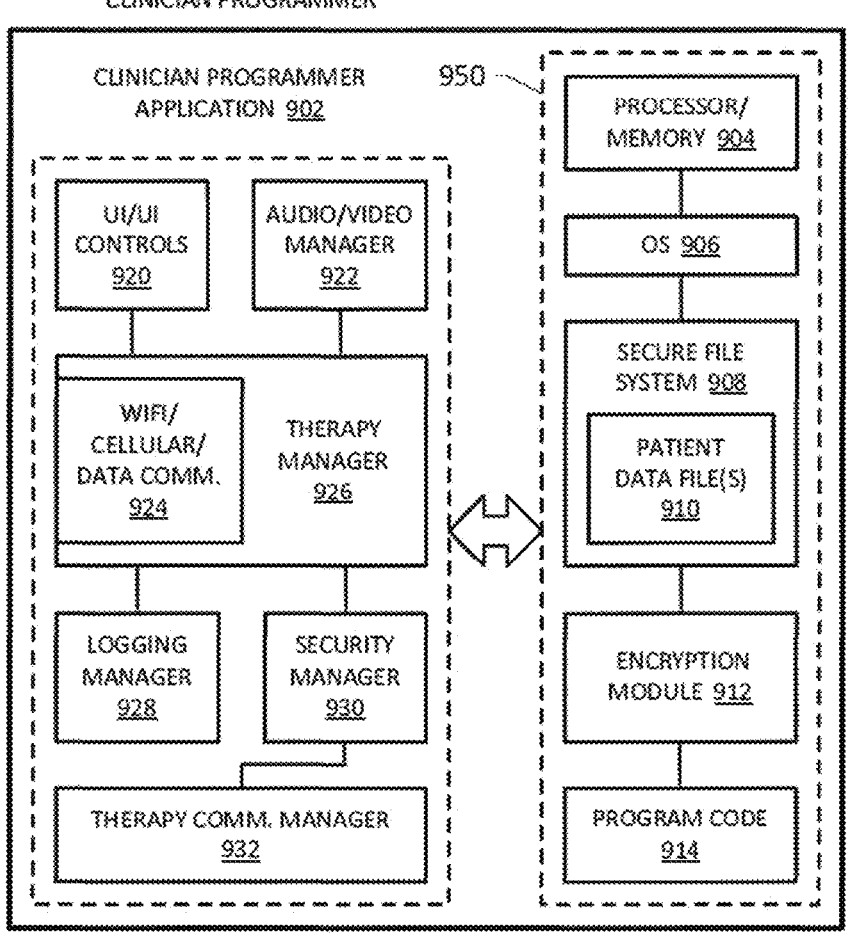
FIG. 9

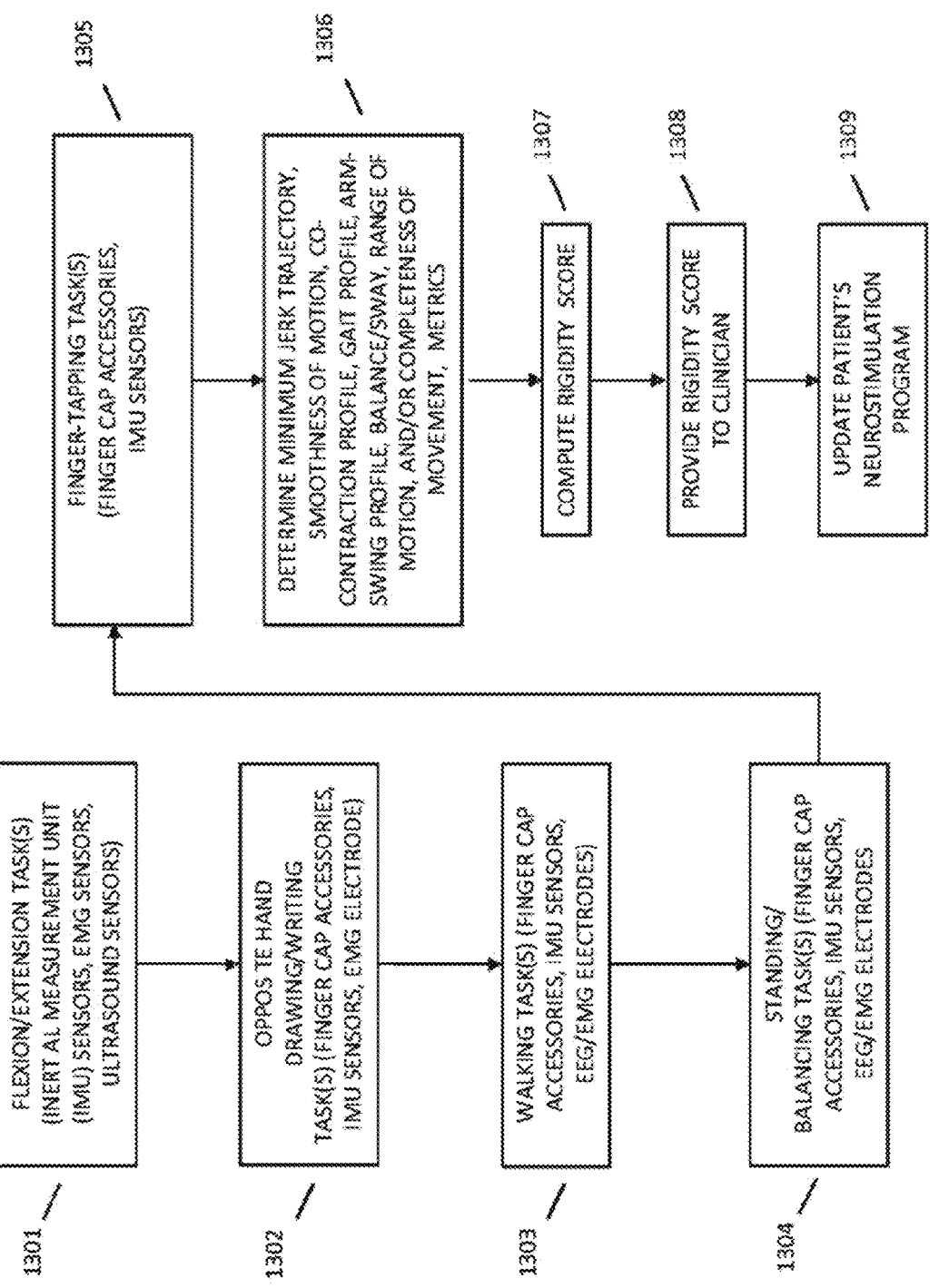

FINGER-TAPPING TASK(S) (FINGER CAP ACCESSORIES, IMU SENSORS) — 1305

DETERMINE MINIMUM JERK TRAJECTORY, SMOOTHNESS OF MOTION, CO-CONTRACTION PROFILE, GAIT PROFILE, ARM-SWING PROFILE, BALANCE/SWAY, RANGE OF MOTION, AND/OR COMPLETENESS OF MOVEMENT, METRICS — 1306

COMPUTE RIGIDITY SCORE — 1307

PROVIDE RIGIDITY SCORE TO CLINICIAN — 1308

UPDATE PATIENT'S NEUROSTIMULATION PROGRAM — 1309

FLEXION/EXTENSION TASK(S) (INERTIAL MEASUREMENT UNIT (IMU) SENSORS, EMG SENSORS, ULTRASOUND SENSORS) — 1301

OPPOSITE HAND DRAWING/WRITING TASK(S) (FINGER CAP ACCESSORIES, IMU SENSORS, EMG ELECTRODE) — 1302

WALKING TASK(S) (FINGER CAP ACCESSORIES, IMU SENSORS, EEG/EMG ELECTRODES) — 1303

STANDING/BALANCING TASK(S) (FINGER CAP ACCESSORIES, IMU SENSORS, EEG/EMG ELECTRODES) — 1304

FIG. 13

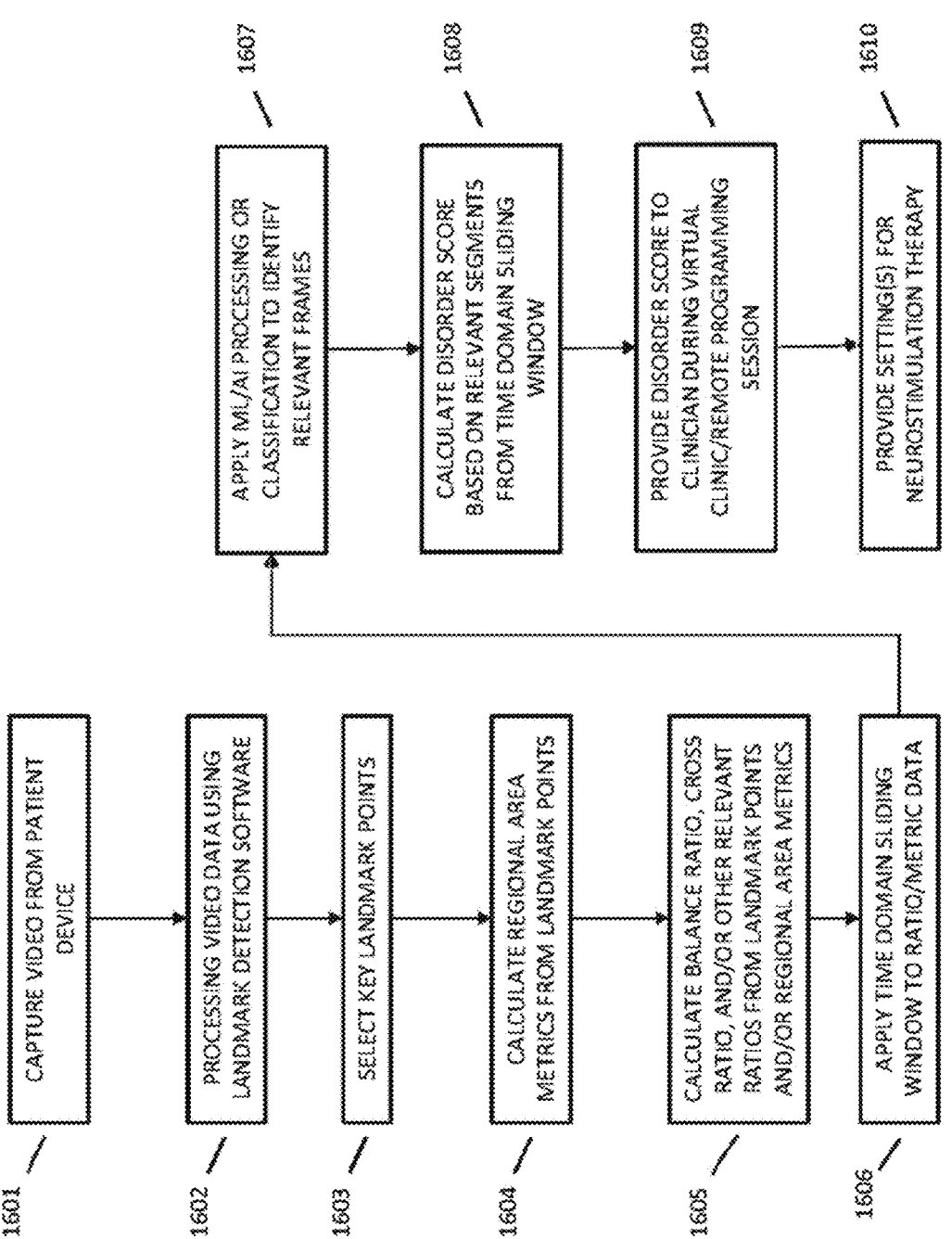

1607 APPLY ML/AI PROCESSING OR CLASSIFICATION TO IDENTIFY RELEVANT FRAMES

1608 CALCULATE DISORDER SCORE BASED ON RELEVANT SEGMENTS FROM TIME DOMAIN SLIDING WINDOW

1609 PROVIDE DISORDER SCORE TO CLINICIAN DURING VIRTUAL CLINIC/REMOTE PROGRAMMING SESSION

1610 PROVIDE SETTING(S) FOR NEUROSTIMULATION THERAPY

1601 CAPTURE VIDEO FROM PATIENT DEVICE

1602 PROCESSING VIDEO DATA USING LANDMARK DETECTION SOFTWARE

1603 SELECT KEY LANDMARK POINTS

1604 CALCULATE REGIONAL AREA METRICS FROM LANDMARK POINTS

1605 CALCULATE BALANCE RATIO, CROSS RATIO, AND/OR OTHER RELEVANT RATIOS FROM LANDMARK POINTS AND/OR REGIONAL AREA METRICS

1606 APPLY TIME DOMAIN SLIDING WINDOW TO RATIO/METRIC DATA

FIG. 16

Virtual Clinic AV Permissions

☑ Voice ☑ Video

Anonymize
Video
☑ Face ☑ Hands ☑ Arms ☑ Legs ☑ Torso
☑ Background

Anonymize
Voice
☐ Voice

START
VIRTUAL CLINIC

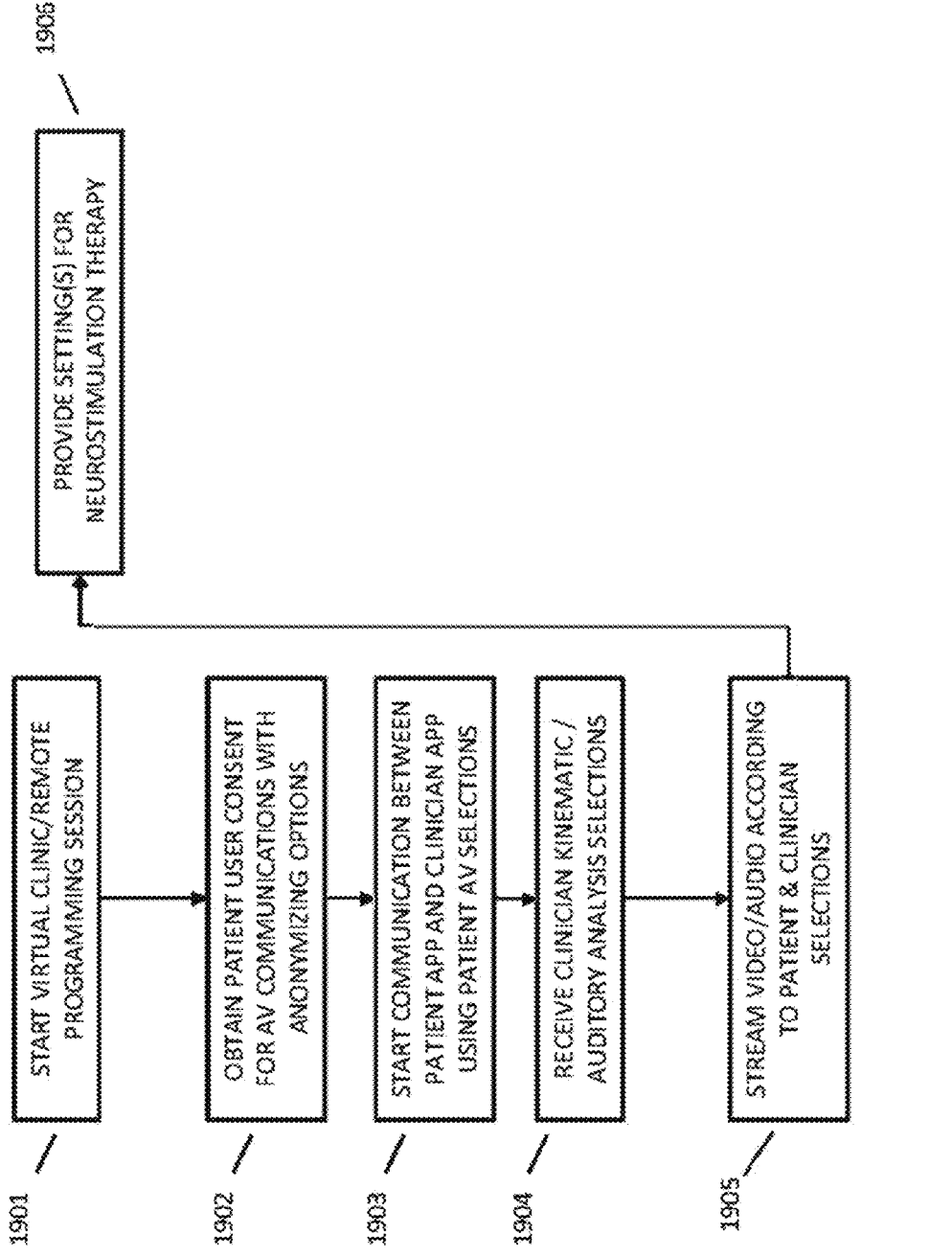

1905

PROVIDE SETTING(S) FOR NEUROSTIMULATION THERAPY

1901
START VIRTUAL CLINIC/REMOTE PROGRAMMING SESSION

1902
OBTAIN PATIENT USER CONSENT FOR AV COMMUNICATIONS WITH ANONYMIZING OPTIONS

1903
START COMMUNICATION BETWEEN PATIENT APP AND CLINICIAN APP USING PATIENT AV SELECTIONS

1904
RECEIVE CLINICIAN KINEMATIC / AUDITORY ANALYSIS SELECTIONS

1905
STREAM VIDEO/AUDIO ACCORDING TO PATIENT & CLINICIAN SELECTIONS

FIG. 19

| | Sleep spindles | K-complexes | Delta wave | Theta wave | Alpha wave | Beta wave |
|---|---|---|---|---|---|---|
| Stage 1 | 0% | 0% | 10% | 60% | 20% | 10% |
| Stage 2 | 40% | 40% | 5% | 5% | 5% | 5% |
| Stage 3 | 20% | 0% | 60% | 10% | 5% | 5% |
| Stage 4 | 0% | 0% | 70% | 10% | 10% | 10% |
| REM | 0% | 0% | 10% | 10% | 20% | 60% |

SYSTEMS AND METHODS FOR PROVIDING NEUROSTIMULATION THERAPY ACCORDING TO GAIT FEATURES

CROSS-REFERENCE TO RELATED APPLICATION(S)

The present application claims the benefit of priority from U.S. Provisional Patent Application No. 63/287,128, entitled SYSTEMS AND METHODS FOR PROVIDING NEURO-STIMULATION THERAPY ACCORDING TO GAIT FEATURES and filed Dec. 8, 2021, the content of which is incorporated herein by reference in its entirety.

TECHNICAL FIELD

The present application is generally directed to providing digital health services to patients.

BACKGROUND

Implantable medical devices have changed how medical care is provided to patients having a variety of chronic illnesses and disorders. For example, implantable cardiac devices improve cardiac function in patients with heart disease by improving quality of life and reducing mortality rates. Respective types of implantable neurostimulators provide a reduction in pain for chronic pain patients and reduce motor difficulties in patients with Parkinson's disease and other movement disorders. A variety of other medical devices are proposed and are in development to treat other disorders in a wide range of patients.

Many implantable medical devices and other personal medical devices are programmed by a physician or other clinician to optimize the therapy provided by a respective device to an individual patient. Typically, the programming occurs using short-range communication links (e.g., inductive wireless telemetry) in an in-person or in-clinic setting. Since such communications typically require close immediate contact, there is only an extremely small likelihood of a third-party establishing a communication session with the patient's implanted device without the patient's knowledge.

Remote patient care is a healthcare delivery method that aims to use technology to provide patient health outside of a traditional clinical setting (e.g., in a doctor's office or a patient's home). It is widely expected that remote patient care may increase access to care and decrease healthcare delivery costs.

SUMMARY

The present application is generally directed to providing a neurostimulation therapy according to gait features of the patient.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

FIGS. 4A and 4B depicts flowcharts illustrative of a remote care scenario involving an example digital health network architecture wherein an integrated remote care session may be established between a patient and a clinician operating respective controller devices for purposes of some embodiments of the present disclosure;

FIG. 8 depicts a block diagram illustrating additional details of a patient controller device operative in a digital health network architecture for purposes of some embodiments of the present disclosure;

FIG. 9 depicts a block diagram illustrating additional details of a clinician programmer device operative in a digital health network architecture for purposes of some embodiments of the present disclosure;

US 12,623,079 B1

Figure 12:
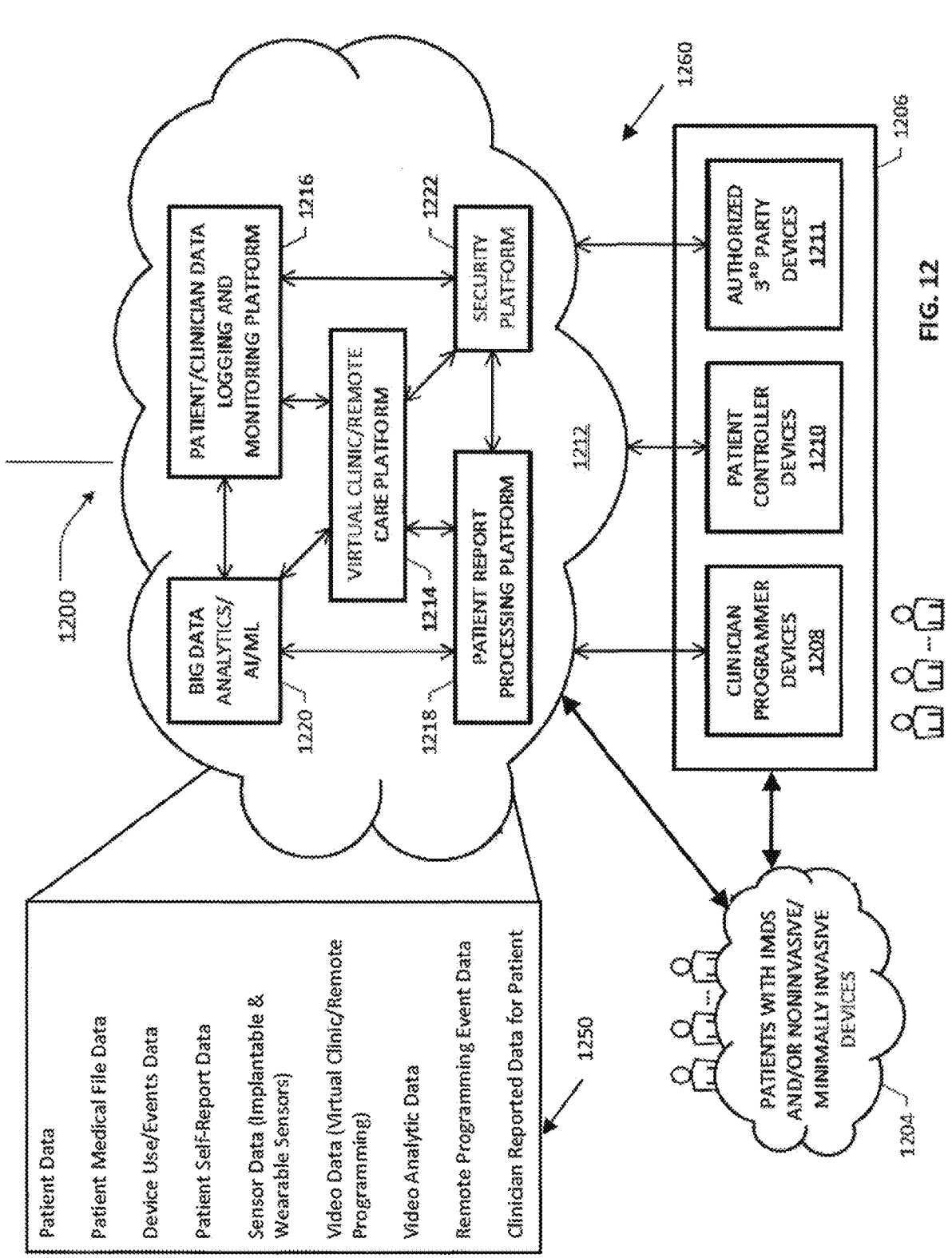
Figure 14:
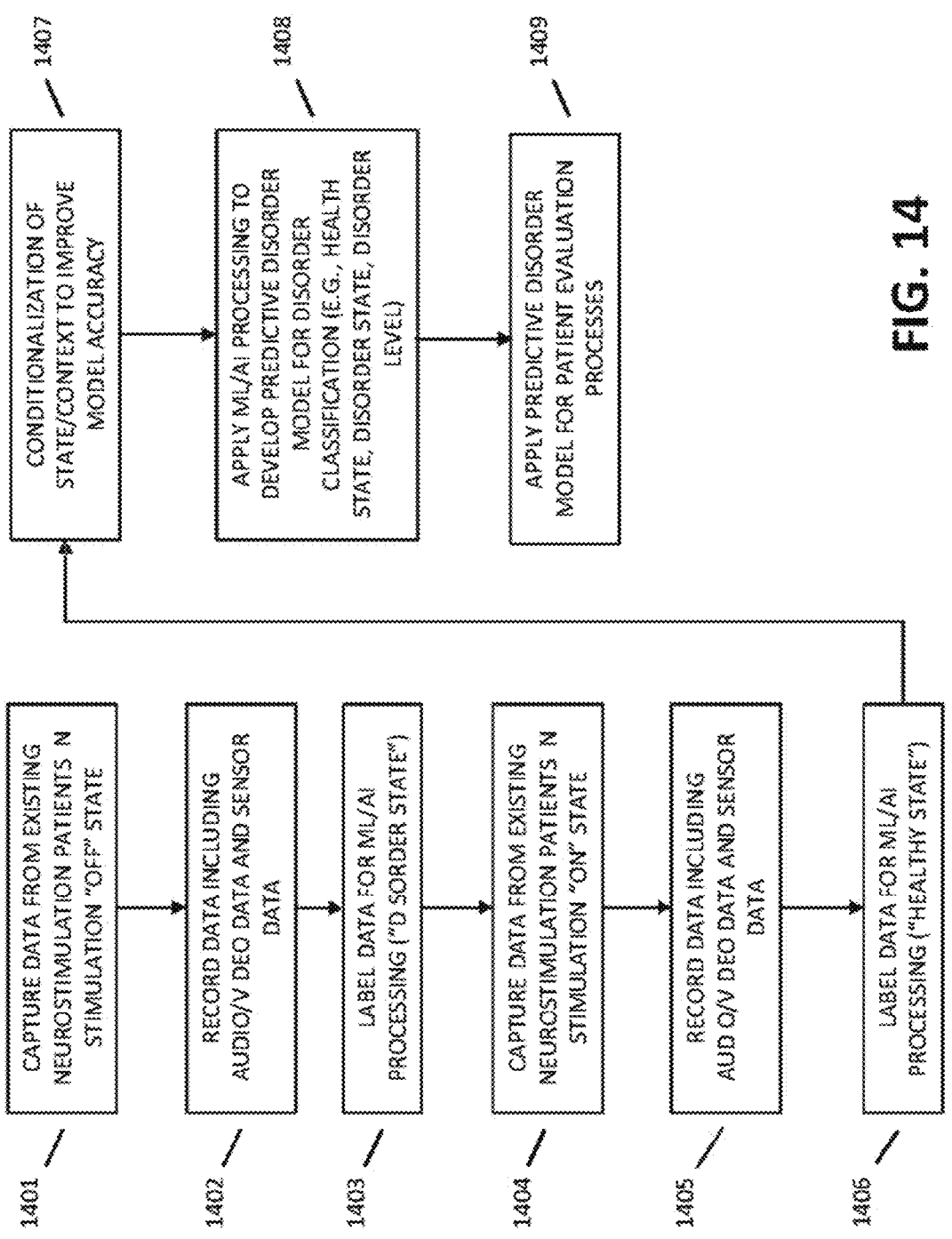
Figure 15:
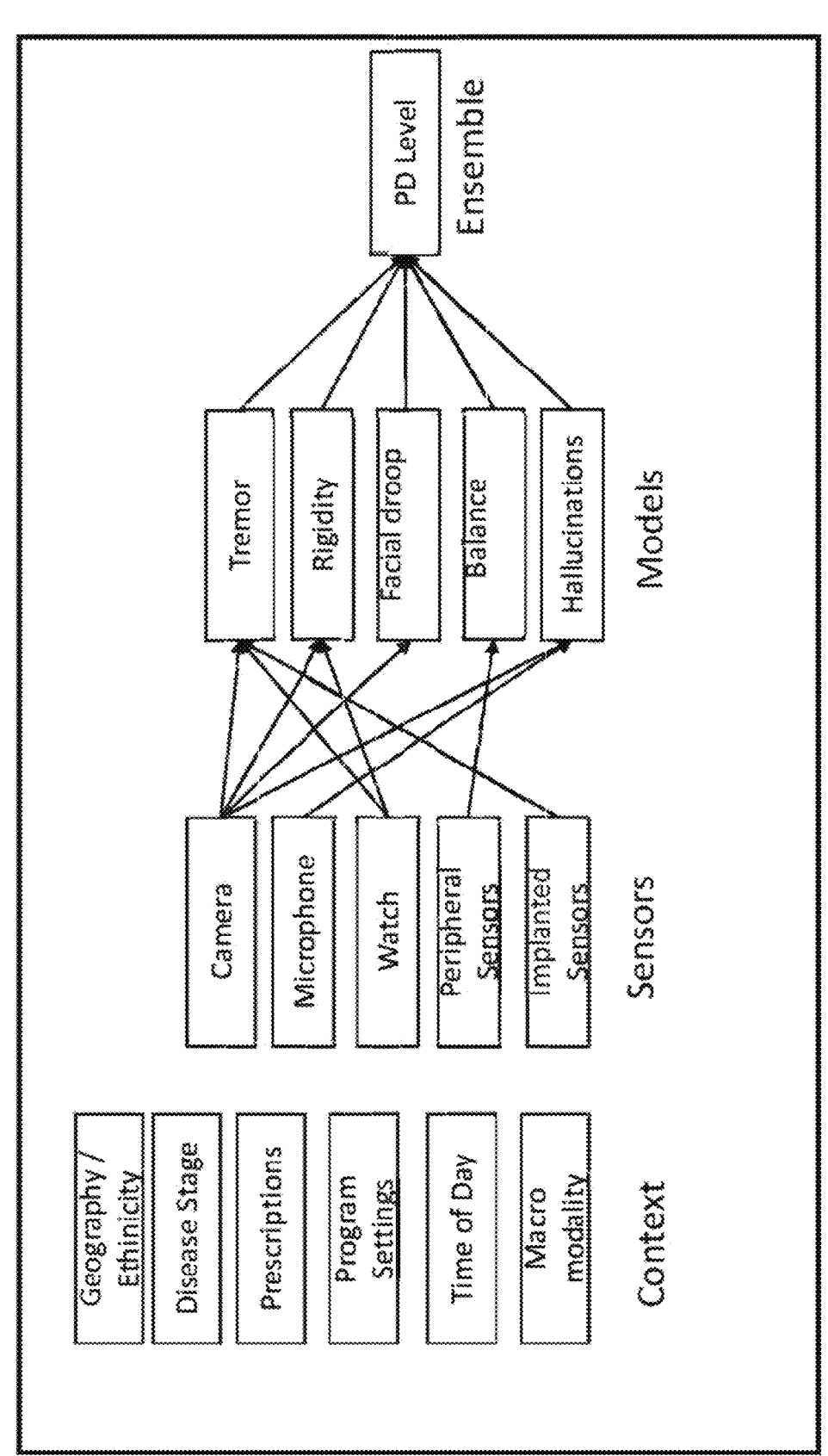
Figures 17A, 17B:
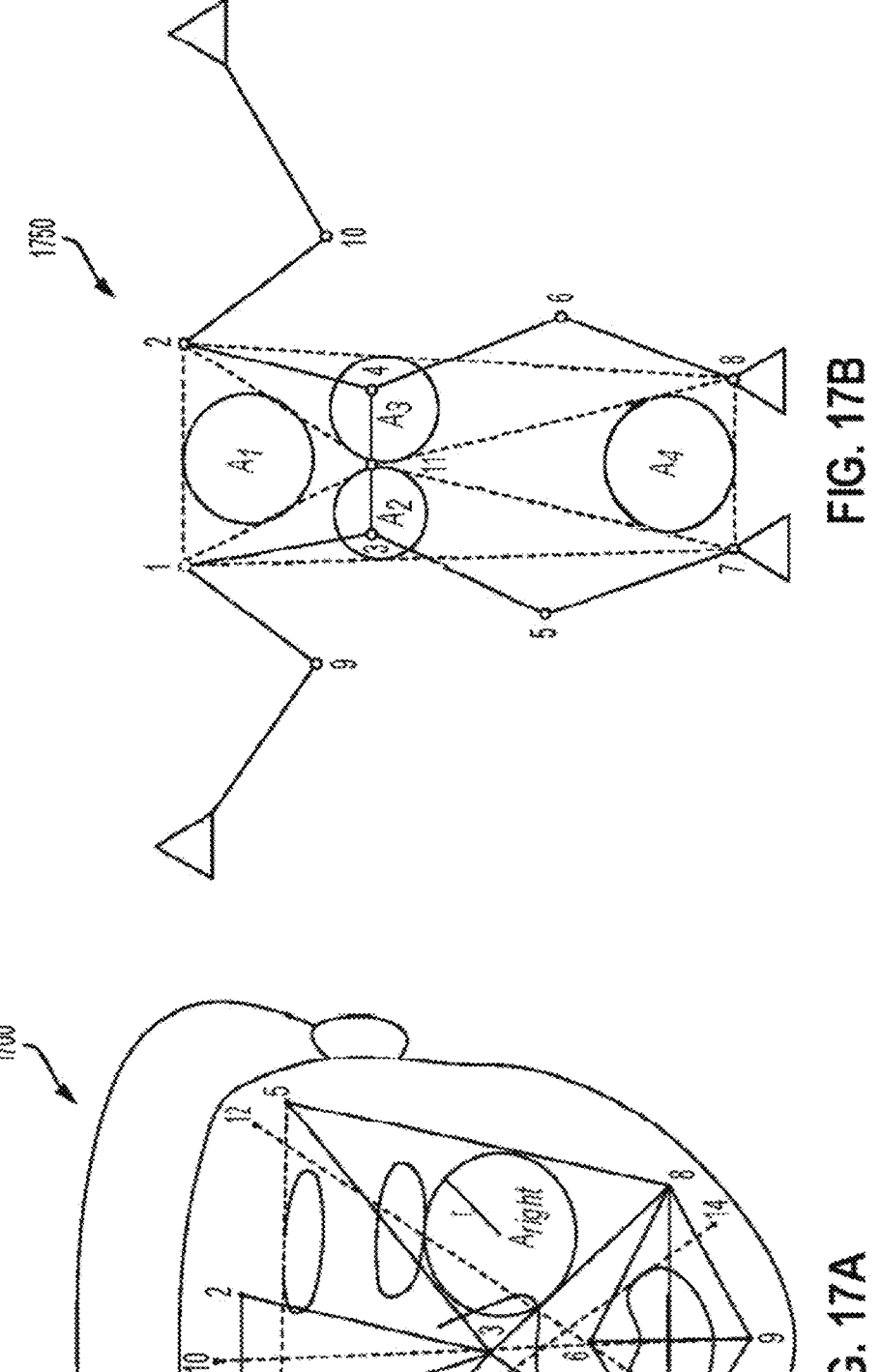
Figures 20, 21:
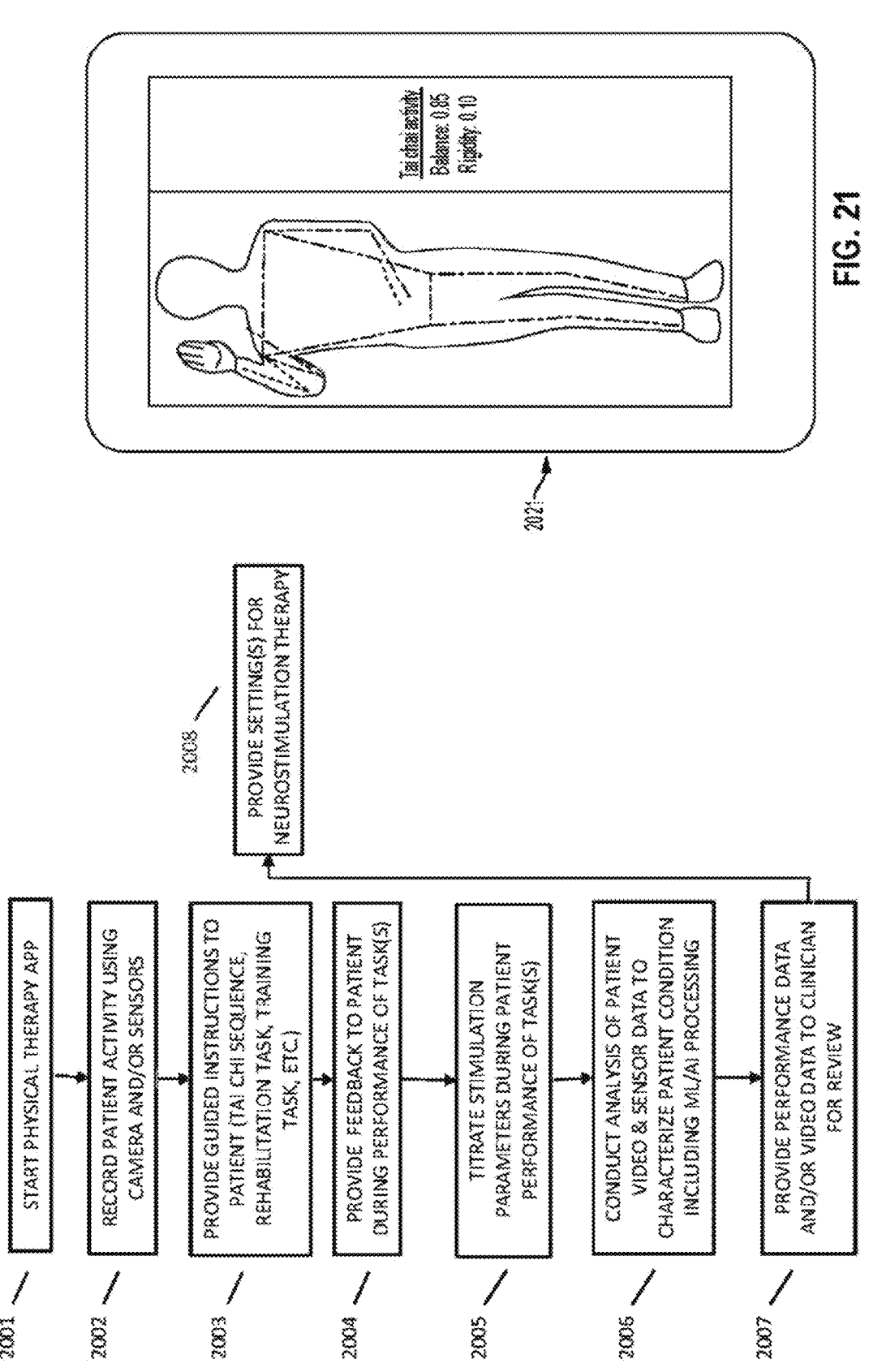

3 therapy session in an integrated remote care service application for purposes of an embodiment of the present disclosure;

FIG. 12 depicts an example cloud-centric digital healthcare network architecture including one or more virtual clinic platforms, patient report processing platforms and remote data logging platforms for purposes of some example embodiments of the present disclosure;

FIG. 13 a flowchart depicting operations that may occur during a virtual clinic or remote programming session according to embodiments of the present disclosure;

FIG. 14 is a flowchart depicting an exemplary flor of operations for creating a predictive disorder model using ML/AI processing according to some embodiments;

FIG. 15 depicts aspects of ML/AI learning data sets and predictive models according to embodiments;

FIG. 16 is a flowchart depicting exemplary operations for processing video data to support provision of neurostimulation therapies to patient according to some embodiments;

FIG. 17A-17B depict sets of key landmark points that may be utilized for facial expression analysis and pose analysis according to some embodiments;

FIG. 18A-18D show screenshots illustrating exemplary aspects of user interfaces utilized to control and view information during a virtual or remote session conducted according to some embodiments;

FIG. 19 is a flowchart depicting exemplary operations for conducting a virtual clinic/remote programming session according to some embodiments;

FIG. 20 is a flowchart depicting exemplary operations for conducting a physical therapy session in accordance with some embodiments; and FIG. 21 is a screenshot of an exemplary graphical user interface for presenting performance data associated with a patient.

Figure 22:
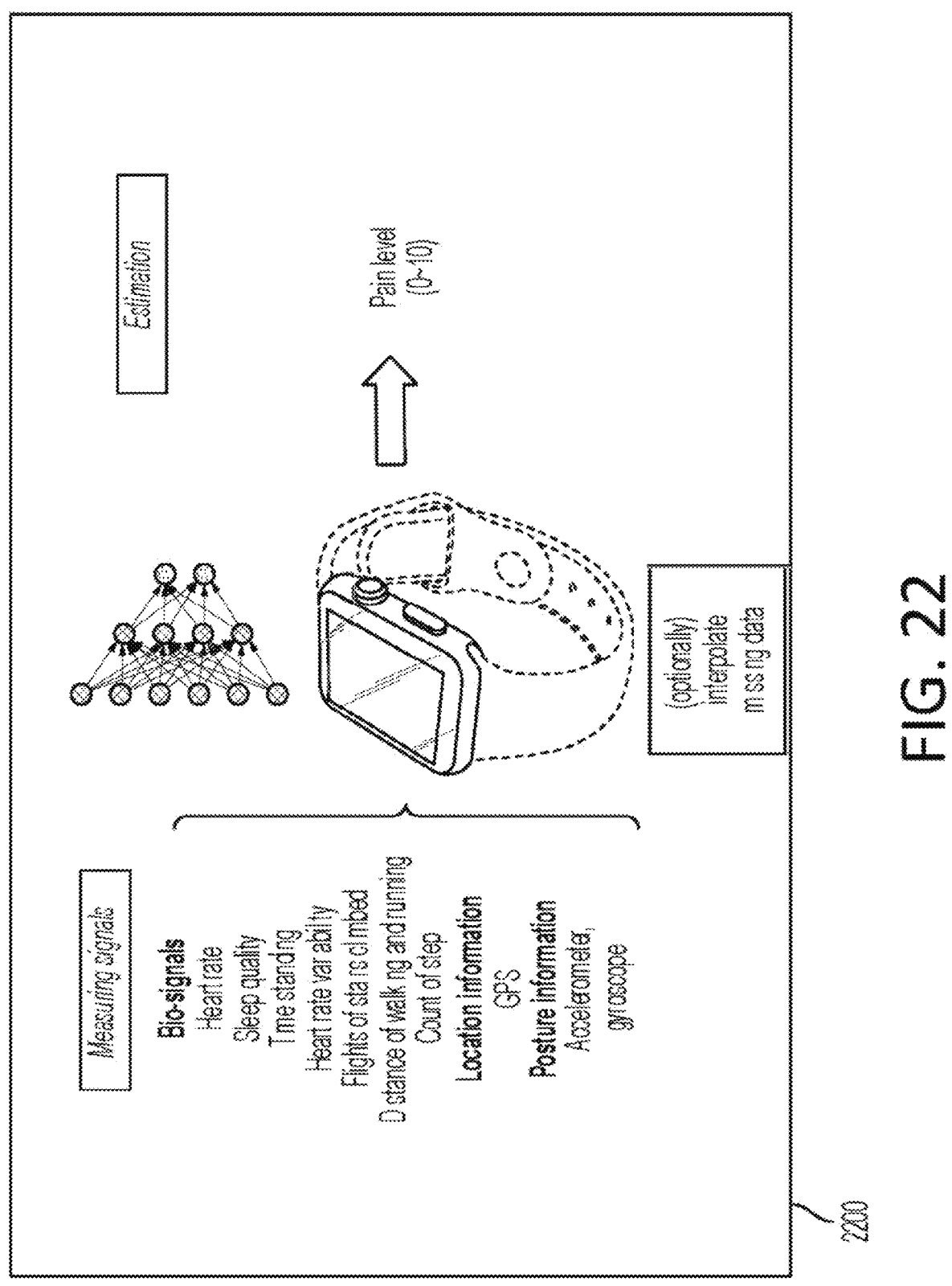
Figure 23:
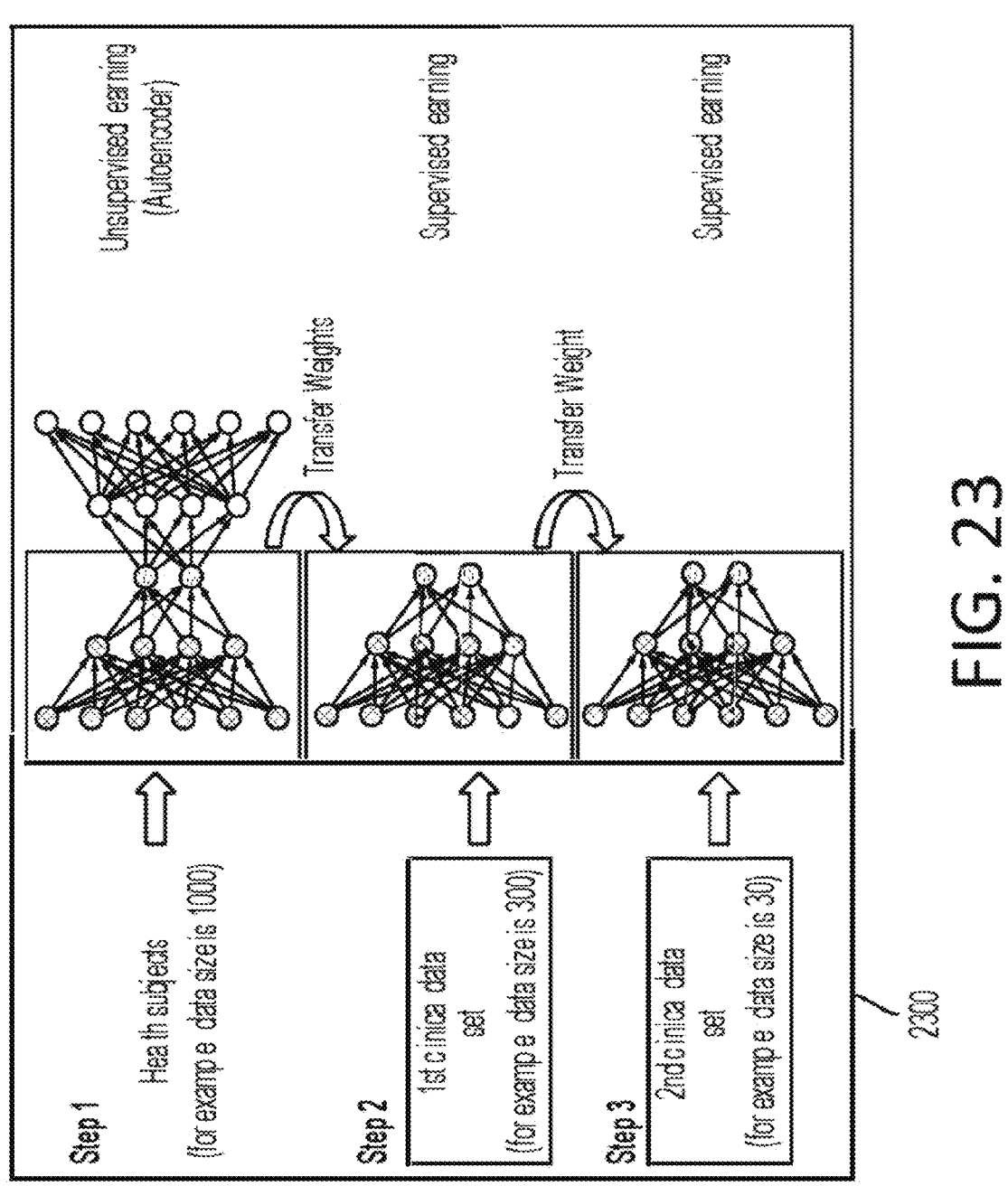

FIGS. 22 and 23 depict processing of patient data from a wearable device to control neurostimulation according to some representative embodiments.

Figure 24:
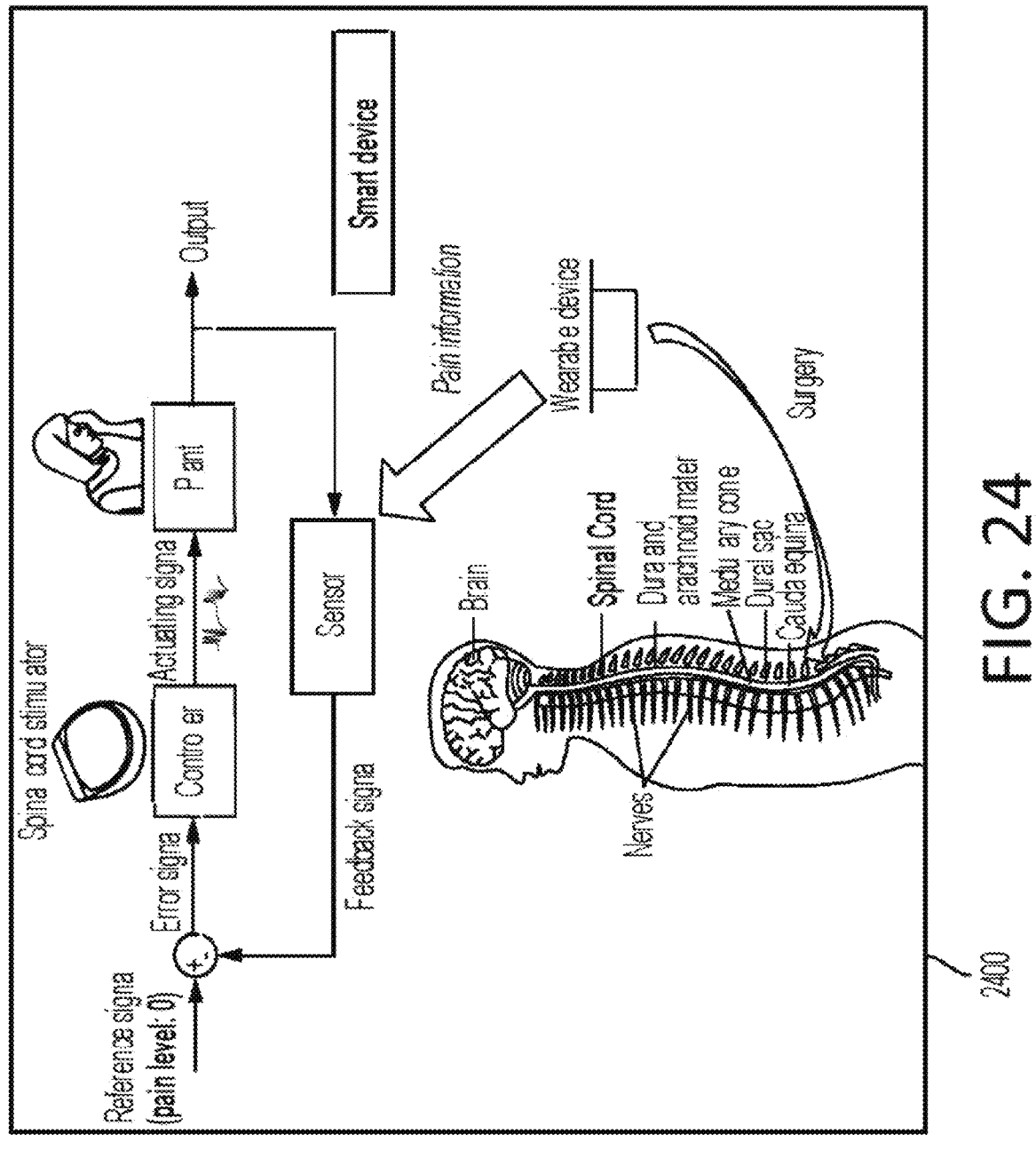

FIG. 24 depicts a neurostimulation system for providing a neurostimulation therapy to a patient according to some representative embodiments.

Figure 25:
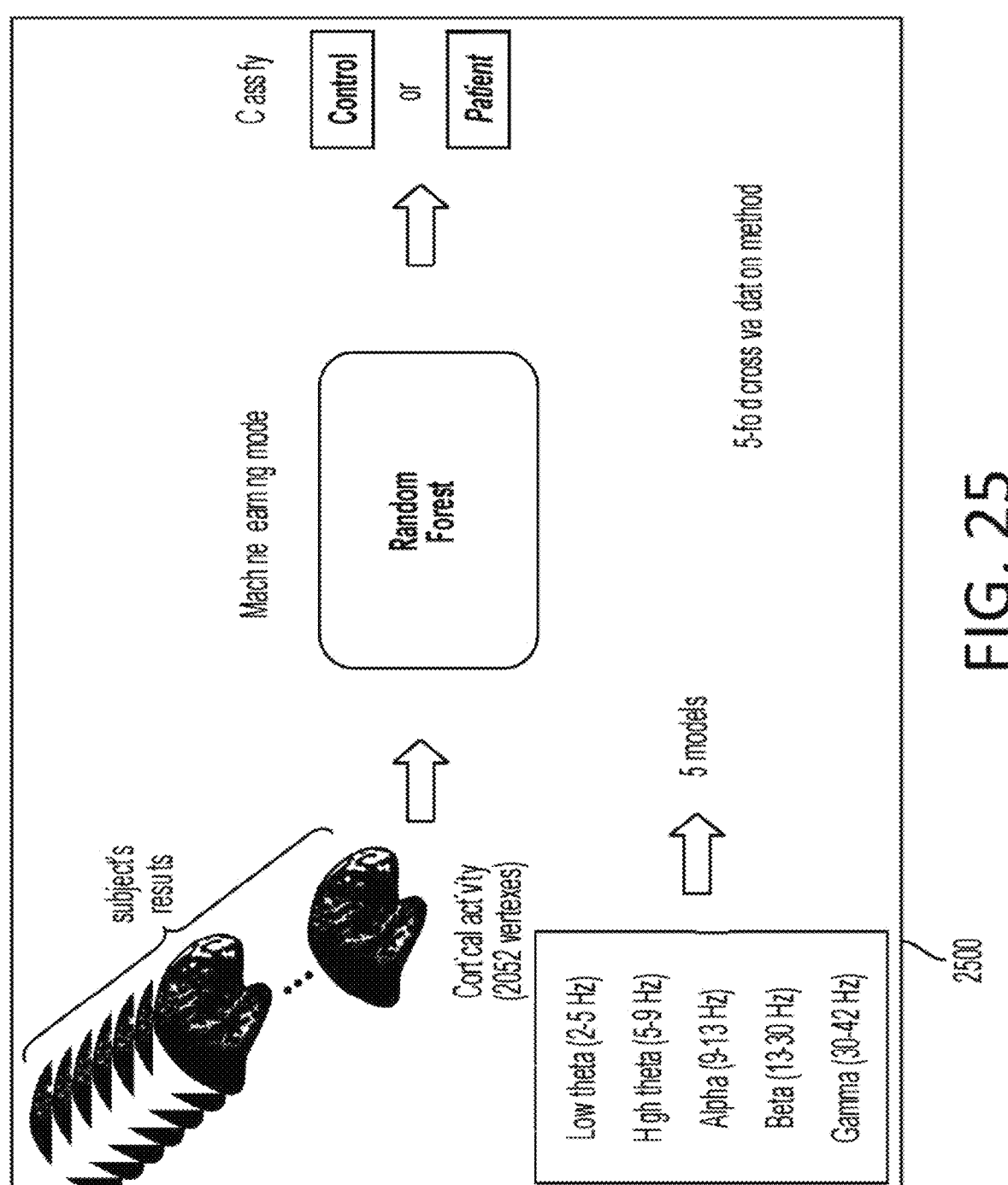
Figure 26:
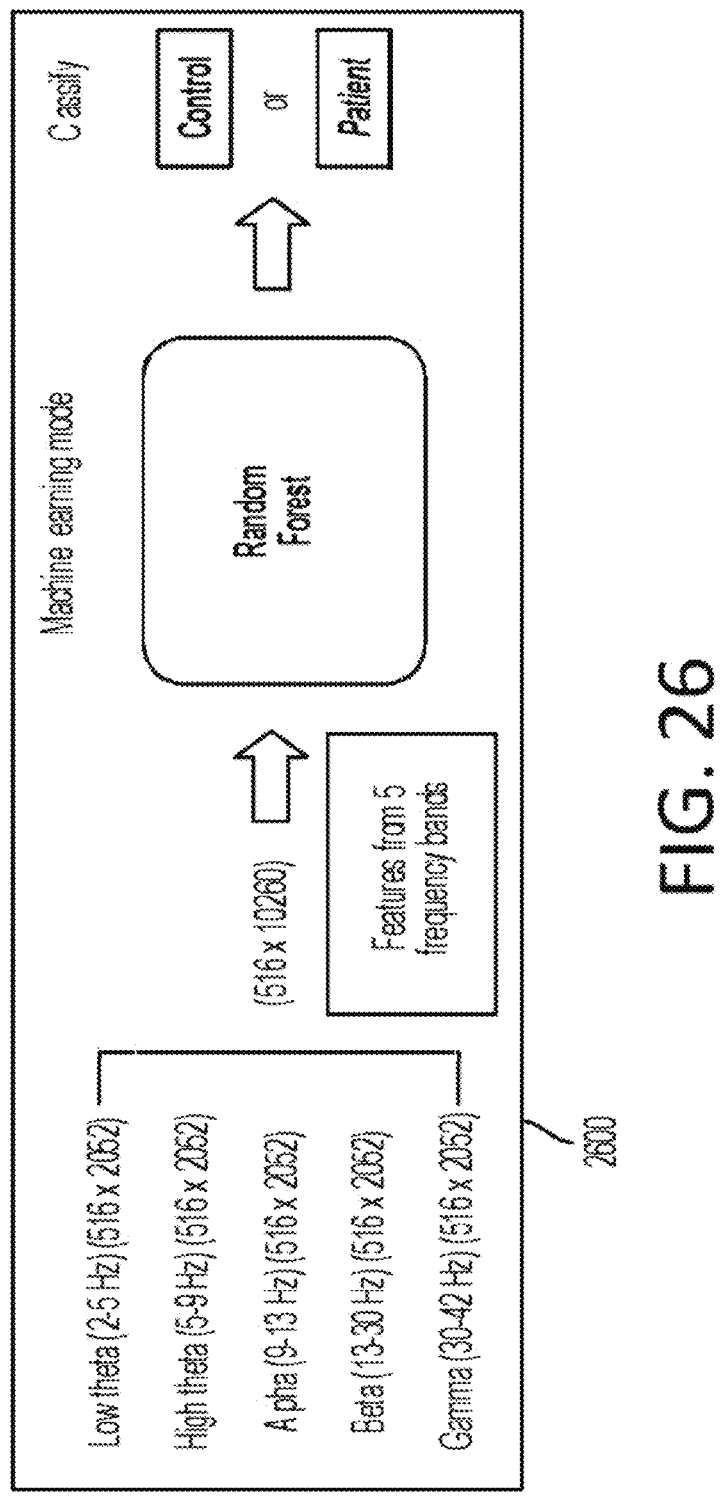

FIGS. 25 and 26 depicts processing of patient cortical activity data from a to control neurostimulation according to some representative embodiments.

Figure 27:
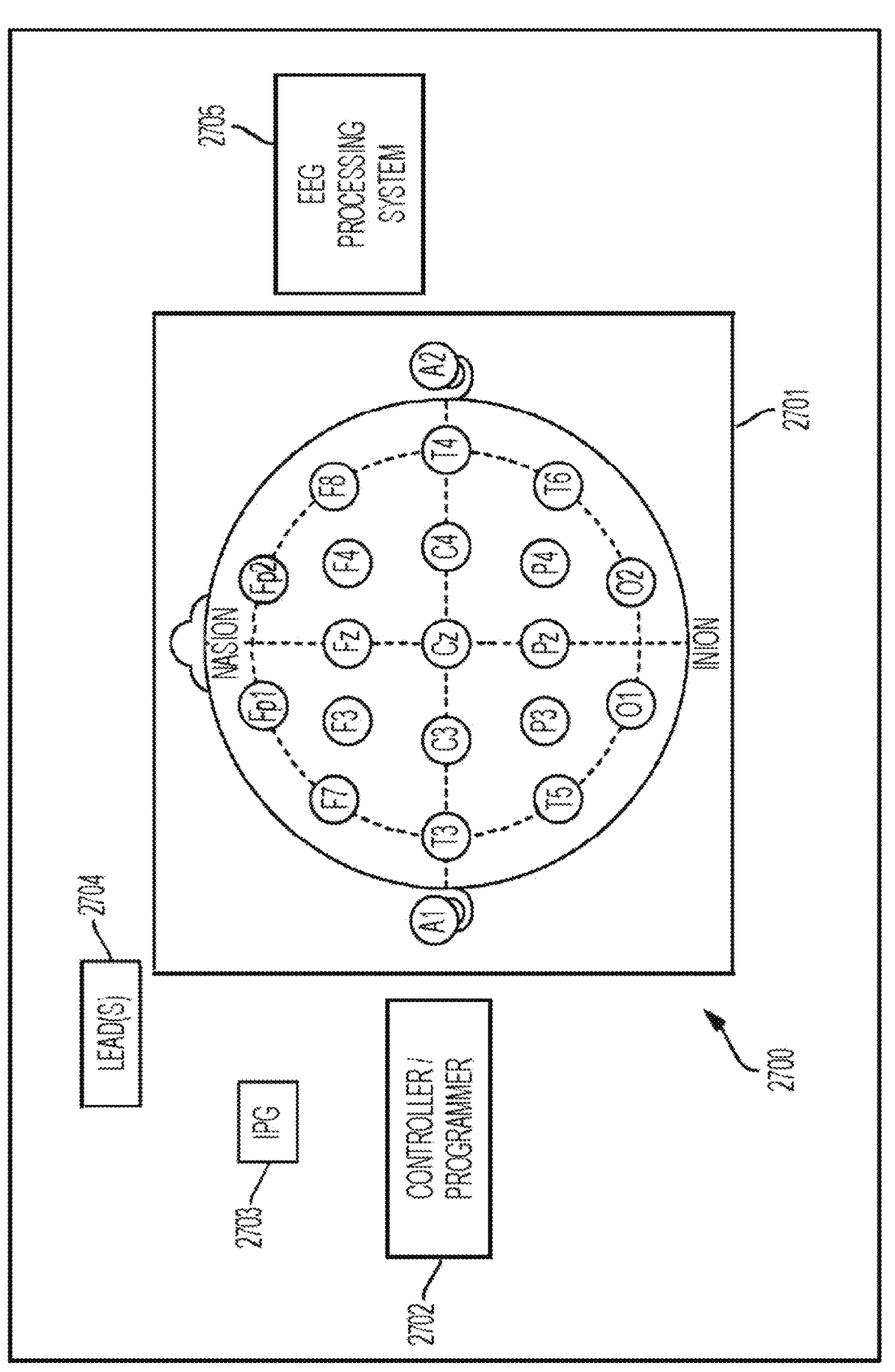

FIG. 27 depicts a system for providing neurostimulation to a patient using EEG data according to some representative embodiments.

Figures 28, 29:
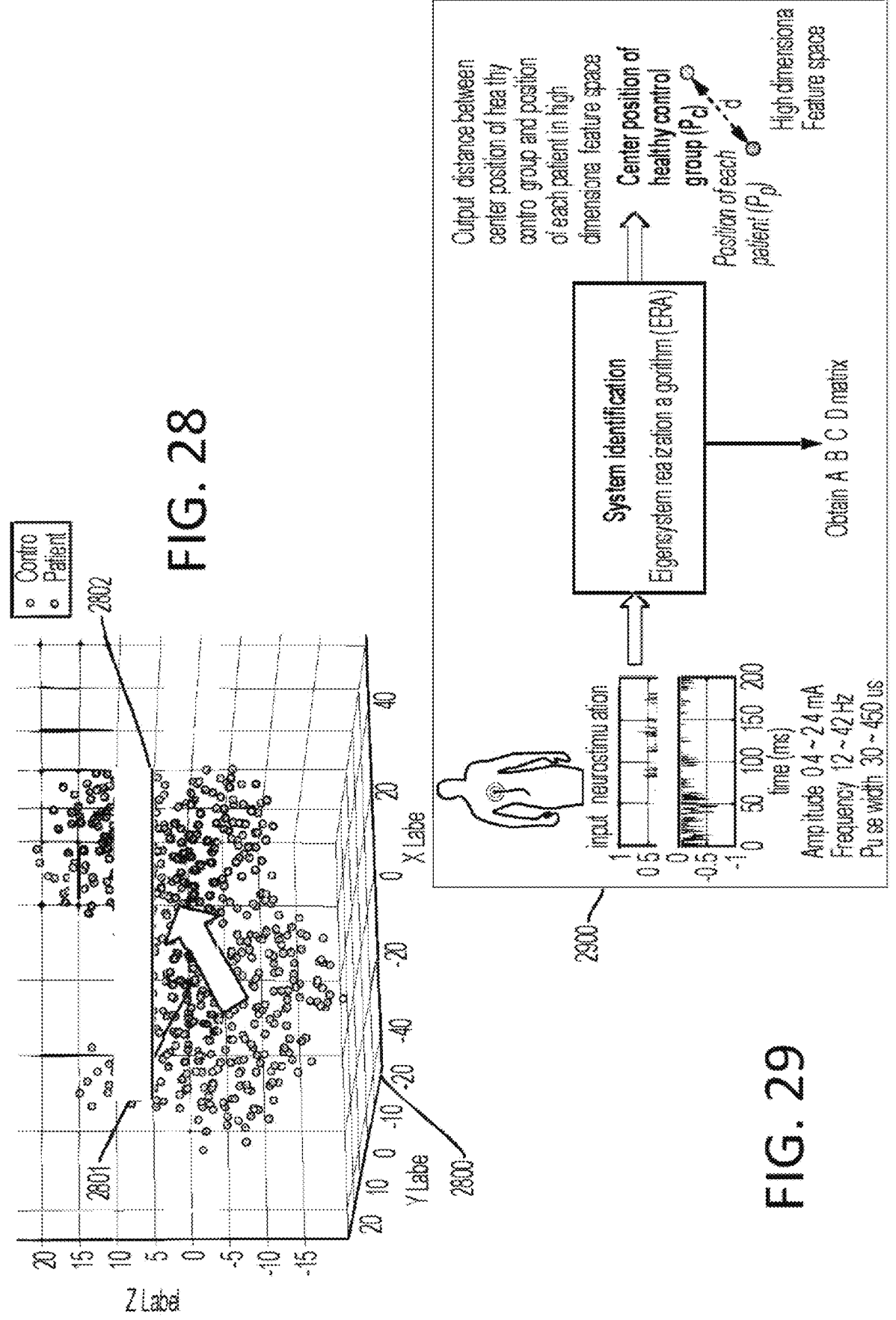

FIG. 28 depicts a graph for providing a representation of a multi-dimensional representative of a patient state relative to other patient and/or healthy control populations.

FIG. 29 depicts a system for providing neurostimulation to a patient using patient data according to some representative embodiments.

Figures 30, 31:
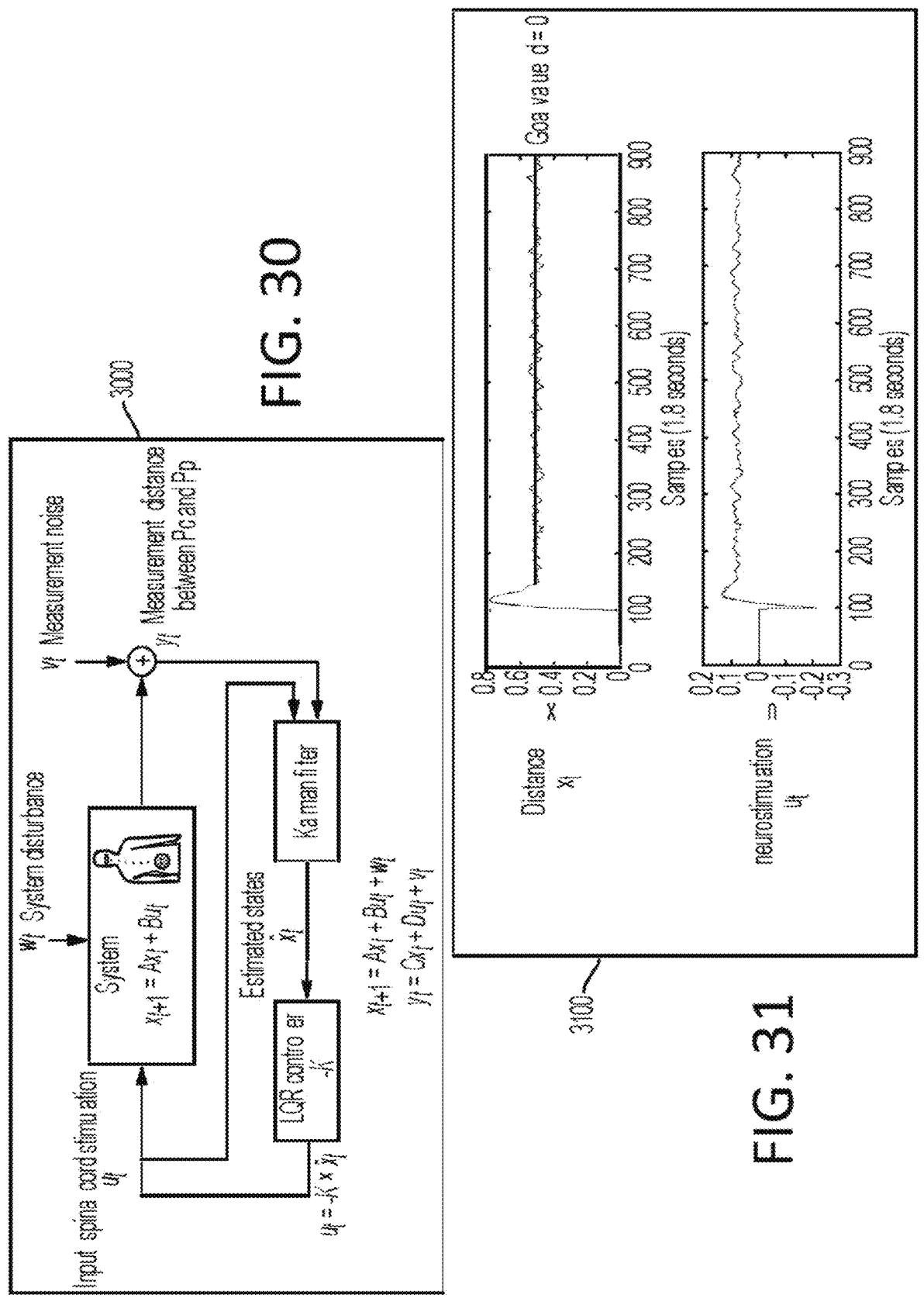

FIG. 30 depicts a system for providing neurostimulation to a patient using patient data according to some representative embodiments.

FIG. 31 depicts use of a multi-dimensional representation of patient features to control neurostimulation according to some representative embodiments.

Figures 32, 33:
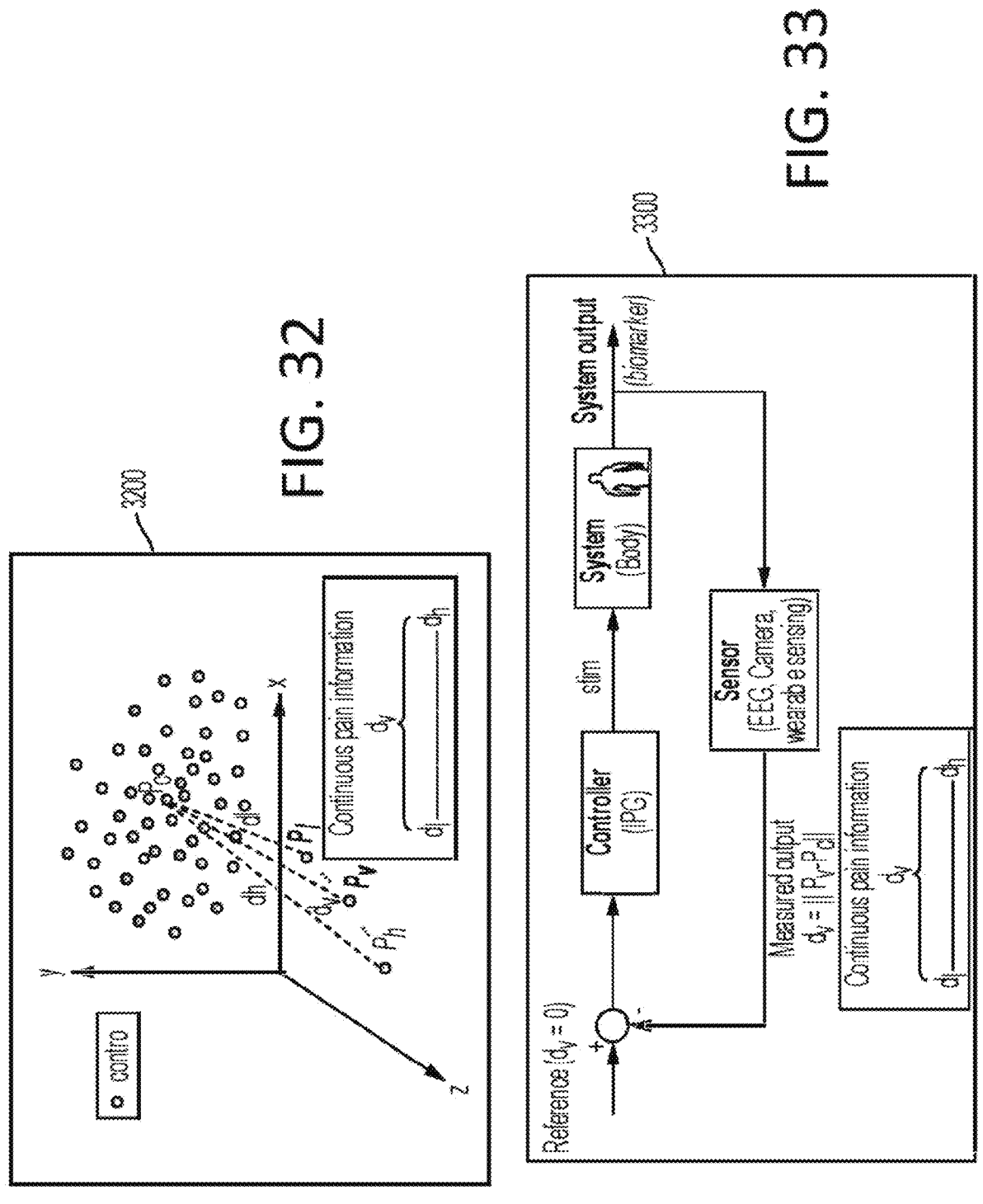

FIG. 32 depicts a graph for providing a representation of a multi-dimensional representative of a patient state relative to other patient and/or healthy control populations according to some embodiments.

FIG. 33 depicts use of a multi-dimensional representation of patient features to control neurostimulation according to some representative embodiments.

4

Figures 34, 35:
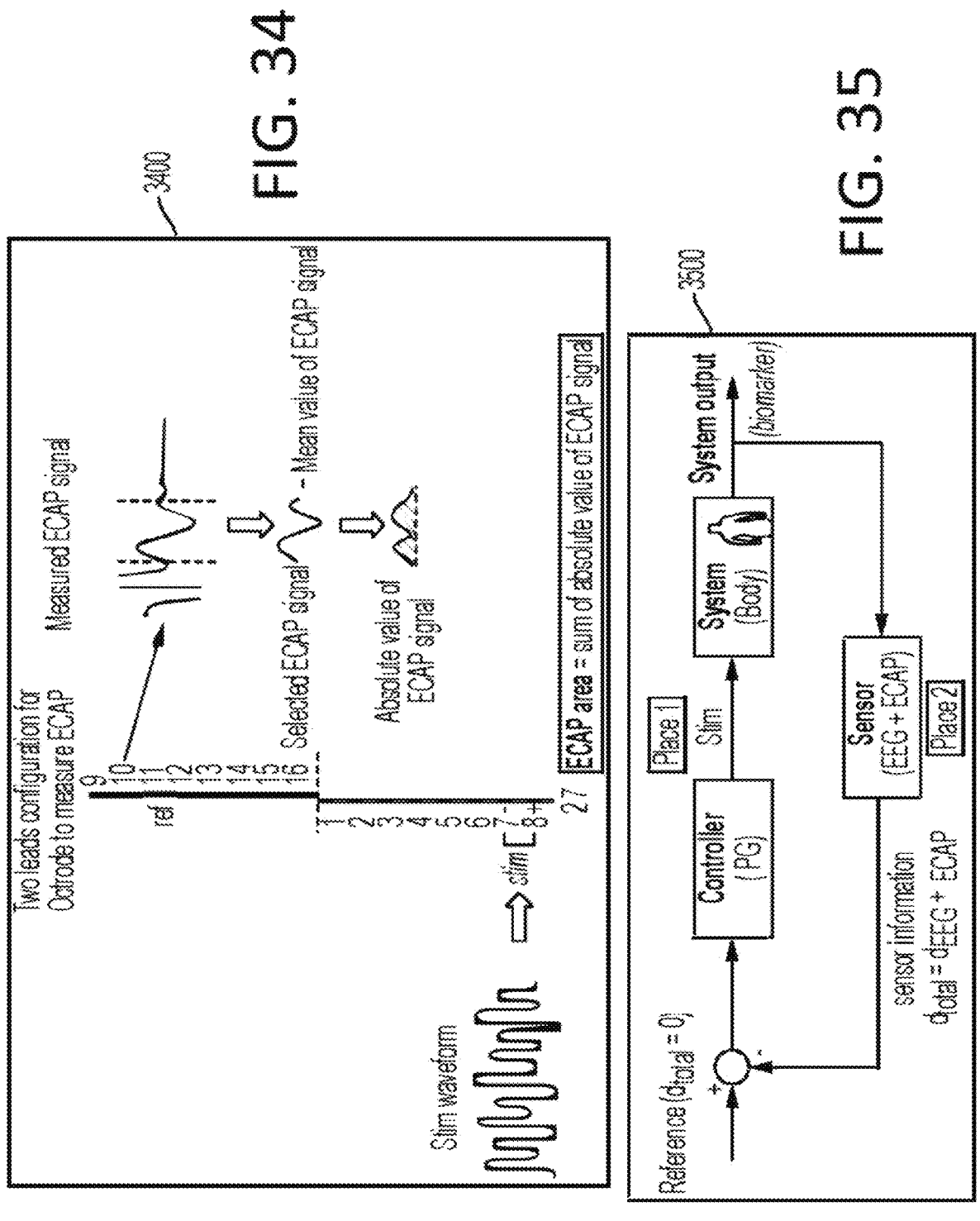

FIG. 34 depicts processing of ECAP data to use in a multi-dimensional representation of patient features to control neurostimulation according to some representative embodiments.

FIG. 35 depicts a system for providing neurostimulation to a patient using patient data according to some representative embodiments.

Figures 36, 37:
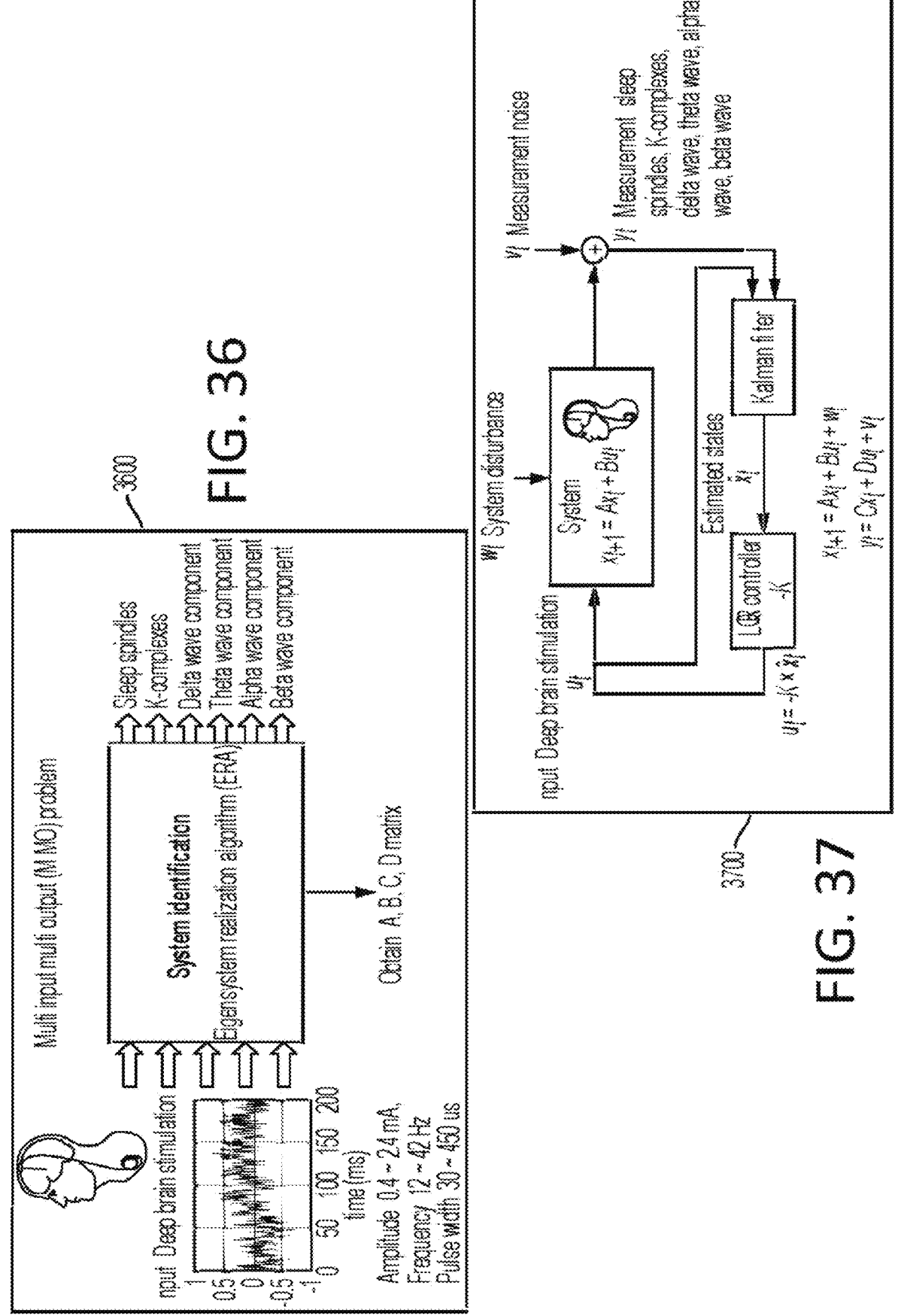

FIG. 36 depicts a system for providing neurostimulation to a patient using patient data according to some representative embodiments.

FIG. 37 depicts a system for providing neurostimulation to a patient using patient data according to some representative embodiments.

Figures 38, 39:
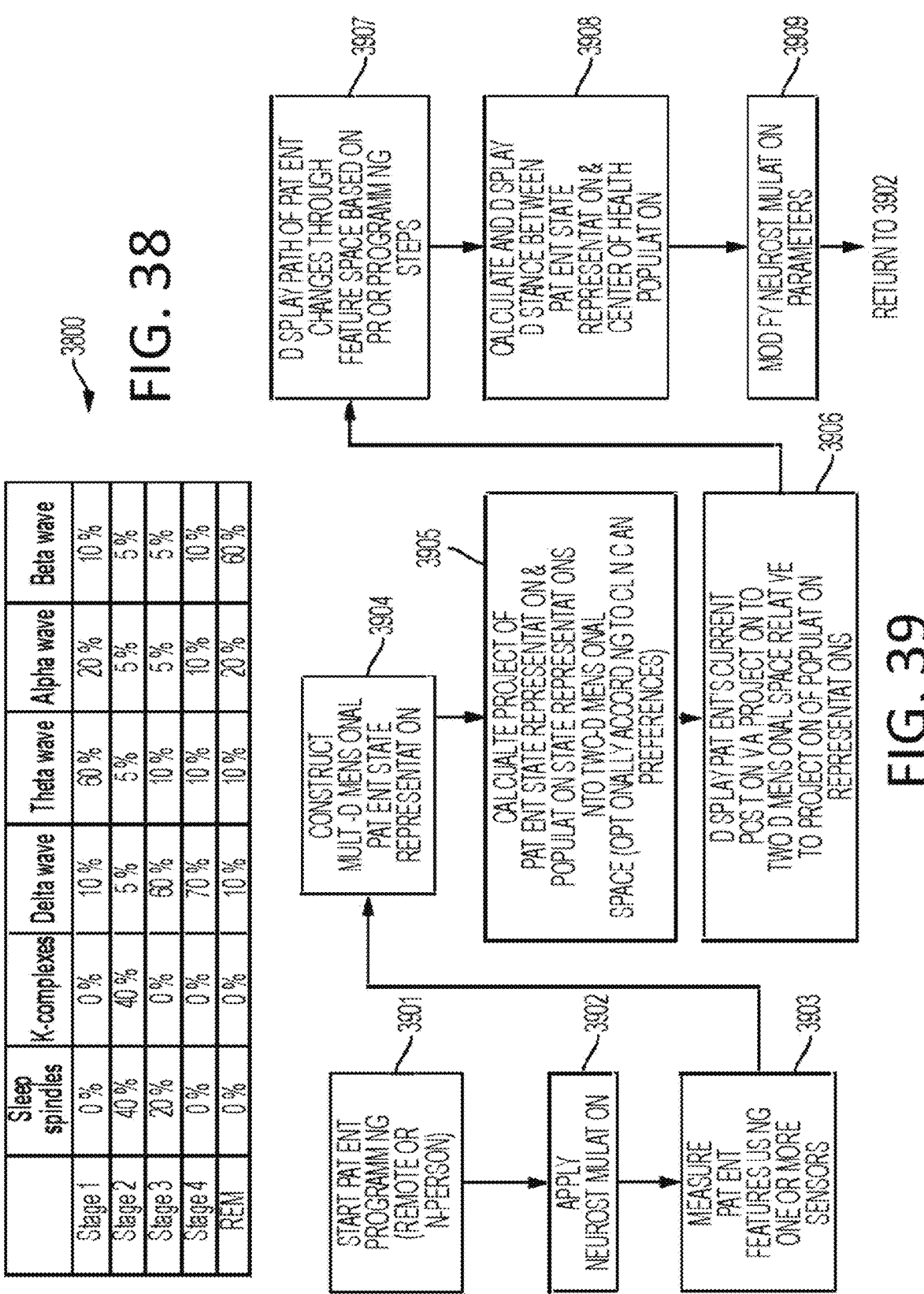

FIG. 38 depicts waveform characteristics for providing neurostimulation to a patient using patient data according to some representative embodiments.

FIG. 39 depicts a process for assisting programming of a neurostimulation therapy for a patient according to some representative embodiments.

Figure 40:
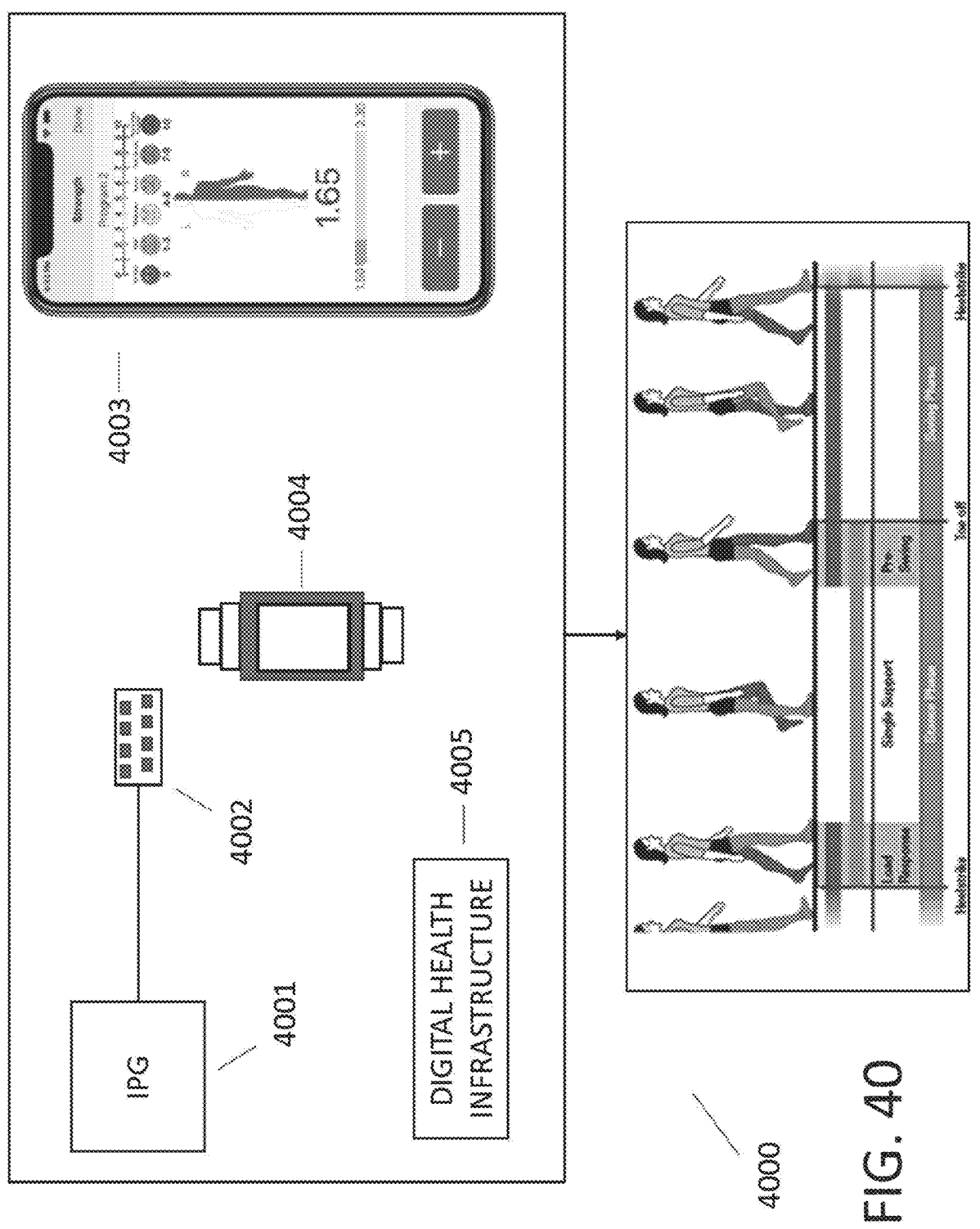

FIG. 40 depicts a neurostimulation system according to some embodiments.

Figure 41:
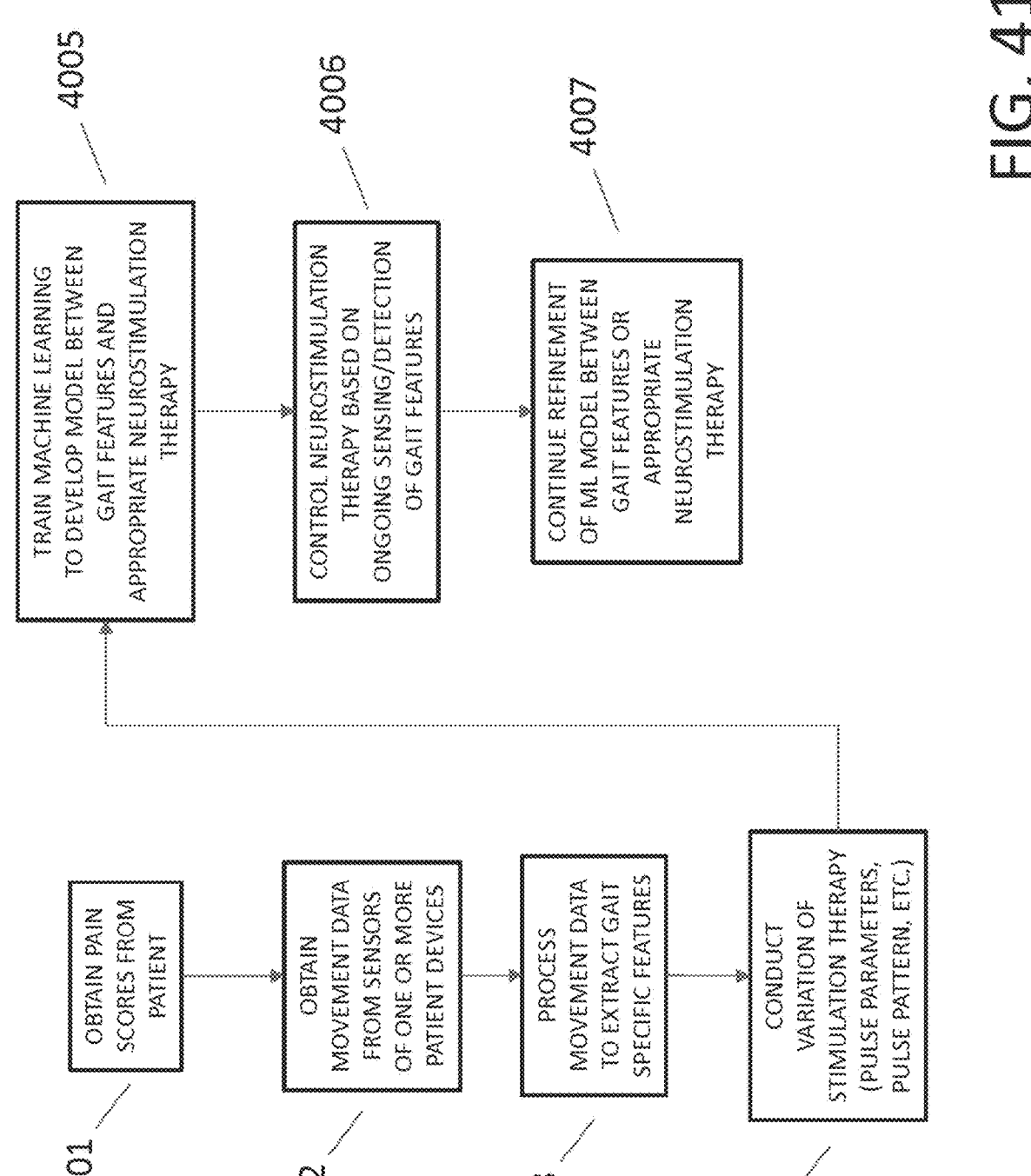

FIG. 41 depicts provisional of a neurostimulation therapy according to some embodiments.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like set forth in reference to other embodiments herein. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Example embodiments described herein relate to aspects of implementations of an integrated digital health network architecture that may be effectuated as a convergence of various technologies involving diverse end user devices and computing platforms, heterogeneous network connectivity environments, agile software as a medical device (SaMD) deployments, data analytics and machine learning, secure cloud-centric infrastructures for supporting remote healthcare, etc. Some embodiments may be configured to support various types of healthcare solutions including but not limited to remote patient monitoring, integrated session management for providing telehealth applications as well as remote care therapy applications, personalized therapy based on advanced analytics of patient and clinician data, remote trialing of neuromodulation therapies, e.g., pain management/amelioration solutions, and the like. Whereas some example embodiments may be particularly set forth with respect to implantable pulse generator (IPG) or neuromodulator systems for providing therapy to a desired area of a body or tissue based on a suitable stimulation therapy application, such as spinal cord stimulation (SCS) systems or other neuromodulation systems, it should be understood that example embodiments disclosed herein are not limited thereto but have broad applicability. Some example remote care therapy applications may therefore involve different types of implantable devices such as neuromuscular stimulation systems and sensors, dorsal root ganglion (DRG) stimulation systems, deep brain stimulation systems, cochlear implants, retinal implants, implantable cardiac rhythm management devices, implantable cardioverter defibrillators, pacemakers, and the like, as well as implantable drug delivery/infusion systems, implantable devices configured to effectuate real-time measurement/monitoring of one or more physiological functions of a patient's body (i.e., patient physiometry), including various implantable biomedical sensors and sensing systems. Further, whereas some example embodiments of remote care therapy applications may involve implantable devices, additional and/or alternative embodiments may involve external personal devices and/or noninvasive/minimally invasive (NIMI) devices (e.g., wearable biomedical devices, transcutaneous/subcutaneous devices, etc.) that may be configured to provide therapy to the patients analogous to the implantable devices. Accordingly, all such devices may be broadly referred to as "personal medical devices," "personal biomedical instrumentation," or terms of similar import, at least for purposes of some example embodiments of the present disclosure.

As used herein, a network element, platform or node may be comprised of one or more pieces of network equipment, including hardware and software that communicatively interconnects other equipment on a network (e.g., other network elements, end stations, etc.), and is adapted to host one or more applications or services, more specifically healthcare applications and services, with respect to a plurality of end users (e.g., patients, clinicians, respective authorized agents, and associated client devices) as well as other endpoints such as medical- and/or health-oriented Internet of Medical Things (IoMT) devices/sensors and/or other Industrial IoT-based entities. As such, some network elements may be operatively disposed in a cellular wireless or satellite telecommunications network, or a broadband wireline network, whereas other network elements may be disposed in a public packet-switched network infrastructure (e.g., the Internet or worldwide web, also sometimes referred to as the "cloud"), private packet-switched network infrastructures such as Intranets and enterprise networks, as well as service provider network infrastructures, any of which may span or involve a variety of access networks, backhaul and core networks in a hierarchical arrangement. In still further arrangements, one or more network elements may be disposed in cloud-based platforms or datacenters having suitable equipment running virtualized functions or applications, which may be configured for purposes of facilitating patient monitoring, remote therapy, other telehealth/telemedicine applications, etc. for purposes of one or more example embodiments set forth hereinbelow.

One or more embodiments of the present patent disclosure may be implemented using different combinations of software, firmware, and/or hardware. Thus, one or more of the techniques shown in the Figures (e.g., flowcharts) may be implemented using code and data stored and executed on one or more electronic devices or nodes (e.g., a subscriber client device or end station, a network element, etc.). Such electronic devices may store and communicate (internally and/or with other electronic devices over a network) code and data using computer-readable media, such as non-transitory computer-readable storage media (e.g., magnetic disks, optical disks, random access memory, read-only memory, flash memory devices, phase-change memory, etc.), transitory computer-readable transmission media (e.g., electrical, optical, acoustical or other form of propagated signals—such as carrier waves, infrared signals, digital signals), etc. In addition, such network elements may typically include a set of one or more processors coupled to one or more other components, such as one or more storage devices (e.g., non-transitory machine-readable storage media) as well as storage database(s), user input/output devices (e.g., a keyboard, a touch screen, a pointing device, and/or a display), and network connections for effectuating signaling and/or bearer media transmission.

Without limitation, an example cloud-centric digital healthcare network architecture involving various network-based components, subsystems, service nodes etc., as well as myriad end user deployments concerning patients, clinicians and authorized third-party agents is illustrated in FIG. 12 wherein one or more embodiments of the present patent disclosure may be practiced. In one arrangement, example architecture 1260 may include one or more virtual clinic platforms 1214, remote data logging platforms 1216, patient/clinician report processing platforms 1218, as well as data analytics platforms 1220 and security platforms 1222, at least some of which may be configured and/or deployed as an integrated digital health infrastructure 1212 for effectuating some example embodiments of the present disclosure. One or more pools of patients having a myriad of health conditions and/or receiving assorted treatments, who may be geographically distributed in various locations, areas, regions, etc., are collectively shown at reference numeral 1204, wherein individual patients may be provided with one or more suitable IMDs/IPGs, NIMI devices, other personal biomedical instrumentation, etc., depending on respective patients' health conditions and/or treatments. A plurality of clinician programmer devices 1208, patient controller devices 1210, and authorized third-party devices 1211 associated with respective users (e.g., clinicians, medical professionals, patients and authorized agents thereof) may be deployed as external devices 1206 that may be configured to interact with patients' IMDs and/or NIMI devices for effectuating therapy, monitoring, data logging, secure file transfer, etc., via local communication paths or over network-based remote communication paths established in conjunction with the digital health infrastructure network 1212.

Clinician controller device 1208 may permit programming of IPG 170 to provide a number of different stimulation patterns or therapies to the patient as appropriate for a given patient and/or disorder. Examples of different stimulation therapies include conventional tonic stimulation (continuous train of stimulation pulses at a fixed rate), BurstDR stimulation (burst of pulses repeated at a high rate interspersed with quiescent periods with or without duty cycling), "high frequency" stimulation (e.g., a continuous train of stimulation pulses at 10,000 Hz), noise stimulation (series of stimulation pulses with randomized pulse characteristics such as pulse amplitude to achieve a desired frequency domain profile). Any suitable stimulation pattern or combination thereof can be provided by IPG 170 according to some embodiments. Controller device 1208 communicates the stimulation parameters and/or a series of pulse characteristics defining the pulse series to be applied to the patient to IPG 170 to generate the desired stimulation therapy.

IPG 170 may be adapted to apply a variety of neurostimulation therapies while controller device 1208 may send signals to IPG 170 related to such therapies. Examples of suitable therapies include tonic stimulation (in which a fixed frequency pulse train) is generated, burst stimulation (in which bursts of multiple high frequency pulses) are generated which in turn are separated by quiescent periods, "high frequency" stimulation, multi-frequency stimulation, and noise stimulation. Descriptions of respective neurostimulation therapies are provided in the following publications: (1) Schu S., Slotty P. J., Bara G., von Knop M., Edgar D., Vesper J. A Prospective, Randomised, Double-blind, Placebo-controlled Study to Examine the Effectiveness of Burst Spinal Cord Stimulation Patterns for the Treatment of Failed Back Surgery Syndrome. Neuromodulation 2014; 17: 443-450; (2) Al-Kaisy A1, Van Buyten J P, Smet I, Palmisani S, Pang D, Smith T. 2014. Sustained effectiveness of 10 kHz high-frequency spinal cord stimulation for patients with chronic, low back pain: 24-month results of a prospective multicenter study. Pain Med. 2014 March; 15(3):347-54; and (3) Sweet, Badjatiya, Tan D1, Miller. Paresthesia-Free High-Density Spinal Cord Stimulation for Postlaminectomy Syndrome in a Prescreened Population: A Prospective Case Series. Neuromodulation. 2016 April; 19(3):260-7. Noise stimulation is described in U.S. Pat. No. 8,682,441B2. Burst stimulation is described in U.S. Pat. No. 8,224,453 and U.S. Published Application No. 20060095088. A "coordinated reset" pulse pattern is applied to neuronal subpopulation/target sites to desynchronize neural activity in the subpopulations. Coordinated reset stimulation is described, for example, by Peter A. Tass et al in COORDINATED RESET HAS SUSTAINED AFTER EFFECTS IN PARKINSONIAN MONKEYS, Annals of Neurology, Volume 72, Issue 5, pages 816-820, November 2012, which is incorporated herein by reference. The electrical pulses in a coordinated reset pattern are generated in bursts of pulses with respective bursts being applied to tissue of the patient using different electrodes in a time-offset manner. The time-offset is selected such that the phase of the neural-subpopulations are reset in a substantially equidistant phase-offset manner. By resetting neuronal subpopulations in this manner, the population will transition to a desynchronized state by the interconnectivity between the neurons in the overall neuronal population. All of these references are incorporated herein by reference.

In one arrangement, example architecture 1260 may encompass a hierarchical/heterogeneous network arrangement comprised of one or more fronthaul radio access network (RAN) portions or layers, one or more backhaul portions or layers, and one or more core network portions or layers, each of which may in turn include appropriate telecommunications infrastructure elements, components, etc., cooperatively configured for effectuating a digital healthcare ecosystem involving patients' IMDs and/or NIMI devices 1204, external devices 1206, and one or more components of the digital health infrastructure network 1212, wherein at least a portion of the components of the infrastructure network 1212 may be operative as a cloud-based system for purposes of some embodiments herein. Further, at least a portion of the components of the digital health infrastructure network 1212 operating as a system 1200, one or more patients' IMDs and/or NIMI devices 1204, and one or more external devices 1206 may be configured to execute suitable medical/health software applications in a cooperative fashion (e.g., in a server-client relationship) for effectuating various aspects of remote patient monitoring, telemedicine/telehealth applications, remote care therapy, etc. Without limitation, example embodiments of the present disclosure may relate to one or more aspects set forth immediately below.

In some example arrangements, a virtual clinic may be configured to provide patients and/or clinicians the ability to perform remote therapies using a secure telehealth session. To enhance clinician interaction and evaluation of a patient during a secure telehealth session, example embodiments herein may be configured to provide specific user interface (UI) layouts and controls for clinician programmer devices and/or patient controller devices for facilitating real-time kinematic and/or auditory data analysis, which may be augmented with suitable artificial intelligence (AI) and/or machine learning (ML) techniques (e.g., neural networks, etc.) in some arrangements. Further, some example embodiments with respect to these aspects may involve providing kinematic UI settings that enable different types of overlays (e.g., with or without a pictorial representation of the patient). Some example embodiments may be configured to enable one or more of the following features and functionalities: (i) separate or combined audio and/or peripheral sensor streams; (ii) capture of assessments from separate or different combinations of body features such as, for example, limbs, hands, face, etc.; (iii) replay of another clinician's video including the patient's kinematic analysis (e.g., a secondary video stream with patient data), and the like.

In some arrangements, video-based real-time kinematic analysis may employ statistical methods within a pipeline of modeling techniques to track inter-frame correlation of images. To maintain real-time operation within a fixed compute environment such as an edge device (e.g., a patient controller device, a clinician programmer device, etc.), the inference latency needs to be less than certain thresholds in order to achieve reliable and/or acceptable performance. Some example embodiments herein may therefore relate to providing a scheme for improving the accuracy of real-time kinematic and/or auditory analysis based on context-aware dynamic (re)configuration of a neural network model or engine trained for facilitating real-time kinematic and/or auditory data analysis.

In some arrangements involving neurostimulation therapy, different stimulation settings and/or programs may be configured for providing varied levels of comfort to the patients, wherein respective patients may likely need to change individual settings depending on a number of factors (e.g., time of day, type(s) and/or level(s) of activities or tasks being engaged by the patients, and the like). Further, continued use of a stimulation program or setting over an extended period of time could result in habituation that may reduce the benefits of therapy. Some example embodiments herein may therefore relate to a system and method for providing recommendations/reconfigurations of program settings based on the patient's usage of the IMD and clinical observations/recommendations, which may facilitate context-sensitive selection of neuromodulation programs/settings.

In some arrangements, video-, audio-, and/or sensing-based analytics and associated ML-based techniques effectuated using one or more constituent components of the digital health infrastructure 1212 may provide valuable insights with respect to the diagnosis/or prognosis of individual patients, especially those having certain neurological disorders. Some of the neurological symptoms may depend on the context (e.g., time of day, activity type, psychological/emotional conditions of the patient, etc.) such that a generalized ML model may not be sufficiently accurate for predictive purposes in a particular setting. Some example embodiments herein may therefore relate to a scheme for rapidly collecting relevant patient data and analyzing/manipulating the data for generating suitable training datasets with respect to select ML-based models using an accelerated inference approach.

Because the video/audio data collected and used for training, validating and testing AI/ML-based models can contain various pieces of personal identification/identifiable information (PII) indicators associated with patients, it is appropriate to protect the privacy of the patient data by providing a suitable end-to-end security architecture. In some related arrangements, one or more constituent components of the digital health infrastructure 1212 may therefore be configured to facilitate secure transfer with respect to the patient data collected for purposes of data analytics and associated ML-based techniques as set forth herein. Some example embodiments in this regard may be configured to provide a scheme for de-identifying data associated with neuromodulation patients, e.g., either in real-time or in a post-processed environment, that still allows implementing ML-based techniques and data sharing in a secure cooperative arrangement. Still further embodiments may relate to facilitating an improved method of removal of identifiable information from video/audio data streams generated pursuant to a therapy session, e.g., a remote therapy session.

In relation to certain aspects of telemedicine, it is recognized that monitoring body rigidity may be an important factor in certain types of motor/neurological disorders, e.g., Parkinson's disease (PD). Rigidity may be defined as an involuntary increase in muscle tone in certain portions of the patient body, e.g., generally affecting arms, neck, leg, hip or trunk of the patient. Rigidity can be classified as lead-pipe when the movement is smooth and consistent or cog-wheeling when it is ratchet-type. Cog-wheeling generally occurs when rigidity is superimposed on tremor. Rigidity may be measured in-clinic with the clinician physically manipulating the patient to assess signs and symptoms. In some experimental setups, rigidity can also be measured with an apparatus to detect the displacement for applied force. However, in a telehealth scenario, there is a need to accurately and reliably measure rigidity in a remote setting. Some example embodiments herein may therefore relate to a system and method for facilitating remote-based assessment of rigidity that may involve combining signals from sensors and video analytics obtained via a secure remote session with the patient.

In still further aspects relating to remote patient monitoring, some example embodiments may be configured to effectuate a closed-loop, sensor-based AI-driven exercise training platform that may be implemented by way of an integrative telehealth application. Such embodiments advantageously leverage the principle that exercise regimen involving balance training as part of a physical routine can provide additional benefits for patients with balance/gait-related disorders on top of the benefits exercising itself already brings. Whereas exercises that involve balance training may be taught by a teacher/instructor in a face-to-face setting, where the teacher can manipulate the trainee's gesture in addition to offering visual and verbal instructions, example embodiments herein may involve a remote learning and real-time patient monitoring session for facilitating an AI-driven, network-based remote exercising arrangement. Additionally, where patients with movement disorders such as PD often report difficulties with everyday tasks such as buttoning, brushing, writing, etc., example embodiments may be configured to provided individualized training tailored to the patient based on AI integration in order to enable the experience of a personal trainer with focused attention and real-time corrective measures for gesture training.

Additional details with respect to the various constituent components of the digital health infrastructure 1212, example external devices 1206 comprising clinician programmer devices 1208, patient controller devices 1210 and/or third-party devices 1211, as well as various interactions involving the network-based entities and the end points (also referred to as edge devices) will be set forth immediately below in order to provide an example architectural framework wherein one or more of the foregoing embodiments may be implemented and/or augmented according to the teachings herein.

Figure 1A:
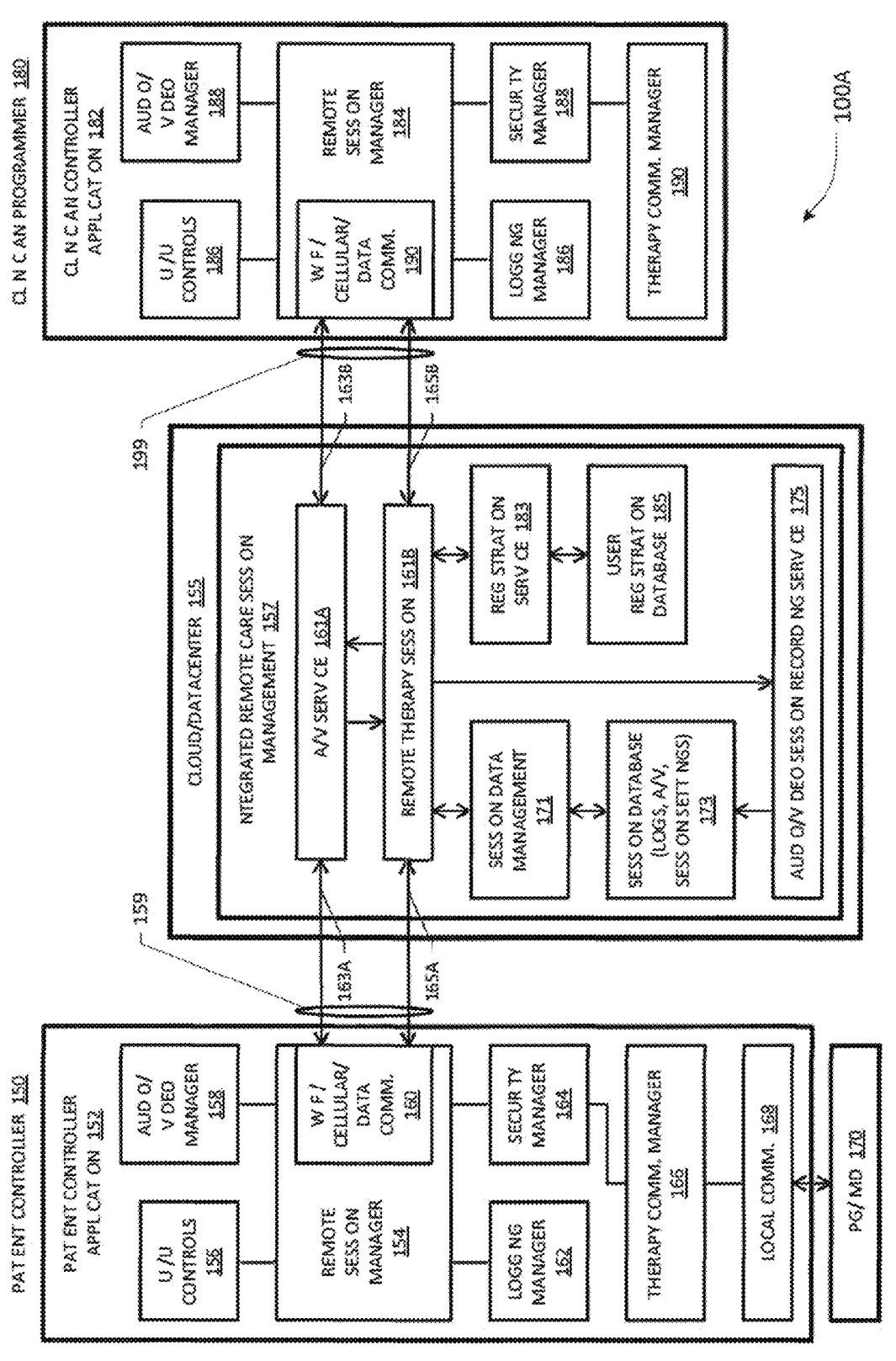
FIG. 1A depicts an example architecture of a system configured to support remote patient therapy as part of an integrated remote care service session in a virtual clinic environment that may be deployed in a cloud-centric digital health implementation according to one or more embodiments of the present patent disclosure.

Turning to FIG. 1A, depicted therein is an example architecture of a system configured to support remote patient therapy as part of an integrated remote care service session in a virtual clinic environment that may be deployed in a cloud-centric digital health implementation for purposes of an embodiment of the present patent disclosure. As used herein, a "remote care system" may describe a healthcare delivery system configured to support a remote care service over a network in a communication session between a patient and a clinician wherein telehealth or telemedicine applications involving remote medical consultations as well as therapy applications involving remote programming of the patient's IMD may be launched via a unified application interface facilitated by one or more network entities (e.g., as a virtual clinic platform). In some arrangements, a remote care system may also include a remote patient monitoring system and/or a remote healthcare provisioning system without the involvement of a clinician. In still further arrangements, a remote care system may include one or more AI-based expert systems or agents, e.g., involving supervised learning, that may be deployed in a network to provide or otherwise augment the capabilities of a system to effectuate enhanced healthcare solutions relating to diagnosis, remote learning, therapy selection, as well as facilitate network-based solutions for enhancing patients' overall well-being. In some aspects, remote care therapy may involve any care, programming, or therapy instructions that may be provided by a doctor, a medical professional or a healthcare provider, and/or their respective authorized agents, collectively referred to as a "clinician", using a suitable clinician device, with respect to the patient's IMD, wherein such therapy instructions may be mediated, proxied or otherwise relayed by way of a controller device associated with the patient. As illustrated, example remote care system 100A may include a plurality of patient controller devices exemplified by patient controller device 150 and a plurality of clinician programmer devices exemplified by a clinician programmer device 180 (also referred to as a clinician programmer or clinician device) that may interact with a network-based infrastructure via respective communication interfaces. Example patient and clinician devices may each include a corresponding remote care service application module, e.g., a patient controller application 152 and a clinician programmer/controller application 182, executed on a suitable hardware/software platform for supporting a remote care service that may be managed by a network entity 155. In some embodiments, example network entity 155 may comprise a distributed datacenter or cloud-based service infrastructure (e.g., disposed in a public cloud, a private cloud, or a hybrid cloud, involving at least a portion of the Internet) operative to host a remote care session management service 157. In one arrangement, patient controller application 152 and clinician programmer application 182 may each include a respective remote session manager 154, 184 configured to effectuate or otherwise support a corresponding communication interface 160, 190 with network entity 155 using any known or heretofore unknown communication protocols and/or technologies. In one arrangement, interfaces 160, 190 are each operative to support an audio/video or audiovisual (AV) channel or session 163A, 163B and a remote therapy channel or session 165A, 165B, respectively, with an AV communication service 161A and a remote therapy session service 161B of the remote care session management service 157 as part of a common bi-directional remote care session 159, 199 established therewith. In one arrangement, patient controller application 152 and clinician programmer application 182 may each further include or otherwise support suitable graphical user interfaces (GUIs) and associated controls 156, 186, as well as corresponding AV managers 158, 188, each of which may be interfaced with respective remote session managers 154, 184 for purposes of one or more embodiments of the present disclosure as will be set forth in additional detail further below. Remote care session manager 154 of the patient controller application 152 and remote care session manager 184 of the clinician programmer application 182 may each also be interfaced with a corresponding data logging manager 162, 186 for purposes of still further embodiments of the present disclosure. In one arrangement, remote care session manager 154 of patient controller application 152 is further interfaced with a security manager 164, which may be configured to facilitate secure or trusted communication relationships with the network entity 155. Likewise, remote care session manager 184 of clinician programmer application 182 may also be interfaced with a security manager 188 that may be configured to facilitate secure or trusted communication relationships with the network entity 155. Each security manager 164, 188 may be interfaced with a corresponding therapy communication manager 166, 190 with respect to facilitating secure therapy communications between the clinician programmer device 180 and the patient controller device 150. Therapy communication manager 166 of the patient controller application 152 may also interface with a local communication module 168 operative to effectuate secure communications with the patient's IPG/IMD 170 using a suitable short-range communications technology or protocol. In still further arrangements, security managers 164, 188 of patient controller and clinician programmer applications 152, 182 may be configured to interface with the remote care session management service 157 to establish trusted relationships between patient controller device 150, clinician programmer device 180 and IPG/IMD 170 based on the exchange of a variety of parameters, e.g., trusted indicia, cryptographic keys and credentials, etc.

In one arrangement, the integrated remote care session management service 157 may include a session data management module 171, an AV session recording service module 175 and a registration service module 183, as well as suitable database modules 173, 185 for storing session data and user registration data, respectively. In some arrangements, at least part of the session data may include user-characterized data relating to AV data, therapy settings data, network contextual data, and the like, for purposes of still further embodiments of the present patent disclosure.

Skilled artisans will realize that example remote care system architecture 100A set forth above may be advantageously configured to provide both telehealth medical consultations as well as therapy instructions over a communications network while the patient and the clinician/provider are not in close proximity of each other (e.g., not engaged in an in-person office visit or consultation). Accordingly, in some embodiments, a remote care service of the present disclosure may form an integrated healthcare delivery service effectuated via a common application user interface that not only allows healthcare professionals to use electronic communications to evaluate and diagnose patients remotely but also facilitates remote programming of the patient's IPG/IMD for providing appropriate therapy, thereby enhancing efficiency as well as scalability of a delivery model. Additionally, example remote care system architecture 100A may be configured to effectuate various other aspects relating to remote learning, remote patient monitoring, etc., as noted above. Further, an implementation of example remote care system architecture 100A may involve various types of network environments deployed over varying coverage areas, e.g., homogenous networks, heterogeneous networks, hybrid networks, etc., which may be configured or otherwise leveraged to provide patients with relatively quick and convenient access to diversified medical expertise that may be geographically distributed over large areas or regions, preferably via secure communications channels in some example embodiments as will be set forth in detail further below.

Figure 1B:
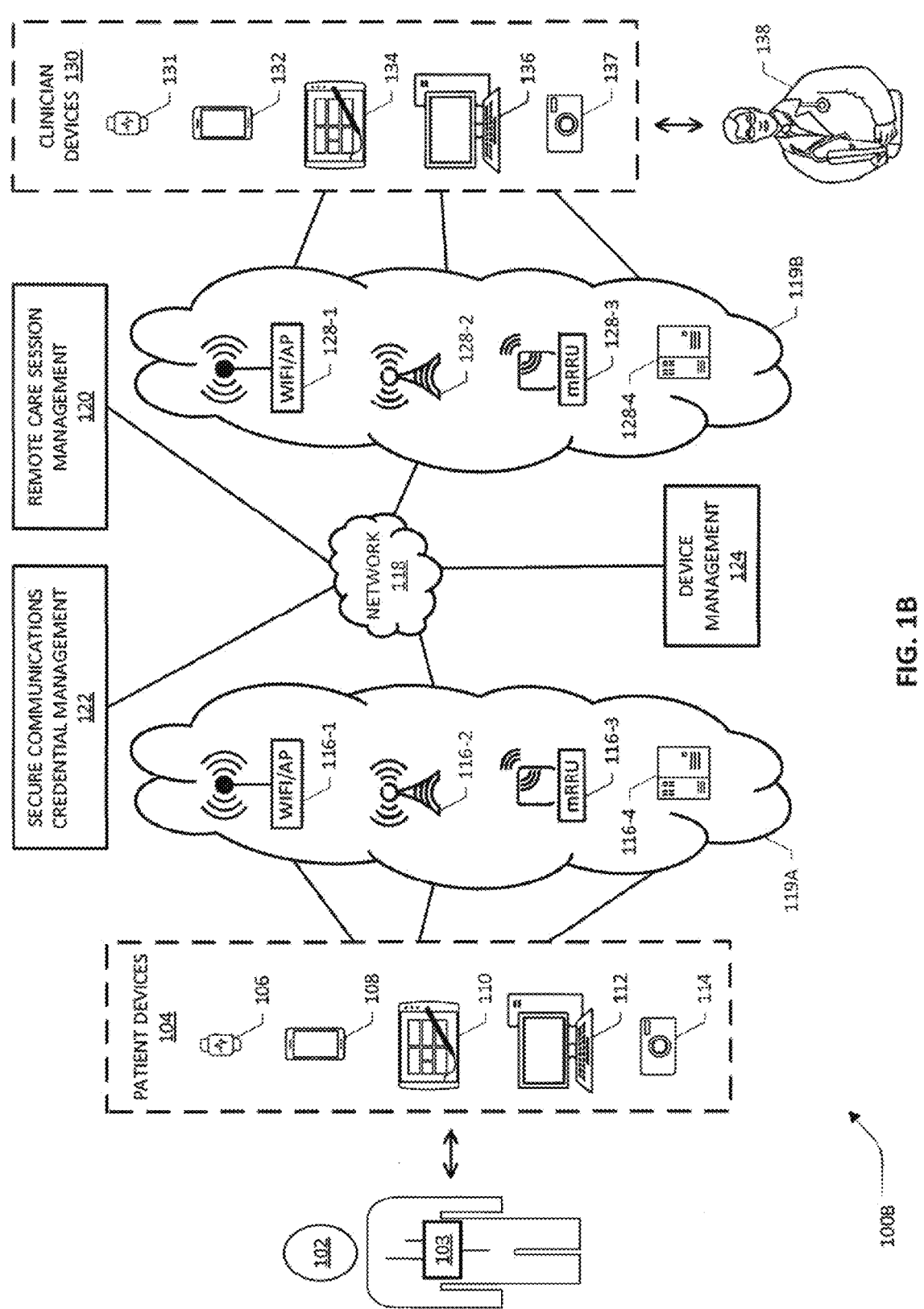
FIG. 1B depicts an example network environment wherein the remote care service architecture of FIG. 1A may be implemented according to a representative embodiment.

FIG. 1B depicts an example network environment 100B wherein the remote care service architecture of FIG. 1A may be implemented according to some embodiments. Illustratively, example network environment 100B may comprise any combination or sub-combination of a public packet-switched network infrastructure (e.g., the Internet or worldwide web, also sometimes referred to as the "cloud", as noted above), private packet-switched network infrastructures such as Intranets and enterprise networks, health service provider network infrastructures, and the like, any of which may span or involve a variety of access networks, backhaul and core networks in an end-to-end network architecture arrangement between one or more patients, e.g., patient(s) 102, and one or more authorized clinicians, healthcare professionals, or agents thereof, e.g., generally represented as caregiver(s) or clinician(s) 138. Example patient(s) 102, each having one or more suitable implantable and/or NIMI devices, e.g., IMD 103, may be provided with a variety of corresponding external devices for controlling, programming, otherwise (re)configuring the functionality of respective implantable device(s) 103, as is known in the art. Such external devices associated with patient(s) 102, referred to herein as patient devices 104, which are representative of patient controller device 150 shown in FIG. 1A, may comprise a variety of user equipment (UE) devices, tethered or untethered, that may be configured to engage in remote care sessions involving telehealth and/or therapy sessions according to some embodiments described below. By way of example, patient devices 104 may comprise commercial off-the-shelf (COTS) equipment or proprietary portable medical/healthcare devices (non-COTS), which may be configured to execute a therapy/digital healthcare application program or "app", wherein various types of communications relating to control, therapy/diagnostics, and/or device file management may be effectuated for purposes of some embodiments. Accordingly, example patient devices 104 may include, in addition to proprietary medical devices, devices such as smartphones, tablets or phablets, laptops/desktops, handheld/palmtop computers, wearable devices such as smart glasses and smart watches, personal digital assistant (PDA) devices, smart digital assistant devices, etc., any of which may operate in association with one or more virtual assistants, smart home/office appliances, smart TVs, external/auxiliary AV equipment, virtual reality (VR), mixed reality (MR) or augmented reality (AR) devices, and the like, which are generally exemplified by wearable device(s) 106, smartphone(s) 108, tablet(s)/phablet(s) 110, computer(s) 112, and AV equipment 114. As such, example patient devices 104 may include various types of communications circuitry or interfaces to effectuate wired or wireless communications, short-range and long-range radio frequency (RF) communications, magnetic field communications, etc., using any combination of technologies, protocols, and the like, with external networked elements and/or respective implantable devices 103 corresponding to patient(s) 102. With respect to networked communications, patient devices 104 may be configured, independently or in association with one or more digital/virtual assistants, smart home/premises appliances and/or home networks, to effectuate mobile communications using technologies such as Global System for Mobile Communications (GSM) radio access network (GRAN) technology, Enhanced Data Rates for Global System for Mobile Communications (GSM) Evolution (EDGE) network (GERAN) technology, 4G Long Term Evolution (LTE) technology, Fixed Wireless technology, $5^{th}$ Generation Partnership Project (5GPP or 5G) technology, Integrated Digital Enhanced Network (IDEN) technology, WiMAX technology, various flavors of Code Division Multiple Access (CDMA) technology, heterogeneous access network technology, Universal Mobile Telecommunications System (UMTS) technology, Universal Terrestrial Radio Access Network (UTRAN) technology, AII-IP Next Generation Network (NGN) technology, as well as technologies based on various flavors of IEEE 802.11 protocols (e.g., WiFi), and other access point (AP)-based technologies and microcell-based technologies involving small cells, femtocells, picocells, etc. Further, some embodiments of patient devices 104 may also include interface circuitry for effectuating network connectivity via satellite communications. Where tethered UE devices are provided as patient devices 104, networked communications may also involve broadband edge network infrastructures based on various flavors of Digital Subscriber Line (DSL) architectures and/or Data Over Cable Service Interface Specification (DOCSIS)https://en.wikipedia.org/wiki/Help: IPA/English-compliant Cable Modem Termination System (CMTS) network architectures (e.g., involving hybrid fiber-coaxial (HFC) physical connectivity). Accordingly, by way of illustration, an edge/access network portion 119A is exemplified with elements such as WiFi/AP node(s) 116-1, macro-cell node(s) 116-2 such as eNB nodes, gNB nodes, etc., microcell nodes 116-3 (e.g., including micro remote radio units or RRUs, etc.) and DSL/CMTS node(s) 116-4.

In similar fashion, clinicians and/or clinician agents 138 may be provided with a variety of external devices for controlling, programming, otherwise (re)configuring or providing therapy operations with respect to one or more patients 102 mediated via respective implantable device(s) 103, in a local therapy session and/or telehealth/remote therapy session, depending on implementation and use case scenarios. External devices associated with clinicians/agents 138, referred to herein as clinician devices 130, which are representative of clinician programmer device 180 shown in FIG. 1A, may comprise a variety of UE devices, tethered or untethered, similar to patient devices 104, that may be configured to engage in telehealth and/or remote care therapy sessions as will be set forth in detail further below. Clinician devices 130 may therefore also include non-COTS devices as well as COTS devices generally exemplified by wearable device(s) 131, smartphone(s) 132, tablet(s)/phablet(s) 134, computer(s) 136 and external/auxiliary AV equipment 137, any of which may operate in association with one or more virtual assistants, smart home/office appliances, VR/AR/MR devices, and the like. Further, example clinician devices 130 may also include various types of network communications circuitry or interfaces similar to that of personal devices 104, which may be configured to operate with a broad range of technologies as set forth above. Accordingly, an edge/access network portion 119B is exemplified as having elements such as WiFi/AP node(s) 128-1, macro/microcell node(s) 128-2 and 128-3 (e.g., including micro remote radio units or RRUs, base stations, eNB/gNB nodes, etc.) and DSL/CMTS node(s) 128-4. It should therefore be appreciated that edge/access network portions 119A, 119B may include all or any subset of wireless/wireline communication infrastructures, technologies and protocols for effectuating data communications with respect to an example embodiment of the present disclosure.

In one arrangement, a plurality of network elements or nodes may be provided for facilitating an integrated remote care therapy service involving one or more clinicians 138 and one or more patients 102, wherein such elements are hosted or otherwise operated by various stakeholders in a service deployment scenario depending on implementation, e.g., including one or more public clouds, private clouds, or any combination thereof as previously noted. According to some example embodiments, a remote care session management node or platform 120 may be provided, generally representative of the network entity 157 shown in FIG. 1A, preferably disposed as a cloud-based element coupled to network 118, that is operative in association with a secure communications credentials management node 122 and a device management node 124, to facilitate a virtual clinic platform whereby a clinician may advantageously engage in a telehealth session and/or a remote care therapy session with a particular patient via a common application interface and associated AV and therapy controls, as will be described further below.

Figure 2:
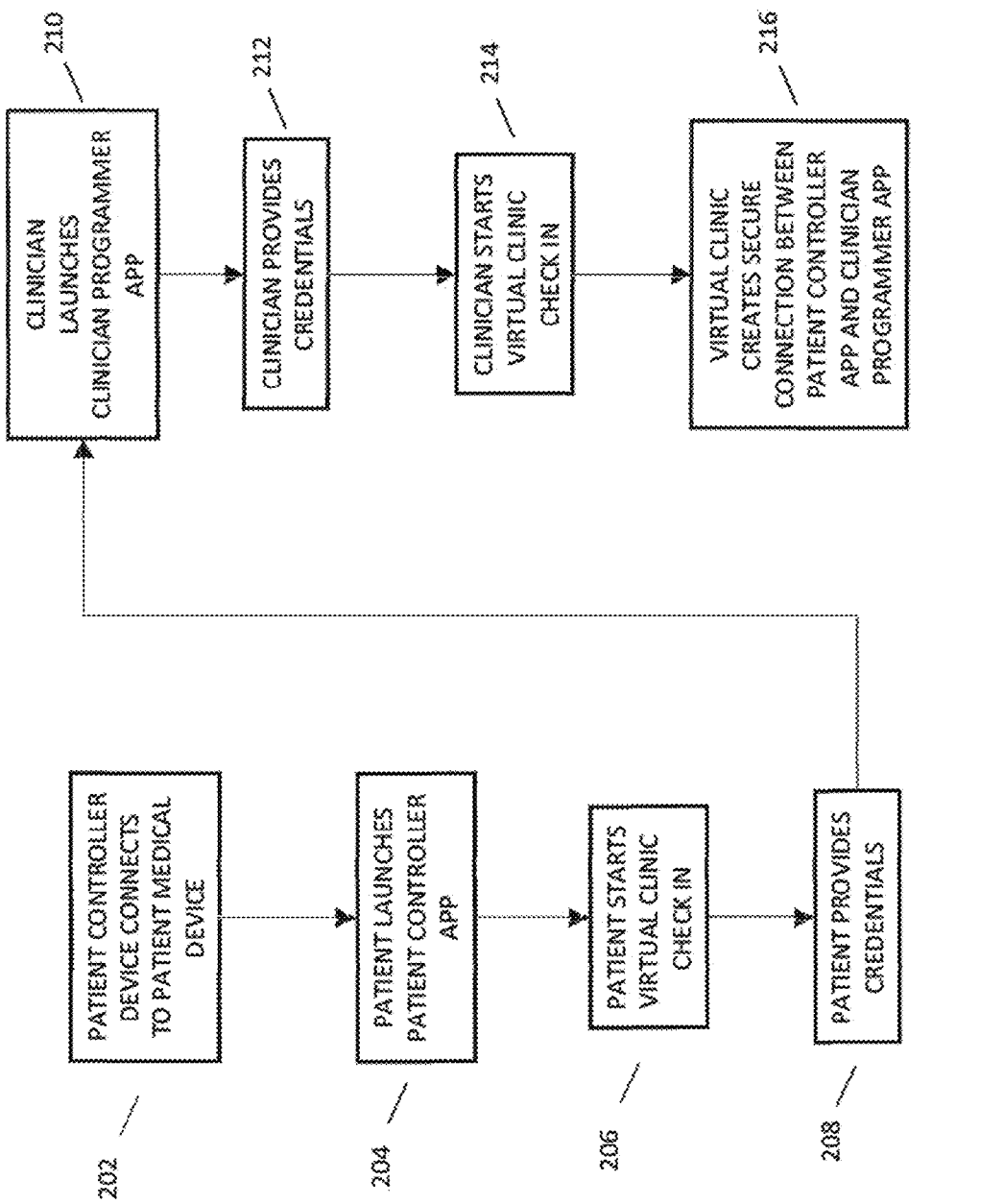
FIG. 2 depicts a flowchart illustrative of blocks, steps and/or acts that may be (re)combined in one or more arrangements with or without additional flowcharts of the present disclosure for facilitating remote care therapy in a secure network environment for purposes of some embodiments.

FIG. 2 depicts a flowchart for establishing a remote programing or virtual clinic session according to known processes. Additional details regarding establishment of remote programming or virtual clinic sessions may be found in U.S. Pat. No. 10,124,177 which is incorporated herein by reference. Although some details are described herein regarding establishment of a virtual clinic/remote program-ming session, any suitable methods may be employed according to other embodiments. At block 202, the patient controller device connects to the patient's medical device. For example, the patent controller device may establish a BLUETOOTH communication session with the patient's implantable pulse generator. At block 204, the patient launches the patient controller app on the patient controller device. At block 206, the patient starts a virtual clinic check in process by selecting a suitable GUI component of the patient controller app. In block 208, the patient may provide patient credentials. At block 210, the clinician launches the clinician programmer app on the clinician programmer device. In block 212, the clinician provides credentials. At block 214, the clinician checks into the virtual clinic to communicate with the patient. At block 216, the virtual clinic infrastructure establishes a secure connection between the patient controller app and clinician programmer app to conduct communications. Known cybersecurity features may be applied to establish the secure connection including using PKI processes, encryption processes, authentication processes, etc. Biometric data and other data may also be employed to enhance the secure nature of the communica-tion session by validating user identities and authorization. Upon establishment, the communications may include audio and video communications between the patient and the clinician. Also, the clinician may conduct remote program-ming of the patient's medical device during the session while communicating with the patient.

Figure 3:
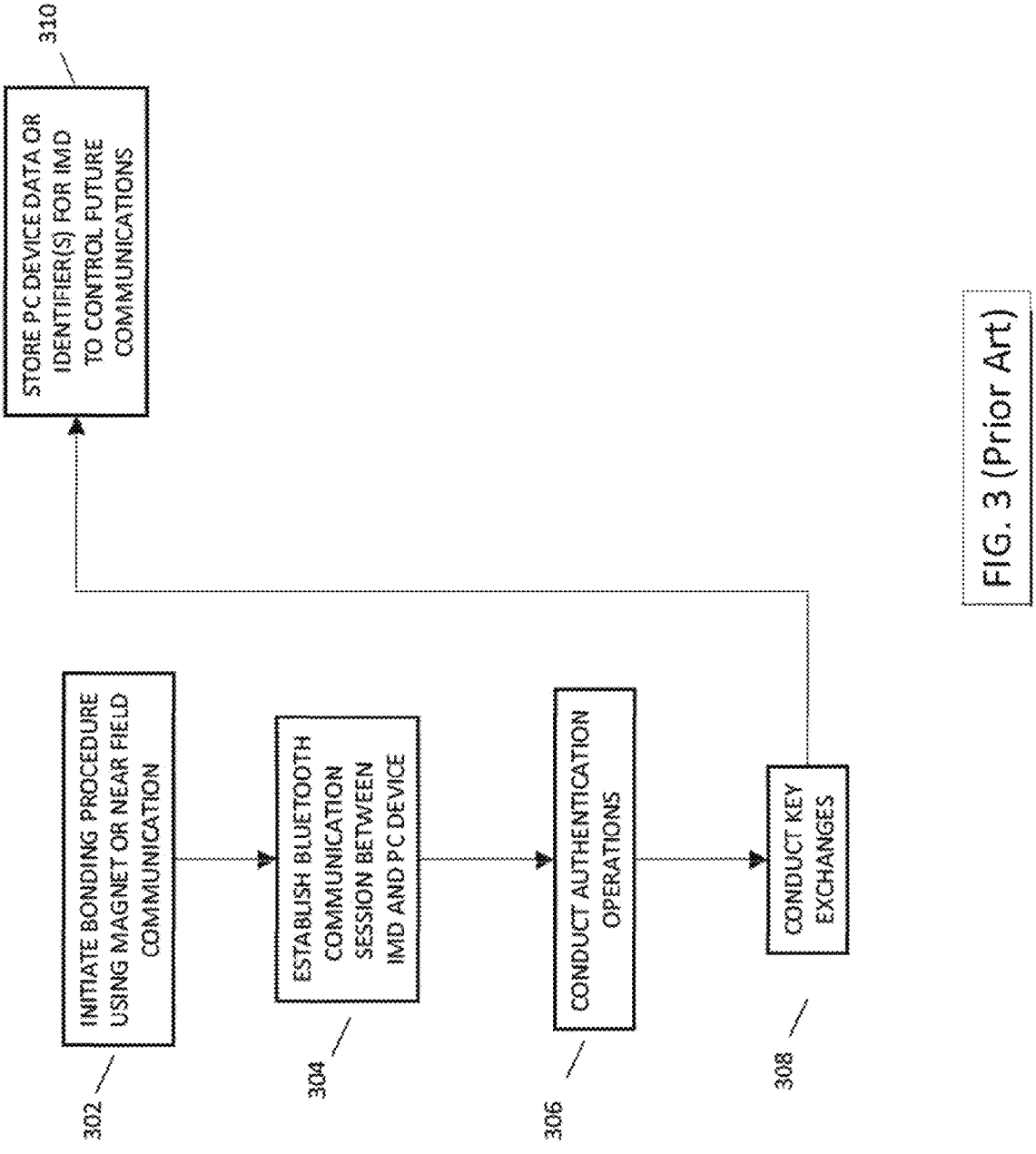
FIG. 3 depicts a flowchart illustrative of blocks, steps and/or acts that may be implemented for establishing a communication session with an implantable medical device.

FIG. 3 depicts a flowchart illustrative of known blocks, steps and/or acts that may be implemented for establishing a communication session with an implantable medical device. Additional details regarding establishing a commu-nication session with an implantable medical device may be found in U.S. Pat. No. 11,007,370 which is incorporated herein by reference. Although example operations are described in FIG. 3, any suitable methods of securing communication between a PC device and a patient medical device may be employed as appropriate for a given patient therapy. At block 302, a bonding procedure is initiated to establish a trusted relationship between the implantable medical device or other medical device of the patient and a patient controller device. The bonding procedure may be initiated by using a magnet to activate a Hall sensor in the medical device. Alternatively, near field communication (e.g., inductive coupling) may be employed to initiate the bonding procedure. The use of a magnetic or inductive coupling provides a degree of physical access control to limit the possibility of unauthorized devices from commu-nicating with the patient's medical device. That is, a device that attempts to obtain authorization to communicate must be brought into physical proximity with the patient at a time that is controlled by the patient thereby reducing the possibility of unauthorized devices from improperly gaining the ability to communicate with the patient's device. At block 304, a communication session is established between the patient's medical device and the patient's controller (PC) device. For example, a BLUETOOTH communication ses-sion may be established. At block 306, authentication opera-tions are conducted. For example, known credentials, PKI, encryption, and other cybersecurity operations may be applied between the patient's medical device and the PC device to determine whether the PC device should be allowed to conduct communications with the patient's medi-cal device. At block 308, encryption key data may be exchanged between devices for future communications. At block 310, other PC identifiers or data may be stored in IMD to control future communications. Upon establishment of a trusted relationship between the patient's medica device and a PC device, the PC device may be used to conduct remote programming session. The remote programming sessions may also be subjected to cybersecurity methods such as the use of credentials, PKI, encryption, etc.

Figure 4A:
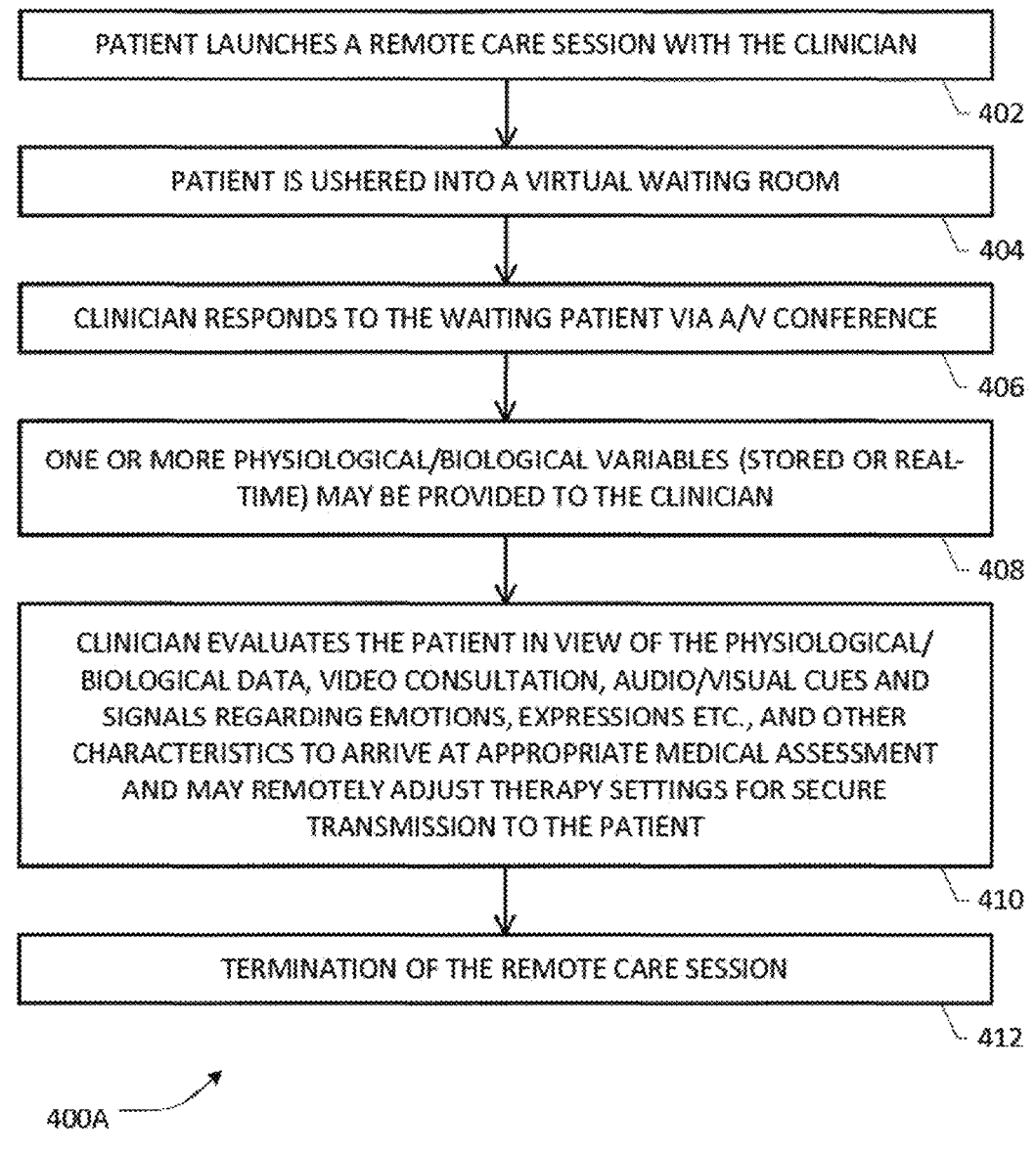

FIGS. 4A and 4B depicts flowcharts illustrative of a remote care scenario involving an example digital health network architecture wherein an integrated remote care session may be established between a patient and a clinician operating respective controller devices that support suitable graphical user interfaces (GUIs) for facilitating a therapy session, an audio/visual (AV) communication session, or a combination of both, for purposes of some example embodi-ments of the present disclosure. As will be set forth further below, patient controller and/or clinician programmer devices may be provided with appropriate application soft-ware to effectuate suitable GUIs on respective devices for facilitating a remote care session including a secure AV session/channel and a therapy session/channel as part of a common application interface that can support telehealth/telemedicine applications, remote monitoring, remote therapy, remote learning, data logging, etc. Process flow 400A of FIG. 4A may commence with a patient launching an integrated digital health application executing on the patient controller/device to initiate a secure communications chan-nel with a remote clinician (block 402), e.g., by selecting a "Remote Care" option from a pull-down menu, clicking on an icon on the UI display screen, or via a voice command, etc. In one embodiment, the patient may be ushered into a virtual waiting room, which may be realized in a UI screen window of the patient/clinician device (block 404). At block 406, the clinician responds to the waiting patient, e.g., via a secure AV communication channel of the remote care ses-sion. At block 408, one or more physiological/biological data of the patient (stored or real-time) may be provided to the clinician via secure communications. In some embodi-ments, one or more digital keys of the clinician and/or the patient may be employed to secure communications. At block 410, the clinician evaluates the patient in view of the physiological/biological data, telemedicine/video consulta-tion, audio/visual cues and signals regarding patient's facial expressions, hand movement/tremors, walking, gait, ambu-latory status/stability, and other characteristics to arrive at appropriate medical assessment. Depending on such tele-health consultation/evaluation, the clinician may remotely adjust stimulation therapy settings for secure transmission to the patient device, which may be securely transmitted via encrypted communications. In a further scenario, a remote clinician proxy or agent may be executed at or in association with the patient controller/device upon launching a remote session, wherein the proxy/agent is operative to effectuate or otherwise mediate the transmission of any therapy settings to the patient's IMD, either in real-time or at some point in the future depending upon programmatic control. After completing the requisite therapy and consultative communications, the remote care session may be terminated, e.g., either by the clinician and/or the patient, as set forth at block 412.

Process flow 400B of FIG. 4B is illustrative of an embodiment of a high level scheme for delivering healthcare to a patient via an integrated remote care session. At block 422, a remote care session between a controller device associated with the patient and a programmer device associated with a clinician may be established, wherein the clinician and the patient are remotely located with respect to each other and the remote care session includes an AV communication session controlled by one or more AN controls provided at the patient controller device and the clinician programmer device. At block 424, various telehealth consultation services may be provided to the patient by the clinician based on interacting with the patient via the AV communication channel of the remote care session as previously noted. Responsive to determining that the patient requires remote therapy, one or more remote programming instructions may be provided to the patient's IMD via a remote therapy session or channel of the remote care session with the patient controller device while the AV communication session is maintained (block 426).

Skilled artisans will recognize that some of the blocks, steps and/or acts set forth above may take place at different entities and/or different times (i.e., asynchronously), and possibly with intervening gaps of time and/or at different locations. Further, some of the foregoing blocks, steps and/or acts may be executed as a process involving just a single entity (e.g., a patient controller device, a clinician programmer device, or a remote session manager operating as a virtual clinic, etc.), or multiple entities, e.g., as a cooperative interaction among any combination of the end point devices and the network entities. Still further, it should be appreciated that example process flows may be interleaved with one or more sub-processes comprising other IMD<=>patient or IMD<=>clinician interactions (e.g., local therapy sessions) as well as virtual clinic<=>patient or virtual clinic<=>clinician interactions (e.g., remote patient monitoring, patient/clinician data logging, remote learning, rigidity assessment, context-aware kinematic and auditory analysis, etc., as will be set forth further below). Accordingly, skilled artisans will recognize that example process flows may be altered, modified, augmented or otherwise reconfigured for purposes of some embodiments herein.

In one implementation, an example remote care session may be established between the patient controller device and the clinician programmer device after the patient has activated a suitable GUI control provided as part of a GUI associated with the patient controller device and the clinician has activated a corresponding GUI control provided as part of a virtual waiting room displayed on a GUI associated with the clinician programmer device. In another arrangement, remote programming instructions may be provided to the patient's IMD via the remote therapy session only after verifying that remote care therapy programming with the patient's IMD is compliant with regulatory requirements of one or more applicable local, regional, national, supranational governmental bodies, non-governmental agencies, and international health organizations. In a still further variation, various levels of remote control of a patient's controller and its hardware by a clinician programmer device may be provided. For example, suitable GUI controls may be provided at the clinician programmer device for remotely controlling a camera component or an auxiliary AV device associated with the patient controller device by interacting with a display of the patient's image on the screen of the clinician programmer device, e.g., by pinching, swiping, etc., to pan to and/or zoom on different parts of the patient in order to obtain high resolution images. Additional embodiments and/or further details regarding some of the foregoing variations with respect to providing remote care therapy via a virtual clinic may be found in the following U.S. patent applications, publications and/or patents: (i) U.S. Patent Application Publication No. 2020/0398062, entitled "SYSTEM, METHOD AND ARCHITECTURE FOR FACILITATING REMOTE PATIENT CARE"; (ii) U.S. Patent Application Publication No. 2020/0402656, entitled "UI DESIGN FOR PATIENT AND CLINICIAN CONTROLLER DEVICES OPERATIVE IN A REMOTE CARE ARCHITECTURE"; (iii) U.S. Patent Application Publication No. 2020/0402674, entitled "SYSTEM AND METHOD FOR MODULATING THERAPY IN A REMOTE CARE ARCHITECTURE"; and (iv) U.S. Patent Application Publication No. 2020/0398063, entitled "DATA LABELING SYSTEM AND METHOD OPERATIVE WITH PATIENT AND CLINICIAN CONTROLLER DEVICES DISPOSED IN A REMOTE CARE ARCHITECTURE", each of which is hereby incorporated by reference herein.

Figures 5A, 5B:
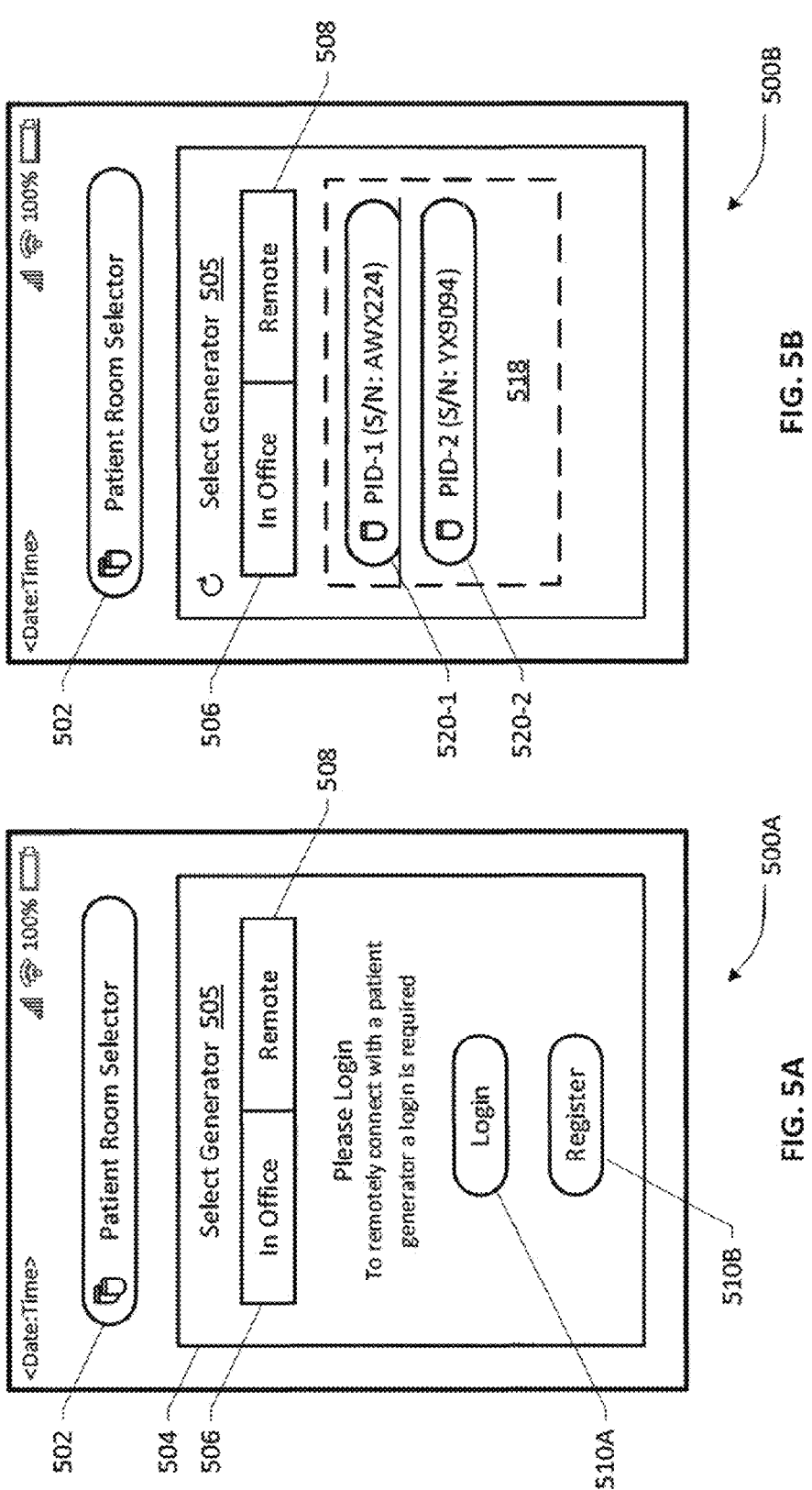
FIGS. 5A and 5B depict representations of an example user interface and associated dialog boxes provided with a clinician programmer device for selecting different therapy applications and/or service modes for purposes of some embodiments of the present disclosure.

FIGS. 5A and 5B depict representations of an example user interface and associated dialog boxes or windows provided with a clinician programmer device, e.g., as a touch screen display of device 180 exemplified in FIG. 1A, for selecting different therapy applications and/or service modes in an integrated remote care service application for purposes of some example embodiments of the present disclosure. In one arrangement, example GUI(s) of the clinician device may be optimized or resized to provide a maximum display window for the presentation of a patient's image during remote therapy while allowing the presentation of appropriate remote care therapy session and setting controls as well as AV communication session controls such that high quality video/image information may be advantageously obtained by the clinician, which can help better evaluate the patient's response(s) to the applied/modified therapy settings and/or the clinician's verbal, textual, and/or visual requests to perform certain tasks as part of remote monitoring by the clinician. Accordingly, in some example embodiments, the clinician device may be provided with one or more non-transitory tangible computer-readable media or modules having program code stored thereon for execution on the clinician device as part of or in association with a clinician programmer application for facilitating remote therapy and telehealth delivery in an integrated session having a common application interface that effectuates an optimized GUI display within the form factor constraints of the device. In one arrangement, a code portion may be provided for displaying a virtual waiting room identifying one or more patients, each having at least one IMD/NIMI device configured to facilitate a therapy, wherein the virtual waiting room is operative to accept input by the clinician to select a patient to engage in a remote care session with a patient controller device of the selected patient. A code portion may be provided for displaying one or more audio controls and one or more video controls for facilitating an AV communication session associated with the remote care session after the remote care session is established between the patient controller device and the clinician programmer device. Various AV session controls may be represented as suitable icons, pictograms, etc. as part of a GUI display of the at the clinician programmer device, roughly similar to the GUI presentation at a patient controller device as will be set forth below. Further, example video controls may be configured to effectuate a first display window (i.e., a clinician image window) and a second display window (i.e., a patient image window) on the GUI display for respectively presenting an image of the clinician and an image of the patient. A code portion may be provided for displaying one or more remote care therapy session and setting controls, wherein the one or more remote care therapy setting controls are operative to facilitate one or more adjustments with respect to the patient's IMD settings in order to provide appropriate therapy to the patient as part of a remote therapy component of the remote care session. Preferably, the code portion may be configured to provide the AV communication session controls as well as the remote care therapy session and setting controls in a consolidated manner so as to facilitate the display thereof in a minimized overlay panel presented on the GUI screen while maximizing the second display window such that an enlarged presentation of the patient's image is effectuated during the remote care session. In some embodiments, the remote care therapy setting controls may be configured to expand into additional graphical controls for further refining one or more IMD settings depending on the implementation and/or type(s) of therapy applications the clinician programmer device is configured with. For example, such remote care therapy setting controls may comprise icons or pictograms corresponding to, without limitation, one or more of a pulse amplitude setting control, a pulse width setting control, a pulse frequency setting control, a pulse delay control, a pulse repetition parameter setting control, a biphasic pulse selection control, a monophasic pulse section control, a tonic stimulation selection control, a burst stimulation selection control, a lead selection control, an electrode selection control, and a "Stop Stimulation" control, etc., at least some of which may be presented in a set of hierarchical or nested pull-down menus or display windows. In still further embodiments, a code portion may be provided for displaying one or more data labeling buttons as part of the GUI display of the clinician programmer device, similar to the GUI embodiments of the patient controller device described above, wherein the one or more data labeling buttons are operative to accept input by the clinician corresponding to a subjective characterization of AV quality, therapy response capture, and other aspects of therapy programming during the remote care session.

GUI screen 500A depicted in FIG. 5A is representative of a "login" screen that may be presented at the clinician device upon launching the clinician programmer application for facilitating a clinician to select a service mode, e.g., a remote care service mode or an in-office care service mode. A "Patient Room" selector menu option 502 may be operative to present a "generator" window 505 that includes an "In-Office" patient option 506 or a "Remote" patient option 508, wherein the activation or selection of the Remote patient option 508 effectuates one or more windows or dialog boxes for facilitating user login, registration, authentication/authorization and other security credentialing services, as exemplified by windows 510A, 510B. Upon validation, the clinician may be presented with a virtual waiting room 518 identifying one or more remote patients as exemplified in GUI screen 500B of FIG. 5B. Each remote patient may be identified by one or more identifiers and/or indicia, including, without limitation, personal identifiers, respective IMD identifiers, therapy identifiers, etc., subject to applicable privacy and healthcare laws, statutes, regulations, and the like. Accordingly, in some embodiments such identification indicia may comprise, inter alia, patient names, images, thumbnail photos, IMD serial numbers, etc., collectively referred to as Patient ID (PID) information, as illustrated by PID-1 520-1 and PID-2 520-2. In some embodiments, a time indicator may be associated with each remote patient, indicating how long a remote patient has been "waiting" (e.g., the time elapsed since launching a remote care session from his/her controller device). In some embodiments, a priority indicator may also be associated with remote patients, wherein different priorities may be assigned by an intervening human and/or AI/ML-based digital agent. Furthermore, patients may have different types of IMDs to effectuate different therapies and a patient may have more than one IMD in some cases. An example embodiment of virtual waiting room 518 may therefore include a display of any combination of remote patients and their respective IMDs by way of suitably distinguishable PIDs having various pieces of information, wherein the PIDs may be individually selectable by the clinician for establishing a remote care session that may include remote therapy programming or just telehealth consultations.

Figure 6:
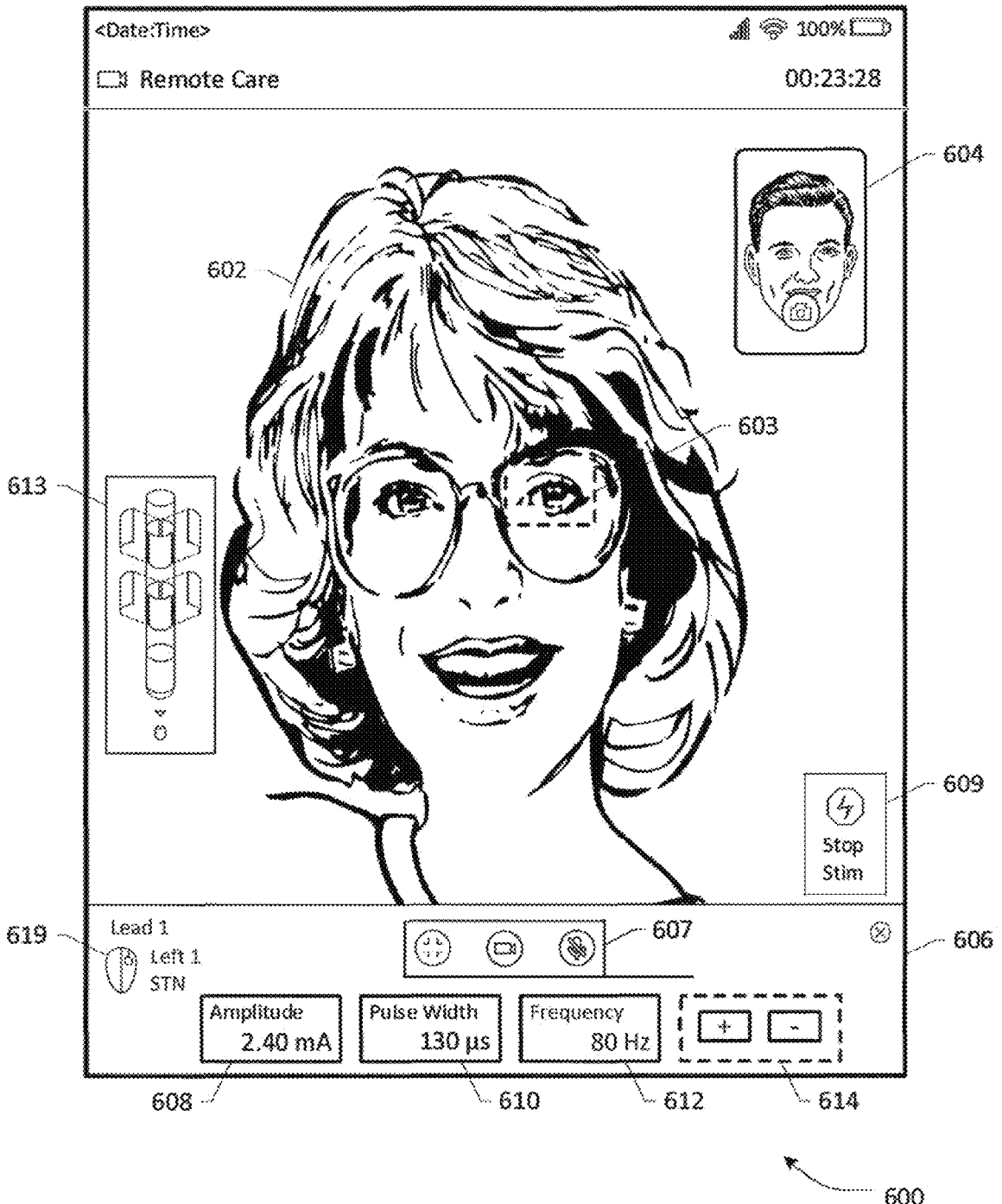
FIG. 6 depicts a representation of an example user interface provided with a clinician programmer device for facilitating controls with respect to an AV communication session and a remote therapy session in an integrated remote care service application for purposes of some embodiments of the present disclosure.

FIG. 6 depicts a representation of an example user interface of a clinician programmer device with additional details for facilitating graphic controls with respect to an AV communication session and a remote therapy session in an integrated remote care service application for purposes of some embodiments of the present disclosure. As illustrated, GUI screen 600 is representative of a display screen that may be presented at the clinician device after establishing that remote therapy programming is to be effectuated for a selected remote patient. In accordance with some of the embodiments set forth herein, GUI screen 600 may be arranged so that the patient's video image is presented in an optimized or resized/oversized display window 602 while the clinician's video image is presented in a smaller display window 604 along with a compact control icon panel 606 to maximize the level of detail/resolution obtained in the patient's image. Furthermore, the smaller clinician image window 604 may be moved around the UI screen by "dragging" the image around the viewing area of the patient's image window 602 to allow more control of the positioning of the display windows so that the patient's image view is unimpeded and/or optimized at a highest possible resolution. It will be appreciated that such high level video quality is particularly advantageous in obtaining more reliable cues with respect to the patient's facial expressions, moods, gestures, eye/iris movements, lip movements, hand movements tremors, jerks, twitches, spasms, contractions, or gait, etc., that may be useful in diagnosing various types of motor/neurological disorders, e.g., Parkinson's disease. As will be seen further below, a remote data logging platform may be configured to store the AV data of the sessions for facilitating model building and training by appropriate AI/ML-based expert systems or digital assistants for purposes of further embodiments of the present patent disclosure.

Control panel window 606 may include a sub-panel of icons for AV and/or remote care session controls, e.g., as exemplified by sub-panel 607 in addition to a plurality of icons representing remote therapy setting controls, e.g., pulse amplitude control 608, pulse width control 610, pulse frequency control 612, increment/decrement control 614 that may be used in conjunction with one or more therapy setting controls, along with a lead selection indication icon 619. Skilled artisans will recognize that the exact manner in which a control panel window may be arranged as part of a consolidated GUI display depends on the therapy application, IMD deployment (e.g., the number of leads, electrodes per lead, electrode configuration, etc.), and the like, as well as the particular therapy settings. Additional control icons relating to stimulation session control, e.g., Stop Stimulation icon 609, as well as any other icons relating to the remote care session such as lead/electrode selection 613, may be presented as minimized sub-panels adjacent to the control panel window 606 so as not to compromise the display area associated with the patient' image display 602.

In some embodiments, a code portion may be provided as part of the clinician programmer application to effectuate the transitioning of GUI screen 600 to or from a different sizing (e.g., resizing) in order to facilitate more expanded, icon-rich GUI screen in a different display mode. For example, a client device GUI screen may be configured such that the clinician's and patient's video images are presented in smaller windows, respectively, with most of the rest of the display region being populated by various icons, windows, pull-down menus, dialog boxes, etc., for presenting available programming options, lead selection options, therapy setting options, electrode selection options, and the like, in a more elaborate manner. In some embodiments, the video UI panels and related controls associated with clinician/patient video image windows may be moved around the GUI screen by "dragging" the images around the display area. Still further, the positioning of the video UI panels and related controls associated with clinician/patient video image windows may be stored as a user preference for a future UI setup or configuration that can be instantiated or initialized when the controller application is launched. As can be appreciated, it is contemplated that a clinician device may be configured to be able to toggle between multiple GUI display modes by pressing or otherwise activating zoom/collapse buttons that may be provided on respective screens.

In some further embodiments, a clinician device may be provided with additional functionality when utilizing or operating in the resized display GUI screen mode. By way of a suitable inputting mechanism at the clinician device, e.g., by pressing or double-tapping a particular portion of the patient's image, or by scrolling a cursor or a pointing device to a particular potion of the patient's image, etc., the clinician can remotely control the AV functionality of the patient controller device, e.g., a built-in camera or an auxiliary AV device such as AV equipment, in order to zoom in on and/or pan to specific portions of the patient's body in order to obtain close-up images that can enable better diagnostic assessment by the clinician. In such embodiments, zooming or enlarging of a portion of the patient's image, e.g., eye portion, may be effectuated by either actual zooming, i.e., physical/optical zooming of the camera hardware, or by way of digital zooming (i.e., by way of image processing).

In some embodiments, both optical and digital zooming of a patient's image may be employed. In still further embodiments, the patient controller device and/or associated AV equipment may be panned and/or tilted to different portions of the patient's body to observe various motor responses and/or conditions while different programming settings may be effectuated in a remote therapy session, e.g., shaking and tremors, slowed movement or bradykinesia, balance difficulties and eventual problems standing up, stiffness in limbs, shuffling when walking, dragging one or both feet when walking, having little or no facial expressions, drooling, muscle freezing, difficulty with tasks that are repetitive in nature (like tapping fingers or clapping hands or writing), difficulty in performing everyday activities like buttoning clothes, brushing teeth, styling hair, etc.

In still further embodiments, separate remote therapy session intervention controls (e.g., pause and resume controls) may be provided in addition to stimulation start and termination controls, which may be operative independent of or in conjunction with AV communication session controls, in a manner similar to example patient controller GUI embodiments set forth hereinbelow. Still further, data labeling buttons or controls may also be provided in a separate overlay or window of GUI screen 600 (not shown in FIG. 6) to allow or otherwise enable the clinician to provide different types of data labels for the AV data and therapy settings data for purposes of some embodiments of the present patent disclosure.

Figure 7:
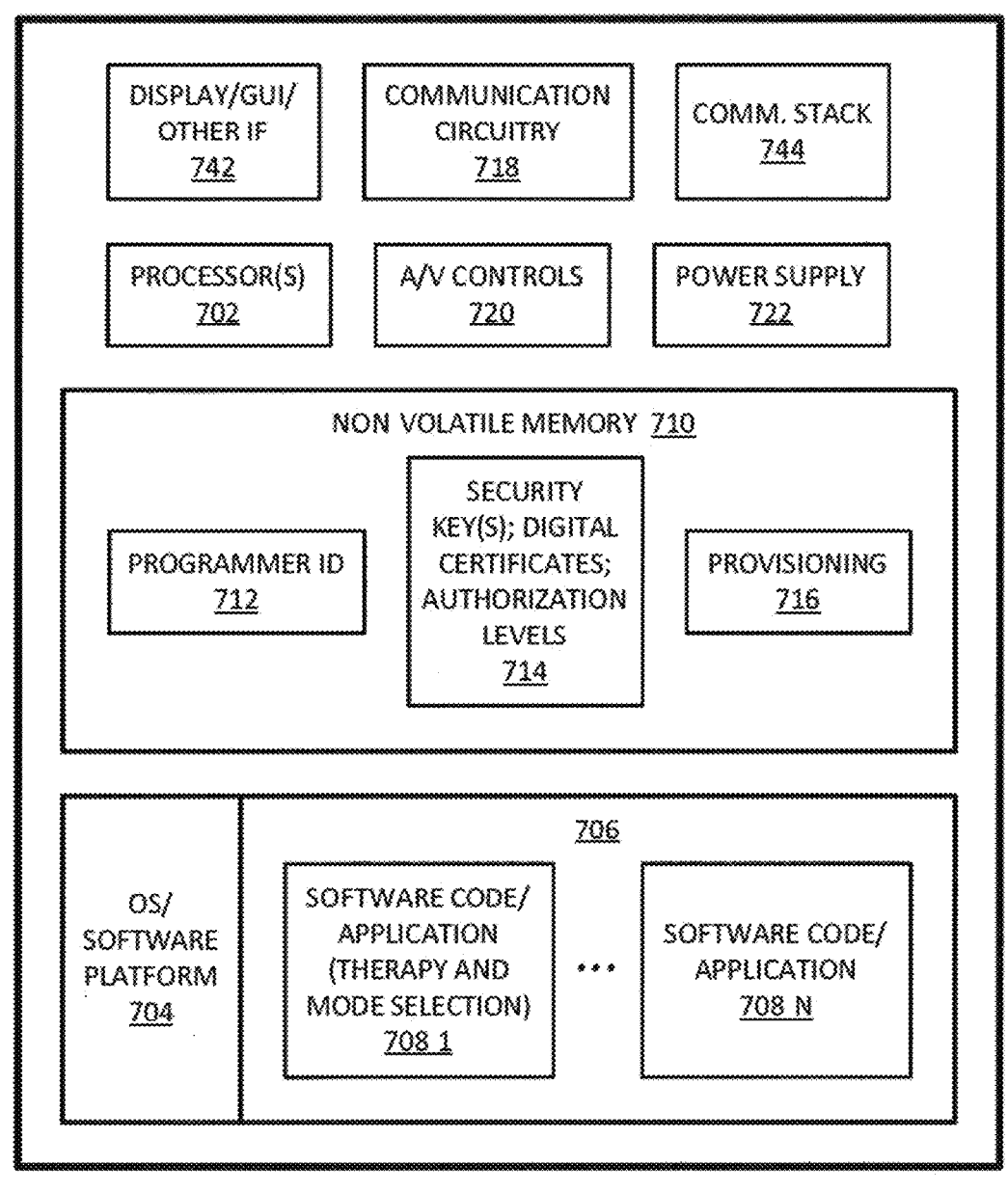
FIG. 7 depicts a block diagram of an external device that may be configured as a clinician programmer device, a patient controller device or an authorized third-party device operative in a digital health network architecture for purposes of some embodiments of the present disclosure.

FIG. 7 depicts a block diagram of a generalized external edge device operative in a digital health network architecture for purposes of some embodiments of the present disclosure. For example, depending on configuration and/or modality, external device 700 may be representative of a clinician programmer device, a patient controller device, or a delegated device operated by an agent of a patient or a clinician having subordinate levels of privilege authorization with respect to remote therapy and monitoring operations. Further, external device 700 may be a COTS device or non-COTS device as previously noted. Still further, external device 700 may be a device that is controlled and managed in a centralized enterprise device management system (EDMS), also referred to as a mobile/medical device management system (MDMS), which may be associated with the manufacturer of the IMDs and associated therapy application components in some embodiments (e.g., as an intranet implementation, an extranet implementation, or internet-based cloud implementation, etc.), in order to ensure that only appropriately managed/provisioned devices and users are allowed to engage in communications with IMDs with respect to monitoring the devices and/or providing therapy to patients using approved therapy applications. Still further, external device 700 may be a device that is not controlled and managed in such a device management system. Accordingly, it will be realized that external device 700 may comprise a device that may be configured in a variety of ways depending on how its functional modality is implemented in a particular deployment.

Example external device 700 may include one or more processors 702, communication circuitry 718 and one or more memory modules 710, operative in association with one or more OS platforms 704 and one or more software applications 708-1 to 708-K depending on configuration, cumulatively referred to as software environment 706, and any other hardware/software/firmware modules, all being powered by a power supply 722, e.g., battery. Example software environment 706 and/or memory 710 may include one or more persistent memory modules comprising program code or instructions for controlling overall operations of the device, inter alia. Example OS platforms may include embedded real-time OS systems, and may be selected from, without limitation, iOS, Android, Chrome OS, Blackberry OS, Fire OS, Ubuntu, Sailfish OS, Windows, Kai OS, eCos, LynxOS, QNX, RTLinux, Symbian OS, VxWorks, Windows CE, MontaVista Linux, and the like. In some embodiments, at least a portion of the software applications may include code or program instructions operative as one or more medical/digital health applications for effectuating or facilitating one or more therapy applications, remote monitoring/testing operations, data capture and logging operations, trial therapy applications, etc. Such applications may be provided as a single integrated app having various modules that may be selected and executed via suitable drop-down menus in some embodiments. However, various aspects of the edge device digital healthcare functionalities may also be provided as individual apps that may be downloaded from one or more sources such as device manufactures, third-party developers, etc. By way of illustration, application 708-1 is exemplified as digital healthcare app configured to interoperate with program code stored in memory 710 to execute various operations relative to device registration, mode selection, remote/test/trial programming, therapy selection, security applications, and provisioning, etc., as part of a device controller application.

In some embodiments of external device 700, memory modules 710 may include a non-volatile storage area or module configured to store relevant patient data, therapy settings, and the like. Memory modules 710 may further include a secure storage area 712 to store a device identifier (e.g., a serial number) of device 700 used during therapy sessions (e.g., local therapy programming or remote therapy programming). Also, memory modules 710 may include a secure storage area 714 for storing security credential information, e.g., one or more cryptographic keys or key pairs, signed digital certificates, etc. In some arrangements, such security credential information may be specifically operative in association with approved/provisioned software applications, e.g., therapy/test application 708-1, which may be obtained during provisioning. Also, a non-volatile storage area 716 may be provided for storing provisioning data, validation data, settings data, metadata etc. Communication circuitry 718 may include appropriate hardware, software and interfaces to facilitate wireless and/or wireline communications, e.g., inductive communications, wireless telemetry or M2M communications, etc. to effectuate IMD communications, as well as networked communications with cellular telephony networks, local area networks (LANs), wide area networks (WANs), packet-switched data networks, etc., based on a variety of access technologies and communication protocols, which may be controlled by the digital healthcare application 708-1 depending on implementation.

For example, application 708-1 may include code or program instructions configured to effectuate wireless telemetry and authentication with an IMD/NIMI device using a suitable M2M communication protocol stack which may be mediated via virtual/digital assistant technologies in some arrangements. By way of illustration, one or more bi-directional communication links with a device may be effectuated via a wireless personal area network (WPAN) using a standard wireless protocol such as Bluetooth Low Energy (BLE), Bluetooth, Wireless USB, Zigbee, Near-Field Communications (NFC), WiFi (e.g., IEEE 802.11 suite of protocols), Infrared Wireless, and the like. In some arrangements, bi-directional communication links may also be established using magnetic induction techniques rather than radio waves, e.g., via an induction wireless mechanism. Alternatively and/or additionally, communication links may be effectuated in accordance with certain healthcare-specific communications services including, Medical Implant Communication Service (MICS), Wireless Medical Telemetry Service (MTS), Medical Device Radiocommunications Service (MDRS), Medical Data Service (MDS), etc. Accordingly, regardless of which type(s) of communication technology being used, external device 700 may be provided with one or more communication protocol stacks 744 operative with hardware, software and firmware (e.g., forming suitable communication circuitry including transceiver circuitry and antenna circuitry where necessary, which may be collectively exemplified as communication circuitry 718 as previously noted) for effectuating appropriate short-range and long-range communication links for purposes of some example embodiments herein.

External device 700 may also include appropriate audio/video controls 720 as well as suitable display(s) (e.g., touch screen), camera(s), microphone, and other user interfaces (e.g., GUIs) 742, which may be utilized for purposes of some example embodiments of the present disclosure, e.g., facilitating user input, initiating IMD/network communications, mode selection, therapy selection, etc., which may depend on the aspect(s) of a particular digital healthcare application being implemented.

FIG. 8 depicts a block diagram illustrating additional details pertaining to a patient controller device operative in a digital health network architecture for purposes of some embodiments of the present disclosure. Example patient controller device 800 may be particularly configured for securely packaging and transmitting patient data to an external entity, e.g., a clinician programmer device and/or a network entity disposed in the digital health network in order to facilitate remote monitoring, AI/ML model training, and the like. Consistent with the description provided above with respect to a generalized edge device, patient controller device 800 may be provided with a patient controller application 802 configured to run in association with a suitable device hardware/software environment 850 effectuated by one or more processor and memory modules 806, one or more OS platforms 808, and one or more persistent memory modules 816 comprising program code or instructions for controlling overall operations of the device, inter alia. Example OS platforms may include a variety of embedded real-time OS systems as noted previously. In one implementation, a secure file system 810 that can only be accessed by the patient controller application 802 may be provided, wherein one or more patient data files 812 may be stored in a packaged encrypted form for secure transmission for purposes of some embodiments herein. Also, patient controller application 802 may include a therapy manager 824 operative to facilitate remote and/or non-remote therapy applications and related communications using one or more communication interfaces, e.g., interface 834 with an IPG/IMD 804 and network communications interface 836 with a network entity, as previously noted. A logging manager 830 associated with therapy manager 824 may be provided for logging data. A security manager 828 associated with therapy manager 824 may be provided for facilitating secure or trusted communications with a network entity in some embodiments. A therapy communication manager 832 may be provided for facilitating secure therapy communications between patient controller 800 and a clinician programmer (not shown in this FIG.). Therapy communication manager 832 may also be interfaced with local communication interface 834 to effectuate secure communications with the patient's IPG/IMD 804 using a suitable short-range communications technology or protocol as noted previously.

In still further arrangements, suitable software/firmware modules 820 may be provided as part of patient controller application 802 to effectuate appropriate user interfaces and controls, e.g., A/V GUIs, in association with an audio/video manager 822 for facilitating therapy/diagnostics control, file management, and/or other input/output (I/O) functions. Additionally, patient controller 800 may include an encryption module 814 operative independently and/or in association or otherwise integrated with patient controller application 802 for dynamically encrypting a patient data file, e.g., on a line-by-line basis during runtime, using any known or heretofore unknown symmetric and/or asymmetric cryptography schemes, such as the Advanced Encryption Standard (AES) scheme, the Rivest-Shamir-Adleman (RSA) scheme, Elliptic Curve Cryptography (ECC), etc.

FIG. 9 depicts a block diagram illustrating additional details pertaining to a clinician programmer device operative in a digital health network architecture for purposes of some embodiments of the present disclosure. Similar to the example patient controller device 800 described above, example clinician programmer 900 may be particularly configured for facilitating secure transmission of patient data to an external entity, e.g., another clinician programmer device and/or a network entity disposed in the digital healthcare network in order to facilitate remote monitoring, AI/ML model training, and the like. A clinician programmer application 902 may be configured to run in association with a suitable device hardware/software environment 950 effectuated by one or more processor and memory modules 304, one or more OS platforms 906, and one or more persistent memory modules 914 comprising program code or instructions for controlling overall operations of the device, inter alia. As before, example OS platforms may include a variety of embedded real-time OS systems according to some embodiments. Further, a secure file system 908 may be provided in clinician programmer 900 that can only be accessed by the clinician programmer application 902, wherein one or more patient data files 310 (e.g., corresponding to one or more patients) may be stored in a packaged encrypted form, respectively, for purposes of some embodiments herein. In one implementation, clinician programmer application 902 may include a therapy manager 926 operative to facilitate remote and/or non-remote therapy applications and related communications using one or more communication interfaces, e.g., interface 924. For example, interface 924 may be configured to communicate with an IMD (not shown in this FIG.) using various short-range communication links with respect to in-person or in-clinic therapy according to some embodiments as previously noted. Likewise, example interface 924 may be configured to provide connectivity with wide-area networks for facilitating remote programming of an IMD and/or a telehealth session in some scenarios. A logging manager 928 associated with therapy manager 924 may be provided for logging data for respective patients. A security manager 930 associated with therapy manager 926 may be provided for facilitating secure or trusted communications with a network entity in some embodiments. A therapy communication manager 932 may be provided for facilitating secure therapy communications between clinician programmer 900 and a patient controller (not shown in this FIG.). Suitable software/firmware modules 920 may be provided as part of clinician programmer application 902 to effectuate appropriate user interfaces and controls, e.g., A/V GUIs, in association with an audio/video manager 922 for facilitating therapy/diagnostics control, file management, and/or other I/O functions as noted previously. Further, clinician programmer 900 may include an encryption module 912 similar to that of patient controller 800, wherein the encryption module 912 is operative in association and/or otherwise integrated with clinician programmer application 902 for encrypting a patient data file, e.g., dynamically on a line-by-line basis, during runtime using suitable techniques.

Figure 10:
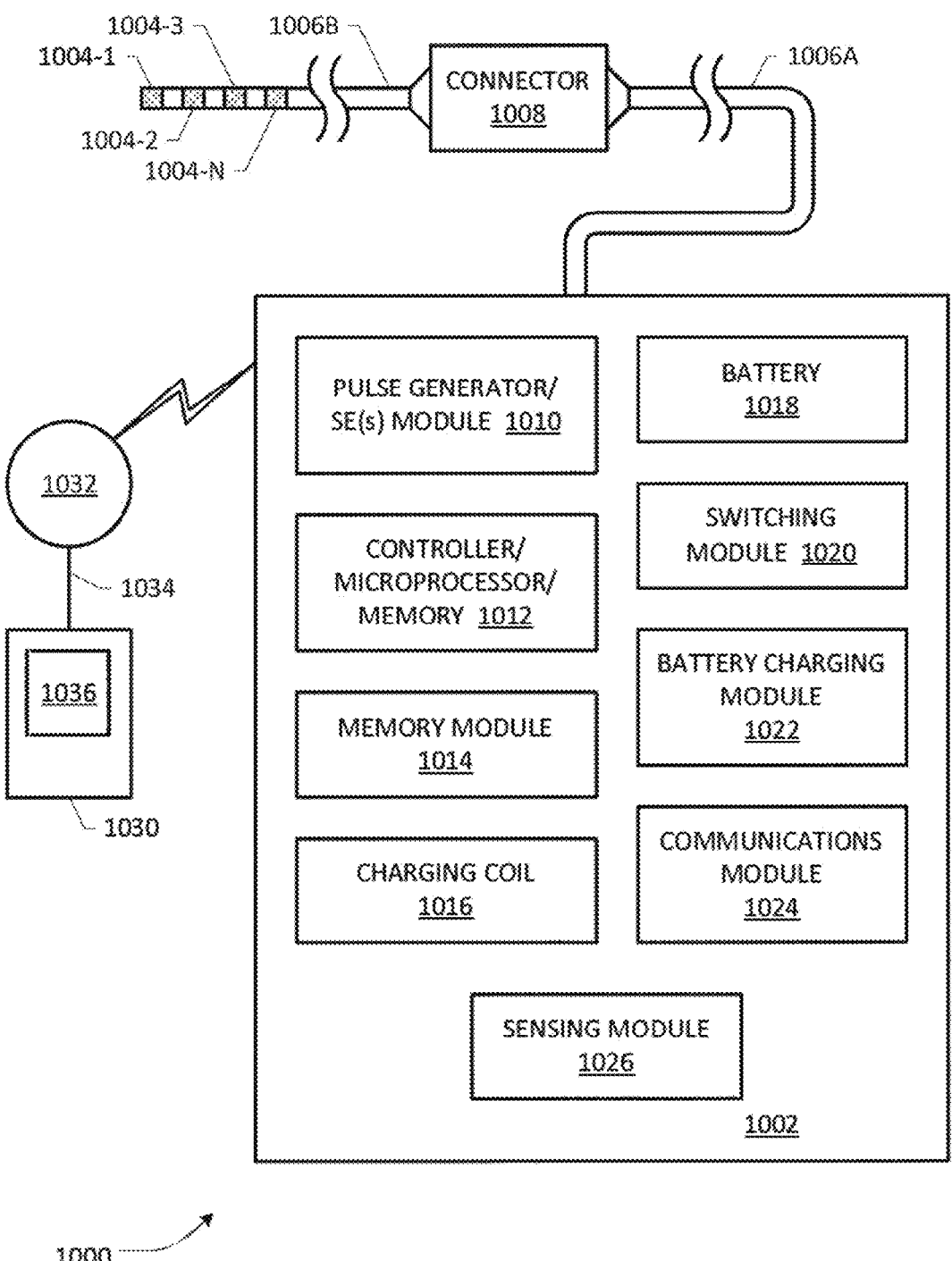
FIG. 10 depicts a block diagram of an IMD and associated system that may be configured for facilitating a remote care therapy application and/or a local therapy session for purposes of an example embodiment of the present disclosure.

FIG. 10 depicts a block diagram of an IMD and associated system that may be configured for facilitating a remote care therapy application and/or a local therapy session for purposes of an example embodiment of the present disclosure.

In general, therapy system 1000 may be adapted to generate electrical pulses to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, using an IMD or a trial IMD as previously noted. In one example embodiment, IMD 1002 may be implemented as having a metallic housing or can that encloses a controller/processing block or module 1012, pulse generating circuitry including or associated with one or more stimulation engines 1010, a charging coil 1016, a power supply or battery 1018, a far-field and/or near field communication block or module 1024, battery charging circuitry 1022, switching circuitry 1020, sensing circuitry 1026, a memory module 1014, and the like. IMD 1002 may include a diagnostic circuit module associated with a sensing module 1026 adapted to effectuate various diagnostics with respect to the state/condition of one or more stimulation electrodes and sensing electrodes of an implantable lead system as well as other bio/physiological sensors integrated or otherwise operative with IMD 1002. Controller/processor module 1012 typically includes a microcontroller or other suitable processor for controlling the various other components of IMD 1302. Software/firmware code, including digital healthcare application and encryption functionality, may be stored in memory 1014 of IMD 1002, and/or may be integrated with controller/processor module 1012. Other application-specific software code as well as associated storage components (not particularly shown in this FIG.) for execution by the microcontroller or processor 1012 and/or other programmable logic blocks may be provided to control the various components of the device for purposes of an embodiment of the present patent disclosure. As such, example IMD 1002 may be adapted to generate stimulation pulses according to known or heretofore known stimulation settings, programs, etc.

In one arrangement, IMD 1002 may be coupled (via a "header" as is known in the art, not shown in this FIG.) to a lead system having a lead connector 1008 for coupling a first component 1006A emanating from IMD 1002 with a second component 1006B that includes a plurality of electrodes 1004-1 to 1004-N, which may be positioned proximate to the patient tissue. Although a single lead system 1006A/1006B is exemplified, it should be appreciated that an example lead system may include more than one lead, each having a respective number of electrodes for providing therapy according to configurable settings. For example, a therapy program may include one or more lead/electrode selection settings, one or more sets of stimulation parameters corresponding to different lead/electrode combinations, respectively, such as pulse amplitude, stimulation level, pulse width, pulse frequency or inter-pulse period, pulse repetition parameter (e.g., number of times for a given pulse to be repeated for respective stimulation sets or "stimsets" during the execution of a program), etc. Additional therapy settings data may comprise electrode configuration data for delivery of electrical pulses (e.g., as cathodic nodes, anodic nodes, or configured as inactive nodes, etc.), stimulation pattern identification (e.g., tonic stimulation, burst stimulation, noise stimulation, biphasic stimulation, monophasic stimulation, and/or the like), etc. Still further, therapy programming data may be accompanied with respective metadata and/or any other relevant data or indicia.

As noted previously, external device 1030 may be deployed for use with IMD 1002 for therapy application, management and monitoring purposes, e.g., either as a patient controller device or a clinician programmer device.

In general, electrical pulses are generated by the pulse generating circuitry 1010 under the control of processing block 1012, and are provided to the switching circuitry 1020 that is operative to selectively connect to electrical outputs of IMD 1002, wherein one or more stimulation electrodes 1004-1 to 1004-N per each lead 1006A/B may be energized according to a therapy protocol, e.g., by the patient or patient's agent (via a local session) and/or a clinician (via a local or remote session) using corresponding external device 1030. Also, external device 1030 may be implemented to charge/recharge the battery 1018 of IPG/IMD 1002 (although a separate recharging device could alternatively be employed), to access memory 1012/1014, and/or to program or reprogram IMD 1002 with respect to one or more stimulation set parameters including pulsing specifications while implanted within the patient. In alternative embodiments, however, separate programmer devices may be employed for charging and/or programming the IMD device 1002 device and/or any programmable components thereof. Software stored within a non-transitory memory of the external device 1030 may be executed by a processor to control the various operations of the external device 1030, including facilitating encryption of patient data logged in or by IMD 1002 and extracted therefrom. A connector or "wand" 1034 may be electrically coupled to the external device 430 through suitable electrical connectors (not specifically shown), which may be electrically connected to a telemetry component 1032 (e.g., inductor coil, RF transceiver, etc.) at the distal end of wand 1034 through respective communication links that allow bi-directional communication with IMD 1002. Alternatively, there may be no separate or additional external communication/telemetry components provided with external device 1030 in an example embodiment that uses BLE or the like for facilitating bi-directional communications with IMD 1002.

In a setting involving in-clinic or in-person operations, a user (e.g., a doctor, a medical technician, or the patient) may initiate communication with IMD 1002. External device 1030 preferably provides one or more user interfaces 1036 (e.g., touch screen, keyboard, mouse, buttons, scroll wheels or rollers, or the like), allowing the user to operate IMD 1002. External device 1030 may be controlled by the user through user interface 1036, allowing the user to interact with IMD 1002, whereby operations involving therapy application/programming, coordination of patient data security including encryption, trial IMD data report processing, etc., may be effectuated.

FIGS. 11A-11H depict representations of an example user interface and associated dialog boxes or windows provided with a patient controller device for selecting different therapy applications and/or service modes and for facilitating controls with respect to an AV communication session as well as a remote therapy session in an integrated remote care service application for purposes of an embodiment of the present disclosure. In some example implementations, a patient controller device, e.g. device 150 shown in FIG. 1A, may be provided with one or more non-transitory tangible computer-readable media or modules having program code stored thereon for execution on the patient controller device as part of or in association with a patient controller application, e.g., application 152, for facilitating remote therapy and telehealth applications in an integrated session having a common application interface. A code portion may be provided for displaying a mode selector icon on a GUI display screen of the patient controller device, wherein the mode selector icon is operative for accepting input by the patient to launch a remote care session with a clinician having a clinician programmer device. A code portion may be provided for displaying one or more audio controls and one or more video controls for facilitating an AV communication session or channel associated with the remote care session after the remote care session is established between the patient controller device and the clinician programmer device. Such AV controls may be represented as suitable icons, pictograms, and the like, e.g., a video/camera icon for controlling a video channel, a microphone icon for controlling an audio channel, a speaker icon for volume control, as well as control icons operative with respect to picture-in-picture (PIP) display regions, and the like. For example, video controls may be operative to effectuate a first display window and a second display window on the GUI display for respectively presenting an image of the clinician and an image of the patient in a PIP display mode. Yet another code portion may be provided for displaying one or more remote care therapy session controls in an overlay panel presented on the GUI display, wherein the one or more remote care therapy session controls are operative with respect to starting and ending a remote care therapy session by the patient as well as facilitating a temporary intervention or interruption of the therapy session while the AV communication session is maintained. As noted above, an example remote care therapy session may involve providing one or more programming instructions to the patient's IMD as part of the remote care session, and temporary intervention of the remote therapy may only suspend the remote programming of the patient's IMD although the AV communication session between the patient and the clinician remains active. In further embodiments, one or more code portions may be provided with the patient controller application to effectuate tactile controls with respect to different portions, fields, regions or X-Y coordinates of an active GUI display window that may be configured to interact with the functionality of the AV controls and/or therapy session controls. In still further embodiments, one or more code portions may be provided with the patient controller application to effectuate one or more data labeling buttons, icons, pictograms, etc., as part of the GUI display of the patient controller device, wherein the one or more data labeling buttons are operative to accept input by the patient corresponding to a subjective characterization of audio and/or video quality of the AV communications and/or other aspects of the therapy by the patient during the remote care session. In still further embodiments, one or more code portions may be provided with the patient controller application to facilitate patient input/feedback with respect to a trial therapy or treatment involving an IMD or a NIMI device, which may be augmented with one or more data labeling buttons, icons, pictograms, etc., wherein the patient input/feedback data may be provided to a network-based AI/ML model for facilitating intelligent decision-making with respect to whether the IMD/NIMI device should be deployed in a more permanent manner (e.g., implantation) and/or whether a particular therapy setting or a set of settings, including context-sensitive therapy program selection, may need to be optimized or otherwise reconfigured.

Figure 11B:
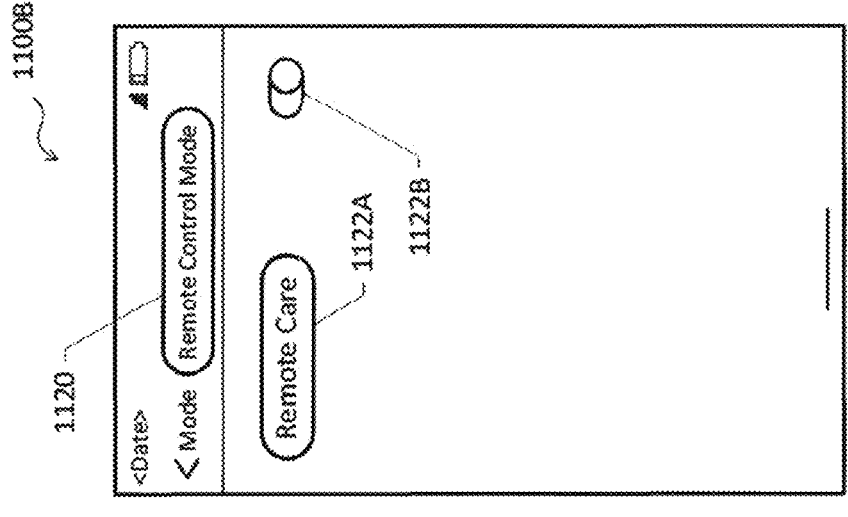
FIGS. 11A-11H depict representations of an example user interface and associated dialog boxes provided with a patient controller device for selecting different therapy applications and/or service modes and for facilitating controls with respect to an AV communication session and a remote
Figure 11A:
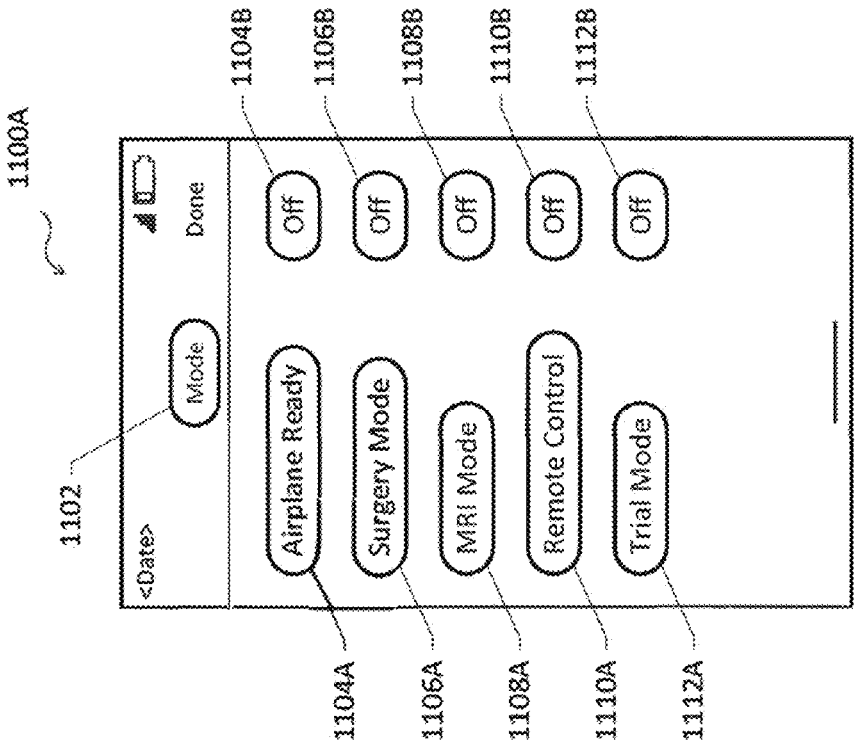

As illustrated, FIGS. 11A and 11B depict example GUI screens 1100A and 1100B of a patient controller device that allow user input with respect to various mode settings/selections, including the activation and deactivation of allowing a remote control programming (i.e., therapy) session to be conducted, e.g., in trial therapy mode, etc. GUI display screen 1100A includes a mode selector 1102 that may be activated to show various mode settings which in turn may be selected, enabled or otherwise activated by using associated tactile controls. For example, modes such as "Airplane Ready" 1104A, "Surgery Mode" 1106A, "MRI Mode" 1108A, "Remote Control Mode" 1110A, "Trial Mode" 1112A, each having a corresponding swipe button 1104B-1112B are depicted. GUI screen 1100B illustrates a display that may be effectuated upon selecting or allowing Remote Control 1120 wherein a Remote Care Mode 1122A may be selected or enabled for activating remote therapy using a corresponding swipe button 1122B. A patient may therefore selectively permit the activation of remote therapy (i.e., remote programming of the IMD), whereby if activated and connected, a clinician can securely change or modify the therapy settings of the patient's IMD by effectuating appropriate therapy setting controls and associated GUIs provided at a controller device as previously set forth.

Figure 11C:
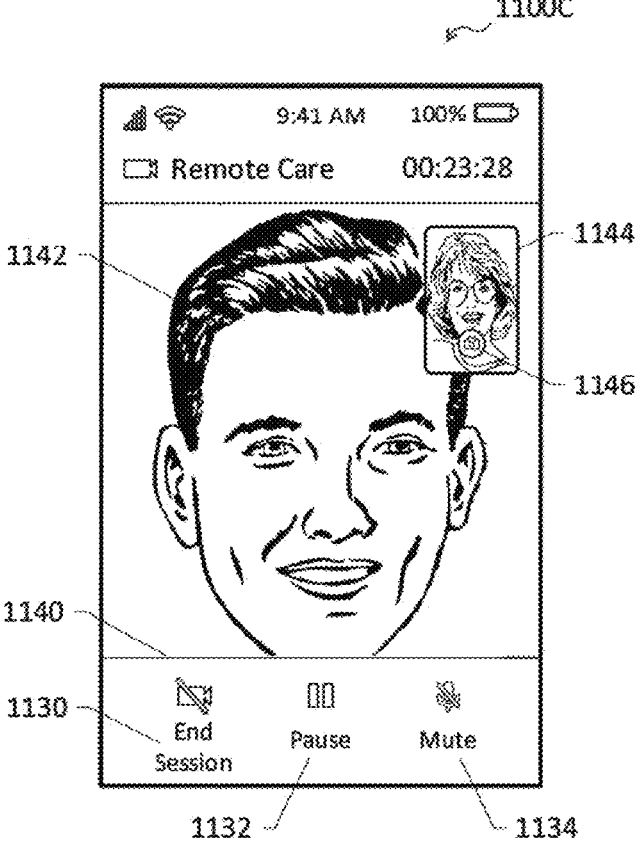

FIG. 11C depicts an example GUI display screen 11000 of the patient controller device during a remote care session, wherein an image of the selected clinician 1142 and an image of the patient 1144 may be presented in a PIP display region. In one display mode, the patient's image 1144 may be presented as a smaller offset or overlay image and the clinician's image 1142 may be presented as a main, larger image. In some embodiments, the patient image window 1144 may be moved around the UI screen by "dragging" the image around the viewing window allocated to the clinician image 1142. An image swap control 1146 may be provided to swap the PIP display regions in another display mode, whereby the patient's image 1144 may be presented as the main, larger image whereas the clinician's image 1142 may be presented in a smaller overlay window.

In some embodiments, a control panel 1140 may also be presented as part of the GUI screen 11000, wherein various AV communication session controls and remote therapy session controls may be displayed as suitable icons, pictograms, etc., in a consolidated GUI display as noted above. A video session icon 1130 may be activated/enabled or deactivated/disabled to selectively turn on or off the video channel of the session. A microphone icon 1134 may be activated/enabled or deactivated/disabled to selectively turn on or off the audio channel of the session. A pause/resume icon 1132 may be activated/enabled or deactivated/disabled to selectively pause or suspend, or resume the remote therapy session involving remote programming of the patient's IMD or any other remote digital healthcare application executing on the patient controller. In some implementations, activating or deactivating the video session icon 1130 may also be configured to turn on or off the remote therapy session. In some implementations, separate remote therapy session controls (e.g., start control, end control, etc. in addition to pause and resume controls) may be provided that are operative independent of the AV communication session controls. Still further, data labeling buttons may also be provided in a separate overlay or window of the GUI screen 11000 (not shown in this FIG.) to allow or otherwise enable the patent to input a subjective characterization of the AV data and therapy experience data as noted previously.

In a further embodiment of a digital health network architecture of the present patent disclosure, a digital health "app" may be installed on or downloaded to a patient controller device, e.g., patient controller device 1210 shown in FIG. 12, to permit a patient to report therapy outcomes for clinician review and analysis. An example of an existing digital health app that is available to patients in certain jurisdictions for reporting therapy outcomes to neurostimulation (including spinal cord stimulation) is the MYPATH™ app from Abbott (Plano, TX). The digital health app may use the network communications capabilities of patient controller device 1210 to communicate patient-reported data to patient report processing platform 1218. The clinician of a given patient may review the patient-reported data stored on platform 1218 to determine whether the therapy is working as expected and whether the patient requires reprogramming to optimize therapy. In some cases, the patient may provide the patient-reported data during a "trial" period which is used to evaluate the effectiveness of the therapy for the patient from a temporary external system before surgical implantation of the IMD. If the trial is successful, surgical implantation of the IMD may occur. Additionally or alternatively, the patient may provide the outcome data after surgical implantation of the IMD to allow monitoring of the patient's condition and response to the therapy to continue on an ongoing basis.

Figure 11D:
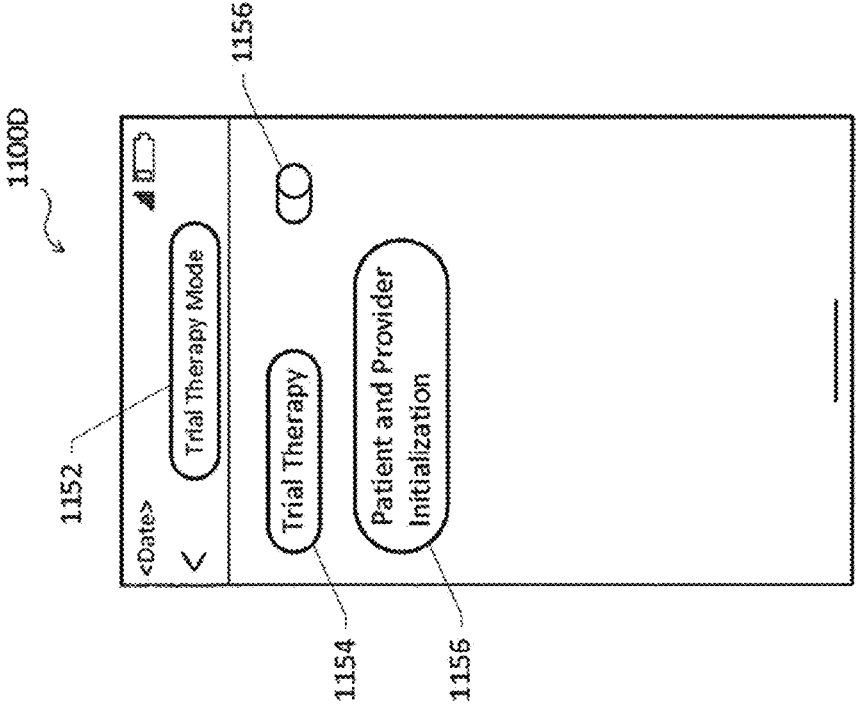
Figure 11H:
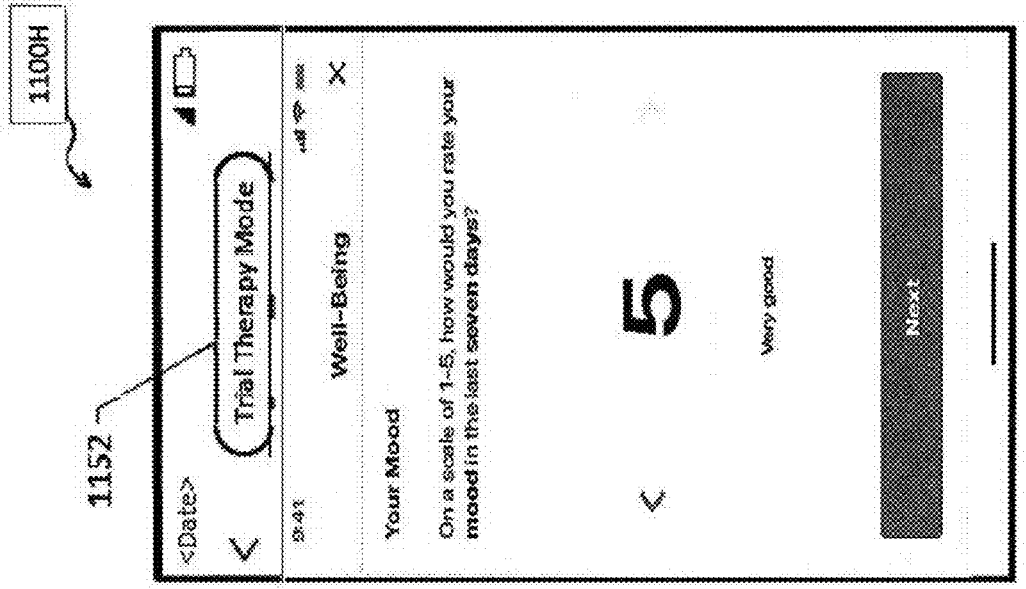
Figure 11E:
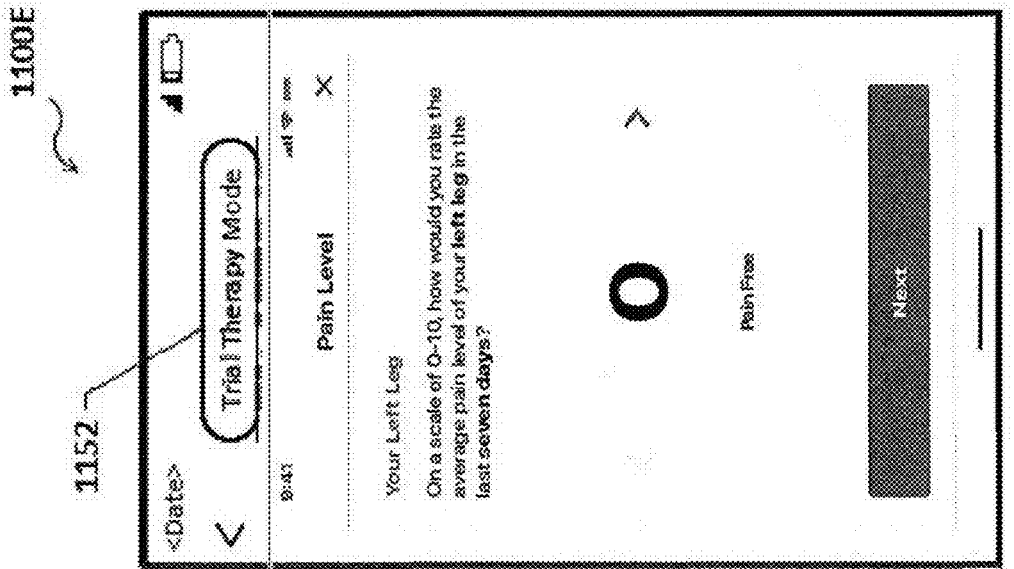
Figure 11G:
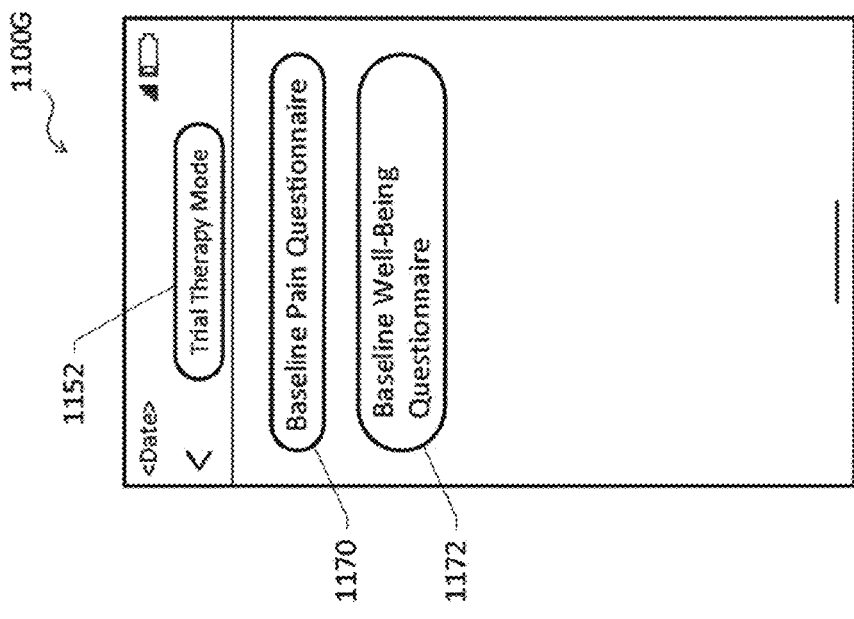
Figure 11F:
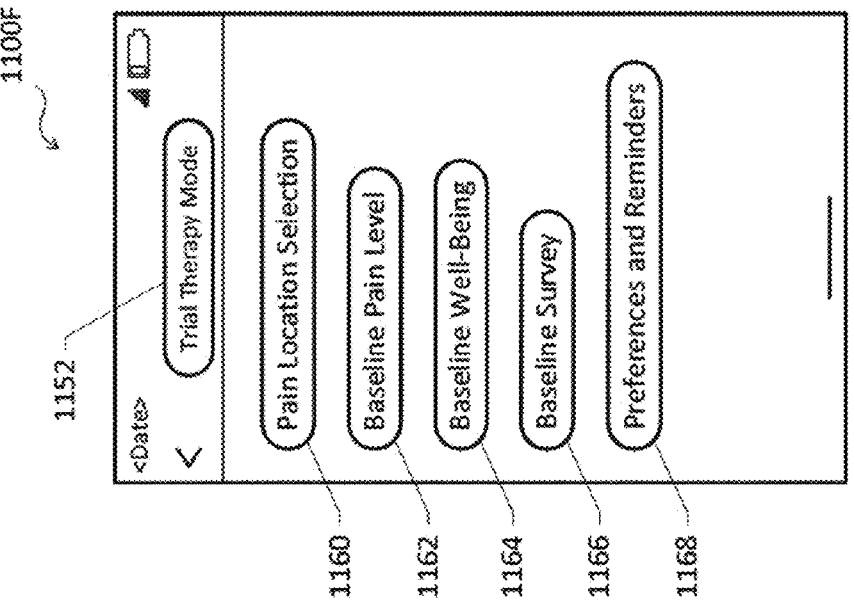

Turning to FIG. 11D, depicted therein is an example GUI display screen 1100D of a patient controller device for facilitating reporting of patient outcomes (either during an initial trial period to evaluate therapy or during long-term use of the therapy). The GUI display for reporting patient outcomes may be provided as a single app or may be integrated with other digital health apps (such as a remote programming/virtual clinic app and/or the patient controller app for controlling operations of the IMD or minimally invasive device). Example GUI display screen 1100F shown in FIG. 11F is illustrative of a menu panel for use by the patient to input data related to the patient's condition related to the therapy provided by the patient's IMD or minimally invasive device. By way of example, a Pain Location Selection menu 1160, a Baseline Pain Level menu 1162, a Baseline Well-being menu 1164, a Baseline Survey menu 1166 and a Preferences and Reminders menu 1168 are illustrated. In one arrangement, Pain Location Selection menu 1160 is operative to enable the patient to select/ identify one or more locations on the patient's body where pain is located or perceived, e.g., left foot, right foot, ankle(s), knee(s), leg(s), pelvis, groin, hip, abdomen, upper/ lower back, hand(s), arm(s), etc.

In some example arrangements, baseline data regarding pain levels (e.g., as a whole and/or for identified bodily regions), sense of well-being, measurements of physiologic and behavioral markers may be established for the patients, wherein each patient may select a varying trial period, e.g., each day, each week, 2 weeks, etc. Patients may answer a plurality of questions with respect to each baseline, wherein the answers may be alphanumeric input (e.g., on a scale of 0 to 10), graphic input, or AN input, or any combination thereof (as shown in GUI 1100E and GUI 1100H in FIGS. 11E and 11H respectively as examples). One or more questionnaires 1170, 1172 may be provided as part of a GUI display screen 1100G for purposes of obtaining patient input(s), as exemplified in FIG. 11G, at least some of which may be presented in a set of hierarchical or nested pull-down menus or dialog boxes.

In some example arrangements, various pieces of data and information from the end points disposed in a digital healthcare network architecture, e.g., architecture 1260 shown in FIG. 12, may also be transmitted to one or more cloud-centric platforms without end user involvement, e.g., as background data collection processes, in addition to user-initiated secure data transfer operations.

As previously noted, one or more remote data logging platforms 1216 of system 1200 (shown in FIG. 12) may be configured to obtain, receive or otherwise retrieve data from patient controller devices, clinician programmer devices and other authorized third-party devices. On an individual patient level and on a patient population basis, patient aggregate data 1250 is available for processing, analysis, and review to optimize patient outcomes for individual patients, for a patient population as a whole, and for relevant patient sub-populations of patients.

Patient aggregate data (PAD) 1250 may include basic patient data including patient name, age, and demographic information, etc. PAD 1250 may also include information typically contained in a patient's medical file such as medical history, diagnosis, results from medical testing, medical images, etc. The data may be inputted directly into system 1200 by a clinician or medical professional. Alternatively, this data may be imported from digital health records of patients from one or more health care providers or institutions.

As previously discussed, a patient may employ a patient controller "app" on the patient's smartphone or other electronic device to control the operations of the patient's IMD or minimally invasive device. For example, for spinal cord stimulation or dorsal root stimulation, the patient may use the patient controller app to turn the therapy on and off, switch between therapy programs, and/or adjust stimulation amplitude, frequency, pulse width, and/or duty cycle, among other operations. The patient controller app is adapted to log such events ("Device Use/Events Data") and communicate the events to system 1200 to maintain a therapy history for the patient for review by the patient's clinician(s) to evaluate and/or optimize the patient's therapy as appropriate.

PAD 1250 may include "Patient Self-Report Data" obtained using a digital health care app operating on patient controller devices 1210. The patient self-report data may include patient reported levels of pain, patient well-being scores, emotional states, activity levels, and/or any other relevant patient reported information. The data may be obtained using the MYPATH app from Abbott as one example.

PAD 1250 may include sensor data. For example, IMDs of patients may include integrated sensors that sense or detect physiological activity or other patient states. Example sensor data from IMDs may include dated related to evoked compound action potentials (ECAPs), local field potentials, EEG activity, patient heart rate or other cardiac activity, patient respiratory activity, metabolic activity, blood glucose levels, and/or any other suitable physiological activity. The integrated sensors may include position sensing circuits and/or accelerometers to monitor physical activity of the patient. Data captured using such sensors can be communicated from the medical devices to patient controller devices and then stored within patient/clinician data logging and monitoring platform 1216. Patients may also possess wearable devices (see, e.g., device 106 in FIG. 1B) such as health monitoring products (heart rate monitors, fitness tracking devices, smartwatches, etc.). Any data available from wearable devices may be likewise communicated to monitoring platform 1216.

As previously discussed, patients may interact with clinicians using remote programming/virtual clinic capabilities of system 1200. The video data captured during virtual clinic and/or remote programming sessions may be archived by platform 1214. The video from these sessions may be subjected to automated video analysis (contemporaneously with the sessions or afterwards) to extract relevant patient metrics. PAD data 1250 may include video analytic data for individual patients, patient sub-populations, and the overall patient population for each supported therapy.

The data may comprise various data logs that capture patient-clinician interactions ("Remote Programming Event Data" in PAD 1250), e.g., individual patients' therapy/ program settings data in virtual clinic and/or in-clinic settings, patients' interactions with remote learning resources, physiological/behavioral data, daily activity data, and the like. Clinicians may include clinician reported information such as patient evaluations, diagnoses, etc. in PAD 1250 via platform 1216 in some embodiments. Depending on implementation, the data may be transmitted to the network entities via push mechanisms, pull mechanisms, hybrid push/pull mechanisms, event-driven or trigger-based data transfer operations, and the like.

In some example arrangements, data obtained via remote monitoring, background process(es), baseline queries and/or user-initiated data transfer mechanisms may be (pre)processed or otherwise conditioned in order to generate appropriate datasets that may be used for training, validating and testing one or more AI/ML-based models or engines for purposes of some embodiments. In some example embodiments, patient input data may be securely transmitted to the cloud-centric digital healthcare infrastructure wherein appropriate AI/ML-based modeling techniques may be executed for evaluating the progress of the therapy trial, predicting efficacy outcomes, providing/recommending updated settings, etc.

In one implementation, "Big Data" analytics may be employed as part of a data analytics platform, e.g., platform 1220, of a cloud-centric digital health infrastructure 1212. In the context of an example implementation of the digital health infrastructure 1212, "Big Data" may be used as a term for a collection of datasets so large and complex that it becomes virtually impossible to process using conventional database management tools or traditional data processing applications. Challenges involving "Big Data" may include capture, curation, storage, search, sharing, transfer, analysis, and visualization, etc. Because "Big Data" available with respect to patients' health data, physiological/behavioral data, sensor data gathered from patients and respective ambient surroundings, daily activity data, therapy settings data, health data collected from clinicians, etc. can be on the order of several terabytes to petabytes to exabytes or more, it becomes exceedingly difficult to work with using most relational database management systems for optimizing, ranking and indexing search results in typical environments. Accordingly, example AI/ML processes may be implemented in a "massively parallel processing" (MPP) architecture with software running on tens, hundreds, or even thousands of servers. It should be understood that what is considered "Big Data" may vary depending on the capabilities of the datacenter organization or service provider managing the databases, and on the capabilities of the applications that are traditionally used to process and analyze the dataset(s) for optimizing ML model reliability. In one example implementation, databases may be implemented in an open-source software framework such as, e.g., Apache Hadoop, that is optimized for storage and large-scale processing of datasets on clusters of commodity hardware. In a Hadoop-based implementation, the software framework may comprise a common set of libraries and utilities needed by other modules, a distributed file system (DFS) that stores data on commodity machines configured to provide a high aggregate bandwidth across the cluster, a resource-management platform responsible for managing compute resources in the clusters and using them for scheduling of AI/ML model execution, and a MapReduce-based programming model for large scale data processing.

In one implementation, data analytics platform 1220 may be configured to effectuate various AI/ML-based models or decision engines for purposes of some example embodiments of the present patent disclosure that may involve techniques such as support vector machines (SVMs) or support vector networks (SVNs), pattern recognition, fuzzy logic, neural networks (e.g., ANNs/CNNs), recurrent learning, and the like, as well as unsupervised learning techniques involving untagged data. For example, an SVM/SVN may be provided as a supervised learning model with associated learning algorithms that analyze data and recognize patterns that may be used for multivariate classification, cluster analysis, regression analysis, and similar techniques. Given example training datasets (e.g., a training dataset developed from a preprocessed database or imported from some other previously developed databases), each marked as belonging to one or more categories, an SVM/SVN training methodology may be configured to build a model that assigns new examples into one category or another, making it a non-probabilistic binary linear classifier in a binary classification scheme. An SVM model may be considered as a representation of the examples as points in space, mapped so that the examples of the separate categories are divided by a clear gap that is as wide as possible (i.e., maximal separation). New examples are then mapped into that same space and predicted to belong to a category based on which side of the gap they fall on. In addition to performing linear classification, SVMs can also be configured to perform a non-linear classification using what may be referred to as the "kernel trick", implicitly mapping their inputs into high-dimensional feature spaces. In a multiclass SVM, classification may typically be reduced (i.e., "decomposed") to a plurality of multiple binary classification schemes. Typical approaches to decompose a single multiclass scheme may include, e.g., (i) one-versus-all classifications; (ii) one-versus-one pairwise classifications; (iii) directed acyclic graphs; and (iv) error-correcting output codes.

In some arrangements, supervised learning may comprise a type of machine leaning that involves generating a predictive model or engine based on decision trees built from a training sample to go from observations about a plurality of features or attributes and separating the members of the training sample in an optimal manner according to one or more predefined indicators. Tree models where a target variable can take a discrete set of values are referred to as classification trees, with terminal nodes or leaves representing class labels and nodal branches representing conjunctions of features that lead to the class labels. Decision trees where the target variable can take on continuous values are referred to as regression trees. In some other arrangements, an embodiment of the present patent disclosure may advantageously employ supervised learning that involves ensemble techniques where more than one decision tree (typically, a large set of decision trees) are constructed. In one variation, a boosted tree technique may be employed by incrementally building an ensemble by training each tree instance to emphasize the training instances previously mis-modeled or mis-classified. In another variation, bootstrap aggregated (i.e., "bagged") tree technique may be employed that builds multiple decision trees by repeatedly resampling training data with or without replacement of a randomly selected feature or attribute operating as a predictive classifier. Accordingly, some example embodiments of the present patent disclosure may involve a Gradient Boosted Tree (GBT) ensemble of a plurality of regression trees and/or a Random Forest (RF) ensemble of a plurality of classification trees, e.g., in pain score classification and modeling.

Depending on implementation, various types of data (pre)processing operations may be effectuated with respect to the myriad pieces of raw data collected for/from the subject populations, e.g., patients, clinicians, etc., including but not limited to sub-sampling, data coding/transformation, data conversion, scaling or normalization, data labeling, and the like, prior to forming one or more appropriate datasets, which may be provided as an input to a training module, a validation/testing module, or as an input to a trained decision engine for facilitating prediction outcomes. In some arrangements, example data signal (pre)processing methodologies may account for varying time resolutions of data (e.g., averaging a data signal over a predetermined timeframe, e.g., every 10 minutes, for all data variables), missing values in data signals, imbalances in data signals, etc., wherein techniques such as spline interpolation method, synthetic minority over-sampling technique (SMOTE), and the like may be implemented.

In some embodiments, sensor data, video data, and/or audio data are analyzed during a virtual clinic or remote programming session to determine rigidity of a patient. For example and referring to FIG. 13, a flowchart illustrating exemplary operations that may occur during a virtual clinic or remote programming session according to embodiments of the present disclosure is shown. It is noted that the exemplary operations shown in and described with respect to FIG. 13 may employ various types of infrastructure, such as the exemplary infrastructure shown in FIG. 12, or other infrastructure, such as suitable patient device(s), clinician device(s), one or more servers, cloud computing resources, or other types of computing devices/resources suitable for facilitating the exemplary operations described in more detail with reference to FIG. 13 below.

In the exemplary flow of FIG. 13, a patient may be instructed to conduct one or more tasks for determining characteristics of the patient's condition. Exemplary tasks may include flexion tasks, tension tasks, or other types of tasks that may be used to evaluate the rigidity of the patient. The one or more tasks may be utilized to capture information that may be utilized to determine characteristics of the patient from which the patient's condition may be diagnosed. Additionally or alternatively, the characteristics may also be utilized to configure a neurostimulation therapy to address the patient's condition. In some aspects, various types of devices may be employed to gather data during patient performance of one or more tasks. For example, the devices may include sensors (e.g., accelerometers, gyroscopes, inertial measurement units (IMUs), electro (EMG) sensors, ultrasound sensors, and the like). Exemplary sensors that can be employed to obtain data to assist patient evaluation based on patient movement (e.g., during performance of the one or more tasks) are described in the publication "Quantification of Hand Motor Symptoms in Parkinson's Disease: A Proof-of-Principle Study Using Inertial and Force Sensors", Ann Biomed Eng. 2017; 45(10): 2423-2436, by Josien C. van den Noort et al., the content of which is incorporated herein by reference.

In addition to capturing sensor data as the patient performs the one or more tasks, one or more cameras may be utilized to capture media content (e.g., image data, video data, etc.) of the patient performing the one or more tasks. In some aspects, the sensor data and media content obtained as the patient performs the one or more tasks may be utilized to diagnose the patient's condition during a virtual clinic and/or a remote programming session. In some aspects, a specific region-based analysis (auto or user-driven) may be conducted to adjust focus within a video field-of-view, such as to focus the media content on a particular region of the patient's body (e.g., the hands, legs, feet, upper body, lower body, etc.). The region of interest of the patient's body may be associated with or determined based on the diagnosed condition(s). To illustrate, a region of interest for a patient diagnosed or suspected of suffering from tremors may be the patient's hand, and the region of interest for a patient diagnosed or suspected of suffering from Parkinson's disease may be the patient's feet and/or legs (e.g., to perform gait analysis, etc.). It is noted that the exemplary regions of the patient's body and conditions described above have been provided for purposes of illustration, rather than by way of limitation. Therefore, it should be understood that the diagnostic and analysis techniques disclosed herein may be readily applied to other conditions and/or regions of interest on a patient's body.

The exemplary flow shown in FIG. 13 may be used to provide real-time feedback on the patient's condition. This allows changes to be quantified in real-time and associated with neuromodulation or other therapies, such as by quantifying changes to measure features or characteristics over time. This can be achieved through high-definition capture and comparison of multiple frames of media content (e.g., multiple sequential images or frames of video content). Additionally, multiple types of captured data may be utilized to provide multiple independent data points or to a combination of different data points for analysis/evaluation (e.g., a combination of captured data associated with vascular change data coupled with rigidity data). In aspects where media content is utilized for analysis and evaluation, multiple types of cameras may be used (e.g., media content may be captured using one or more imaging cameras, video cameras, and/or thermal-based cameras, such as infrared cameras) during a session.

As shown in step 1301, the one or more tasks performed by the patient may include one or more flexion/extension tasks. As the patient performs the task(s) the system captures patient data using one or more sensors (e.g., IMU sensors, EMG sensors, ultrasound sensors, and/or the like). In some aspects, the patient data or a portion thereof may be captured by patient devices, such as the patient devices 104 described and illustrated with reference to FIG. 1B.

The one or more tasks performed by the patient may additionally or alternatively include: one or more opposite hand drawing/writing tasks, at step 1302; one or more walking task(s), at step 1303; one or more standing and/or balancing tasks, at step 1304; and one or more finger-tapping tasks, as step 1305. As described above with reference to step 1301, various sensors and devices may be utilized to capture patient data as the patient performs the one or more tasks. For example, patient data may be captured as the patient performs the tasks associated with steps 1302-1305 using finger cap accessories, IMU sensors, EMG electrode(s), EEG electrodes, gyroscopes, accelerometers, cameras, temperature sensors, heart rate sensors, blood pressure sensors, other types of sensors, or combinations thereof (e.g., a combination involving finger cap accessories, IMU sensors, EMG electrode(s), a combination involving finger cap accessories, IMU sensors, EMG and EEG electrode(s), and so on).

In step 1306, a set of rigidity related metrics are determined. In some aspects, the rigidity related metrics may be determined by one or more servers, such as a server of the virtual clinic/remote programming platform 1214 of FIG. 12. Each metric may be obtained by processing respective sets of patient data captured during performance of one or more of the various patient tasks described above. In some embodiments, the one or more servers may evaluate the patient data to determine characteristics associated with the patient's performance of the task(s), such as a minimum jerk trajectory, a smoothness of motion, a co-contraction profile, a gait profile, an arm-swing profile, a balance/sway, a range of motion, completeness of movement, or other characteristics, and the metrics may be determined based on the characteristics.

While quantifying metrics around or based on patient movement, stiffness measures or metrics may be calculated. For example, metrics such as the minimum jerk trajectory may be used to compute the smoothness of the movement. In a healthy patient, the movement trajectory has a smooth bell-shaped curve with minimal jerk, which may be calculated based on the time derivative of acceleration (e.g., based on accelerometer data). When a patient has tremor or rigidity, it is expected that the movement trajectory deviates from the minimum jerk trajectory (e.g., a jerk trajectory of a healthy patient) and the acceleration may be unsteady. As another non-limiting example, IMU sensors with enough sampling rate can detect the smoothness of motion based on high frame per second (FPS) video recordings. In addition, in a healthy subject, at the initiation of and during the movement, the co-contraction of the agonist and antagonist muscles decreases. However, in a patient with rigidity, the co-contraction levels are higher at the baseline and the decrease of the co-contraction may not be large enough at the initiation of movement. Muscle tone recordings, such as may be observed using EMG signals/sensors, of agonist and antagonist muscles may be used along other sensors for the analysis of the co-contraction profile during movement.

Other measures, such as comparison of movement metrics between the right and left sides (ex: frequency of steps, step interval, or length of arm swing) can be used as a proxy for evaluating or quantifying additional aspects of the patient's condition, such as asymmetry. Metrics associated with balance can be determined by quantifying sway when the patient is performing the one or more tasks (e.g., the standing/balance task(s) at step 1304). Additionally, range-of-motion and completeness of movement can be detected when the patient is performing the one or more tasks (e.g., the flexion/extension and/or the walking tasks, at steps 1301 and 1303, respectively). Identification of any inability for full-extension, lack of motion in trunk, abnormal arm-swing, gait abnormalities (e.g., as detected from lack of heel strike, stooped posture, movement speed, etc.), or other types of analysis may also be performed. Other inputs may include proxies for facial expressions as rigidity may also correlate with blank affect.

At step 1307, the respective metrics are used to compute a rigidity score or other relevant scores or measures indicative of the patient's condition. In some embodiments, the score(s) may be calculated by one or more servers, such as servers of the virtual clinic/remote programming platform 1214 of FIG. 12. The calculation of the metrics and/or the rigidity score may be assisted using ML/AI algorithms. In aspects, the ML/AI algorithms may be trained based on previously captured patient data (e.g., historical patient data captured and processed in accordance with the concepts disclosed herein, such as by the system 1200 of FIG. 12).

In some embodiments, a patient-specific method of computing a rigidity score is performed. For example, Parkinson's Disease (PD) is a heterogeneous disorder, and a score that is patient-specific may be more informative for patients and clinicians to understand individual patient progress (e.g., progression of the disease and/or improvement of the patient's symptoms as a result of treatment). Therefore, characterizing noise present in the signal data when the patient is not rigid may be performed to define a floor value or noise signature that may be used for further computations and operations. To illustrate, the noise signature may be used to characterize the rigidity profile for an individual patient (e.g., individual patients may have different noise signatures). When the patient's measures are outside the noise limits, it may serve as an indication of the presence of rigidity (e.g., rigidity for the specific patient being evaluated).

The above-described techniques may enable the presence of rigidity to be transformed into a binary outcome (e.g., rigidity is present or not present on an individual patient basis) that may be further enhanced with a quantitative score computed from the signals, patient data, and metrics described above. The ML/AI algorithms may be utilized to create or provide a predictive model that integrates the signals and patient data collected from sensors and video during performance of the one or more tasks by the patient. The model may output a value that provides an objective or sensor-driven score. A subjective or evaluator-driven score can also be determined based on clinician assessment and patient-reported outcomes (PROs). The PROs can also be patient-specific and enhanced by the use of chatbots to ensure that all information is being collected without an undue burden on patients. The combined objective and subjective scores may represent the overall rigidity score for the patient and provide a holistic assessment of the patient's symptoms and progress.

At step 1308, the rigidity score is provided to the clinician. In some embodiments, the rigidity score may be provided to the clinician during a virtual clinic/remote programming session, such as may be performed using the system 1200 of FIG. 12. At step 1309, the patient's neurostimulation parameters (e.g., deep brain stimulation parameters, spinal cord stimulation parameters, and/or the like) may be modified and used to update the patient's neurostimulation system. As non-limiting examples, stimulation parameters may include amplitude, frequency, pulse width, and the like. It is noted that in some aspects the scores calculated based on the ML/AI algorithms or model(s) may be utilized to automatically adjust the patient's neurostimulation parameters, rather than providing the score(s) to a clinician and having the clinician modify the neurostimulation parameters.

Referring to FIG. 14, a flow diagram depicting an exemplary flor of operations for creating a predictive disorder model using ML/AI processing according to some embodiments is shown. Additionally, FIG. 15 depicts ML/AI learning data sets 1500 that may be used for creating a predictive disorder model, such as a model created according to the exemplary operations of FIG. 14. It is noted that the operations illustrated and described with reference to FIG. 14 may be utilized with data (e.g., the data captured using the flow of FIG. 13) captured using a virtual clinic/remote programming system (e.g., the virtual clinic/remote programming platform 1214 of FIG. 12 or other systems).

At step 1401, data from neurostimulation patients is captured. In some aspects, the captured data may include data captured from patients in a "stimulation-off" state. Patients may be considered in the "stimulation-off" state when the neurostimulation systems of the respective patients are not providing electrical stimulation to target neural sites. Referring briefly to FIG. 15, in some aspects, the captured data may include "context" data and "sensor" data. The context data may include various types of data, such as geographic data, ethnicity data, disease stage data, existing prescriptions (if any) for each patient, neurostimulation therapy settings for each patient, timestamps (e.g., time of day when therapy was provided, etc.), and macro-modality data. It is noted that the exemplary types of context data shown in FIG. 15 are provided for purposes of illustration, rather than by way of limitation and that the context data may include other types of data or combinations thereof. The sensor data, which may be captured using a variety of sensors or devices, such as peripheral sensors, implanted sensors, or other types of sensors, as described with reference to FIG. 13. The sensor data may also include image content, video content, audio data content (e.g., captured using camera and microphone components of user devices or other types of devices). It is noted that the sensor data may include data captured using any suitable sensor, device, or component, and that peripheral and implanted sensors are shown in FIG. 15 for purposes of illustration, rather than by way of limitation. For example, the sensor data may also include data from wearable devices, such as biometric or other types of data captured by a "smart" watch, a health monitoring device, or other types of consumer electronic devices.

Referring back to FIG. 14, at step 1402, the captured data while the patients are in the "stimulation-off" may be recorded or stored to one or more databases, such as one or more databases of a server platform (e.g., the virtual clinic/remote programming platform 1214 of FIG. 12). At step 1403, the recorded data is labeled. To illustrate, the data captured while the patient is in the "stimulation-off" state may be labeled with information that indicates the data is representative of a disorder state (e.g., patient biometrics, measurements, and the like were captured in the absence of neurostimulation therapy). The labeled data may be utilized to train the ML/AI algorithms to recognize the state of a patient's condition or disorder.

Similarly to steps 14001-1403, data is captured, at step 1404, from patients in a "stimulation-on" state (e.g., while the patients are receiving neurostimulation therapy). It is noted that the receiving of neurostimulation therapy may be continuous (e.g., stimulation pulses may be delivered to target tissue of the patient continuously during the data capturing at step 1404) or periodic (e.g., stimulation pulses may be delivered to target tissue of the patient for a period of time and not delivered for a period of during the data capturing at step 1404). At step 1405, the captured data, which may include image data, audio data, video data, sensor data, other types of data, or combinations thereof, is recorded to one or more databases. At step 1406, the data captured while the patient is in the "stimulation-on" state may be labeled with information that indicates the data is representative of a state of the patient's condition during providing of the neurostimulation therapy (e.g., patient biometrics, measurements, and the like were captured in the presence of the neurostimulation therapy). The labeled data may be utilized to train the ML/AI algorithms to recognize the state of a patient's condition or disorder when neurostimulation therapy is provided or the impact of the neurostimulation therapy on the patient's condition or disorder. At step 1407, the state/context data (e.g., the state/context data of FIG. 15) may be processed or conditioned (e.g., using generalized Baye conditionalization, Jeffrey conditionalization, and/or any other suitable methods). The conditioning may improve model accuracy.

At step 1408, ML/AI processing is applied to at least a portion of the captured data (e.g., a portion of the data captured while the patients are in the "stimulation-off" and "stimulation-on" states) to develop a predictive disorder model. In some aspects, the predictive disorder model may be configured to classify disorders of patients (e.g., health state, disorder state, disorder level, etc.). The model(s) may utilize various classification techniques, such as random forest classification, Naive Bayes classification, k-means clustering, genetic algorithms, neural networks, reinforcement learning strategies (e.g., Q-learning, Temporal Difference learning, Markov decision processes, etc.), and/or any suitable ML/AI methods.

The predictive disorder model may include various disorder states. For example, for a movement disorder such as Parkinson's Disease, the predictive disorder model may include model components such as tremor, rigidity, facial drop, balance, hallucinations, and/or any other relevant disorder symptoms. As illustrated in FIG. 15, the model components may also be employed to create an overall disorder classification or classification model, such as "PD level" that reflects an ensemble of the selected model components. It is noted that while FIG. 15 illustrates aspects of a model for a movement disorder, such description has been provided for purposes of illustration, rather than by way of limitation and predictive models of the present disclosure may utilize additional model data for analysis of other disorders, such as chronic pain disorders.

At step 1408, the predictive model is used to evaluate patients and ascertain the condition(s) of their neurological disorders. As described above, the predictive models may be trained with datasets associated with patients in the "stimulation-off" and "stimulation-on" states. As such, the predictive models may be utilized to evaluate the condition of a patient's disorder or condition based on data captured while the neurostimulation stimulation therapy (or other type of therapy) is or is not being provided. The outputs of the predictive model may be utilized (e.g., by a clinician or automated tools) to assist with programming of neurostimulation parameters (e.g., adjust the parameters, conditions for triggering delivery of neurostimulation, etc.), augmenting virtual clinic/remote programming sessions, and/or any other suitable patient evaluation processes.

As discussed herein, video data of patients may be processed to support providing neurostimulation therapies according to some embodiments. The processing of the video data may occur substantially in real-time (e.g., during a virtual clinic/remote programming session). Alternatively, the processing of video data may occur on previously recorded video. The processing of the video data may be used to assist evaluation of one or more symptoms of the patient. Additionally or alternatively, the processing of the video data may be utilized to build a ML/AI model for use in neurostimulation therapies.

Referring to FIG. 16, a flowchart depicting exemplary operations for processing video data to support provision of neurostimulation therapies to patient according to some embodiments is shown. At step 1601, video data of the patient is captured. The video data may be captured, for example, during a virtual clinic/remote programming session according to some embodiments. The video data may be captured from a user device, such as patient controller (e.g., patient controller 150 of FIG. 1A, patient controller devices 1210 of FIG. 12, or other types of devices). In step 1602, the video data is processed to extract features associated with the patient. To illustrate, the extracted features may be associated with the patient's facial expression, posture, limb activity, or other anatomical considerations. In some aspects, the features may be extracted using landmark recognition software. For example, if the video analysis is conducting an analysis of facial expression, suitable software libraries include the FACEMARK facial landmark API available from OpenCV, the CLM-framework (also known as the Cambridge Face Tracker), FACE++ Web API, CLOUD VISION API (Google) as examples. When the video analysis is conducted based on posture, limb activity, or other anatomical considerations that involve a large amount of the patient's body, other landmark software packages may be employed such as MEDIAPIPE Pose (Google) and OPENPOSE library (OpenCV). MediaPipe also provides a number of software API packages for video analysis including FACE MESH and POSE packages for detecting facial landmarks and body landmarks respectively.

In step 1603, key landmark points are selected from the points or features generated during step 1602. The key landmark points may be selected to identify relevant characteristics related to neurological disorder symptoms. For example, facial expression and body posture can be related to pain and/or motor symptoms of chronic neurological disorders. For example, FIGS. 17A and 17B depict sets 1700 and 1750, respectively, of key landmark points that may be utilized for facial expression analysis and pose analysis according to some embodiments.

In step 1604, regional area metrics are calculated from the key landmark points. The regional area metrics are indicative of the area bounded by key points. For example, in FIG. 17A, areas $A_{LEFT}$ and $A_{RIGHT}$ are shown, and in FIG. 17B areas A1-A4 are shown. As discussed herein, the calculated areas may be compared to generate a representation of balance in expression and/or pose which is related to symptoms of neurological disorders. To illustrate, when a patient is comfortable and happy, the shape of the face is balanced and exhibits a relatively high degree of symmetry. However, when a patient is subjectively experiencing pain, their facial expression will often contort and lose the balance or symmetry in the shape of the face. Similarly, a loss of balance or symmetry can be detected in the pose of a patient when the patient is experiencing pain or is subject to certain symptoms of motor disorders (e.g., Parkinson's Disease). In some embodiments, the patient may be requested to perform one or more physical task (e.g., as described with reference to FIG. 13) while the data is captured and/or the analysis occurs. For example, the patient may be requested to walk a short distance within the view of the patient's camera. The processing and analysis of the patient's pose or posture during this task may occur to classify the patient's disorder state.

In step 1605, one or more metrics may be calculated based on the set of landmark points or features and/or regional areas. For example, the one or more metrics may include ratios, such as a balance ratio, a cross ratio, and/or other relevant ratios derived from the landmark points and/or regional areas. In some aspects, the ratios and/or metrics may be calculated for each video frame or for a relevant fraction or set of video frames. For example, one frame every 0.1 or 0.2 seconds may be selected for analysis even though the frame rate of the video signal may be higher. The selection of the frame rate analysis may be varied depending on the quality of the video signal and any other relevant factor.

To illustrate, analysis of a patient's facial expression using the set of key landmark points 1700 of FIG. 17A, the two areas ($A_{left}$ and $A_{right}$) may be defined based on the respective key landmark points as shown in FIG. 17A. The balance ratio may be defined as:

$$\text{balance ratio} = A_{left}/A_{right}.$$

For analysis of facial expression using the set of key landmark points 1700, a distance ($D_{vertical}$) between point 10 and point 9 and a distance ($D_{horizontal}$) between point 4 and point 5 may be determined. Subsequently, $D_{vertical}$ and $D_{horizontal}$ may be used to calculate a face ratio. The face ratio may be expressed as:

$$\text{face ratio}=D_{vertical}/D_{horizontal}.$$

For analysis of facial expression using set of key landmark points 1700, a distance ($D_{cross1}$) between point 11 and point 14, and a distance ($D_{cross2}$) between point 12 and point 13 may be calculated and used to determine a cross ratio. The cross ratio may be defined as:

$$\text{Cross ratio}=D_{cross1}/D_{cross2}.$$

With reference to FIG. 17B, analysis of patient pose or posture using the set of key landmark points 1750, let $D_{left}$ be defined as the distance between point 1 and point 7, and $D_{right}$ be defined as the distance between point 2 and point 8. Using $D_{left}$ and $D_{right}$, a balance ratio may be determined. The balance ratio may be defined as:

$$\text{Balance ratio}=D_{left}/D_{right}.$$

For analysis of patient pose or posture using the set of key landmark points 1750, let $D_{cross1}$ is defined as the distance between point 1 and point 8, and $D_{cross2}$ be defined as the distance between point 2 and point 7. The cross ratio may then be defined as:

$$\text{cross ratio}=D_{cross1}/D_{cross2}.$$

For analysis of patient pose or posture using set of key landmark points 1750, let $D_{shoulder-knee1}$ be defined as the distance between point 1 and point 5 and let $D_{shoulder-knee2}$ be defined as the distance between point 2 and point 6. A shoulder-knee ratio may then be calculated based on $D_{shoulder-knee1}$ and $D_{shoulder-knee2}$. For example, the shoulder-knee ratio may be defined as:

$$\text{shoulder-knee ratio}=D_{shoulder-knee1}/D_{shoulder-knee2}.$$

For analysis of patient pose or posture using set of key landmark points 1750, let $D_{elbow-foot1}$ be defined as the distance between point 9 and point 8, and let $D_{elbow-foot2}$ be defined as the distance between point 10 and point 7. An elbow-foot-cross ratio may be calculated based on $D_{elbow-foot1}$ and $D_{elbow-foot2}$. For example, the elbow-foot-cross ratio may be defined as:

$$\text{elbow-foot-cross ratio}=D_{elbow-foot1}/D_{elbow-foot2}.$$

Referring back to FIG. 16, at step 1606, a time domain sliding window is applied to the one or more metrics (e.g., the ratio data and/or other relevant metric data). In some embodiments, the sliding window may have a duration of one second. That is, the ratio and metric data from a given one second time window is selected for aggregate analysis. However, it is noted that sliding windows having a duration longer than one second or shorter than one second may be utilized.

In step 1608, a ML/AI model, such as the predictive model described above with reference to FIGS. 14 and 15 or another model, may be applied to media content of a particular sliding window. The model may be configured to process or apply a classification the media content (e.g., to frames of video content, etc.). In an aspect, only relevant portions of the media content (e.g., relevant video frames) within the sliding time window may be classified. For example, the relevant portions may include video frames determined to exhibit (e.g., by the model) a threshold probability of being correctly classified as either depicting a healthy/normal state or a symptom state (e.g., pain).

The model may be configured to calculate a probability of relevance for each portion of the media content (e.g., a probability that a classification for a particular frame of video depicts a healthy/normal state or a symptom state), and relevant portions of the media content may be identified based on a threshold probability. In an aspect, the threshold probability used to identify relevant portions of the media content may be a probability of at least 0.8 (e.g., media content having a probability of relevance ≥0.8, where 0.8=threshold probability). It is noted that a threshold probability of 0.8 has been described for purposes of illustration, rather than by way of limitation and that the threshold probability may be configured to a higher or lower value if desired. Moreover, in some aspects, different threshold probabilities may be used for different conditions/symptoms. Regardless of the particular value to which the threshold probability is set or the number of probability threshold used, it should be understood that the threshold probabilities may be changed over time. For example, initially the threshold probability may be configured to a first value (e.g., 0.65), but the model may become more accurate over time (e.g., as additional training data is obtained and additional training of the model is performed). As the model's classification capabilities improve the threshold probability may be adjusted, thereby minimizing the likelihood that portions of the media content identified as relevant end up being unsuitable for use in evaluating the patient. It is noted that any portions of the media content having a threshold below the threshold probability may be ignored (e.g., because those portions of the media content may be associated with inaccurate or incorrect classifications, or may otherwise be unsuitable for further use in evaluating the state of the patient or the patient's condition).

At step 1609, the relevant portions of the media content identified in step 1608 may be used to calculate a disorder score. In an aspect, the disorder score may be calculated based on metrics derived from the relevant portions of the media content, such as the exemplary metrics described above with reference to step 1604. In some aspects, aggregate metrics (e.g., average, median, etc.) may be calculated based on the ratios/metrics of the relevant portions of the media content. The calculated ratio/metrics for the relevant portions of the media content within the sliding window may then be subjected to ML/AI processing or classification to calculate the disorder score, which may be attributed to or associated with the sliding window (and the relevant portions of the media content thereof).

In step 1609, the disorder score(s) is provided to the clinician. In some aspects, the disorder score(s) may be provided to the clinician via a graphical user interface, such as a graphical user interface of an application resident on a clinician programmer device. In some aspects, the graphical user interface may include one or more graphical user interface components that change color in a manner relevant to the patient state classification. For example, the patient video component may include a border component. The border component may include a "green" color for a patient normal state, a "red" color for a patient symptom present state (e.g., pain, rigidity, tremor, and/or the like is present), and a "neutral" color (e.g., gray) for intermediate or uncertain classifications. It is noted that the exemplary colors and associated meanings described above have been provided for purposes of illustration, rather than by way of limitation and that other types of color schemes and indications may be utilized in accordance with the concepts disclosed herein.

In step 1610, the clinician or a computational therapy algorithm provides settings for the patient's neurostimulation therapy based on the processed video of the patient. In some aspects, the above-described process may be performed continuously or repeatedly during the virtual clinic/ remote programming session. That is, as the clinician changes stimulation parameters, the indication of the patient state is updated as the video of the patient is streamed to the clinician for review during the virtual clinic/remote programming session.

Figure 18B:
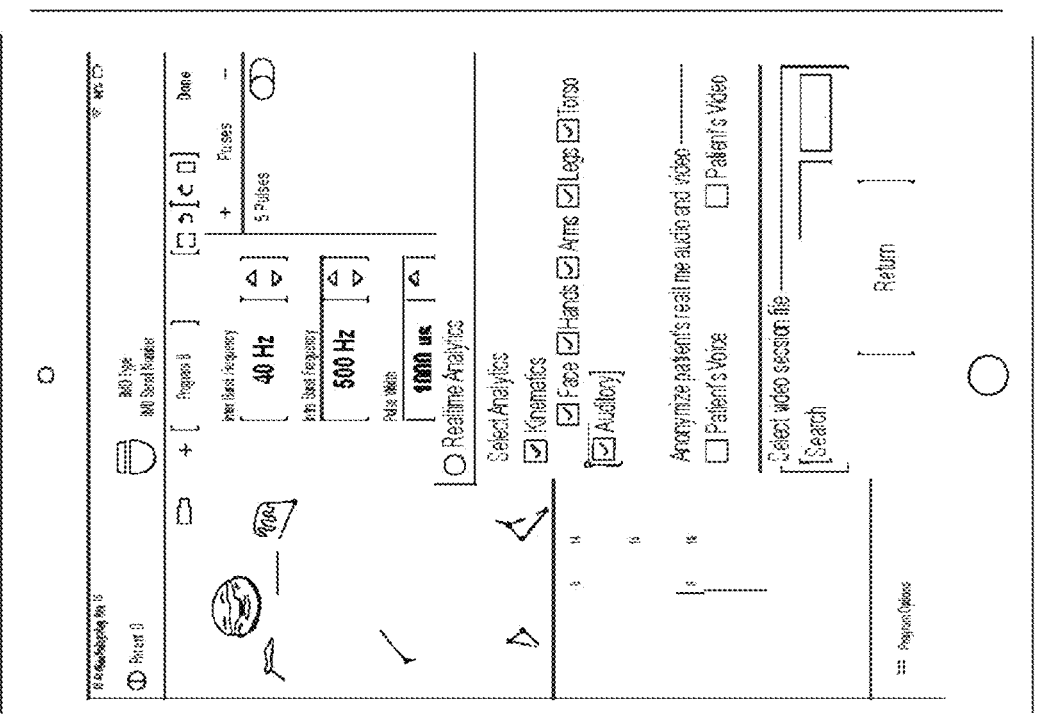
Figure 18A:
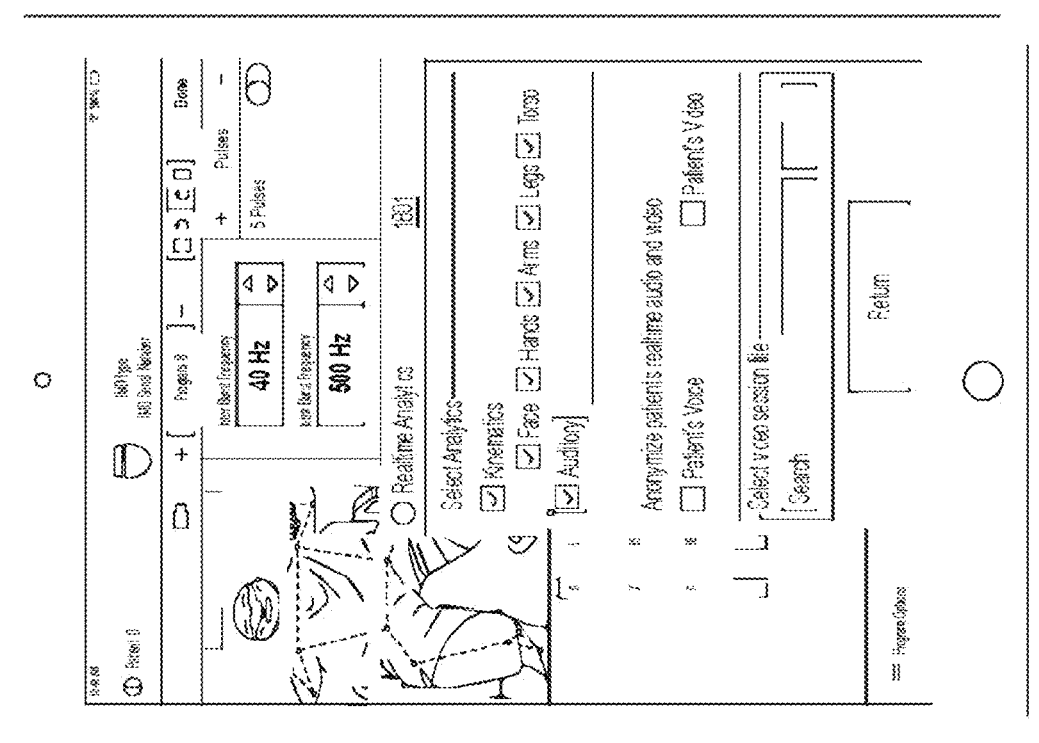

As discussed herein, ML/AI models of neurological disorders may be constructed using a variety of data sets. The ML/AI models may be employed to automatically classify patient states to assist virtual clinic/remote programming sessions. Referring to FIG. 18A, a screenshot depicting exemplary user interface for a clinician programmer device for conducting virtual clinic/remote programming sessions is shown as a user interface 1800. The user interface 1800 may be adapted to provide analytics of the patient concurrently with presentation of video content of the patient as the patient performs one or more tasks (e.g., the one or more tasks of FIG. 13 or other tasks) to the clinician. As described above, the presentation of the video content may include presentation of pre-recorded video of the patient. Additionally or alternatively, the presentation of the video content may occur in real-time, such as via streaming the video content to the clinician programmer device during a live virtual clinic/remote programming session.

In some embodiments, the analytics include analytics associated with kinematics (e.g., data related to movement of the patient). In some embodiments, the analytics include auditory data from analysis of the patient's voice. It is noted that the exemplary analytics described above (e.g., kinematics and auditory analytics) have been provided for purposes of illustration, rather than by way of limitation and that additional types of analytics may be utilized by embodiments of the present disclosure. The user interface 1800 may include interactive GUI elements that enable the clinician to control selection of available ones of the analytics during presentation the media content. For example, the user interface 1800 may include pop-up control component 1801. The pop-up control component 1801 may allow the clinician to activate selected analytics, as well as configure parameters associated with the analytics. To illustrate, in FIG. 18A the pop-up control component 1801 includes interactive elements (e.g., check boxes) that enable the clinician to select specific kinematics, such as kinematics related to the patient's face, hands, arms, and legs. The pop-up control component 1801 also includes interactive elements to activate presentation of analytics associated with the patient's voice.

As described above, the media content (e.g., video data) may be processed using feature recognition software to identify various features or points associated with the patient. The features may be displayed over the patient video during presentation of the media content in accordance with the analytics activated by the clinician. In some aspects, lines connecting different features (e.g., key landmark points) may also be displayed as appropriate (e.g., along the torso, arms, legs, fingers, etc) as shown in interface 1800. Additionally, a mesh display generated based on facial features may be displayed over the patient video as shown in interface 1800. In some aspects, the mesh display may be generated using recognition software libraries, such as a library or libraries of the above-mentioned landmark recognition software.

In some embodiments, the presentation of video and/or audio may be anonymized. As shown in FIG. 18B, video of the patient may be replaced entirely by display of the landmark points, mesh, and frame components generated based on the features identified in the media content. It is noted that the exemplary landmark points, mesh, and frame components may be animated based on the kinematics analytics and/or the auditory analytics, thereby enabling the clinician to visualize movement of the patient as the patient performs the one or more tasks, such as the tasks described above with reference to FIG. 13 or other tasks. It is noted that in some aspects the user interface 1800 may also provide interactive elements that enable the clinician to toggle between the overlay view described with reference to FIG. 18A and the anonymous view described with reference to FIG. 18B. The ability to toggle between the two different views may enable the clinician to more easily see certain kinematics or focus on specific aspects of the displayed kinematics (e.g., to display kinematics of the patient's hands and arms during evaluation of tremors, or feet and legs during evaluation of Parkinson's, such as gait analysis).

Figure 18D:
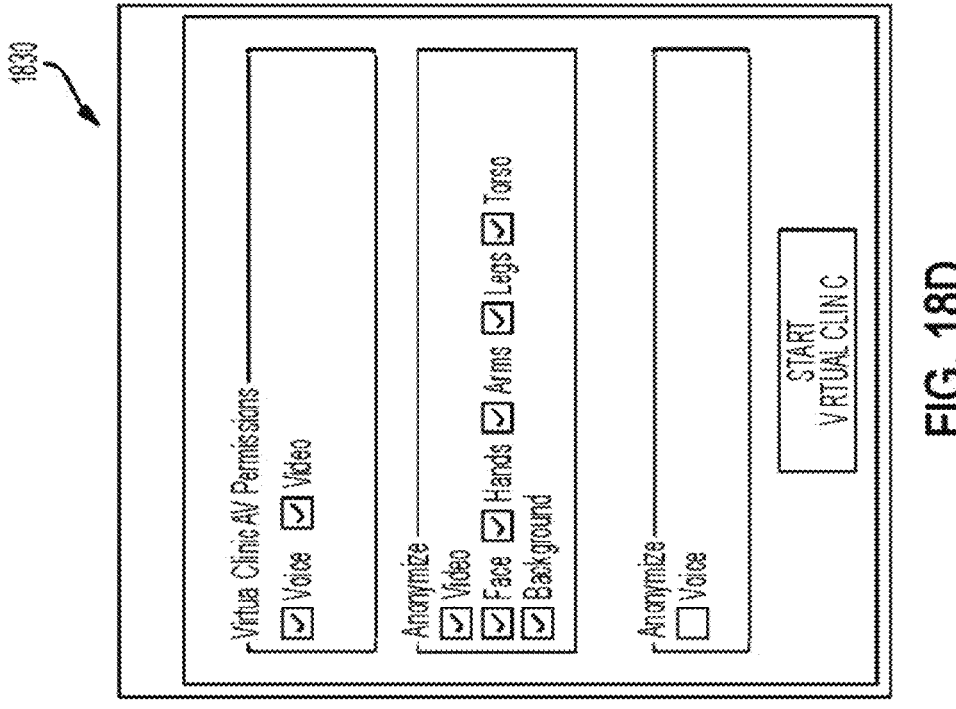
Figure 18C:
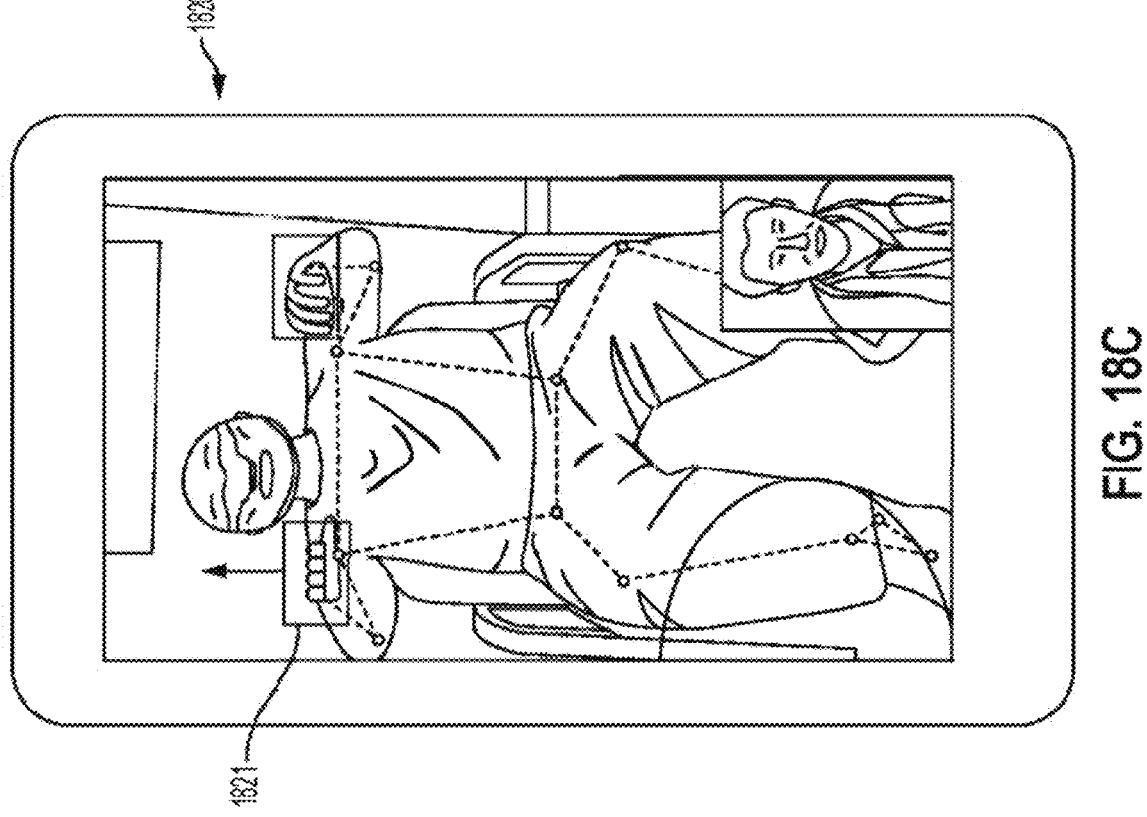

Referring to FIG. 18C, a screenshot depicting aspects of a user interface which may be displayed on a patient device is shown as a user interface 1820. In some aspects, the user interface 1820 may be displayed on a patient controller device (e.g., the patient controller 150 of FIG. 1A, patient controller 800 of FIG. 8, or patient controller 1210 of FIG. 12) or another patient device (e.g., one or more of the patient devices 104 of FIG. 1B). The user interface 1820 may include functionality for generating media content (e.g., video content, image content, and/or audio content) that may be used in connection with the various analytics described above with reference to FIGS. 18A and 18B.

As shown in FIG. 18C, the user interface 1820 may display the landmark graphical features corresponding to the kinematic components selected by the clinician, enabling the patient to view the same kinematics as the clinician. Additionally, user interface 1820 may be used to provide feedback or commands to the patient, such as instructions for the patient to move their face, hands, limbs, torso, etc. into an optimal position for generation of the selected analytics. For example, user interface 1820 includes GUI component 1821, shown as a box, around the patient's right hand. In some aspects, the GUI component 1821 may provide a visual indication regarding whether the patient or a portion of the patient's body, is in a desired or optimal visual location. For example, the GUI component 1821 may be colored "green" to indicate the patient is in the optimal location and colored "red" to indicate the need to reposition. Further, the GUI component 1821 may include one or more indicators, shown as an arrow in FIG. 18C, to indicate a direction of movement to place the patient into the optimal location.

Referring to FIG. 18D, a screenshot depicting aspects of a user interface presented to a patient are shown as GUI component 1830. The GUI component 1830 may provide functionality for controlling how input from the patient during a virtual clinic/remote programming session is received. For example, GUI 1830 may include interactive elements (e.g., check boxes, radio buttons, etc.) that may be selected or activated by the patient to grant permission for audio communication, visual communication, or audio/visual communication during the session. Additionally, the GUI component 1830 may provide interactive elements enabling the patient to control whether auditory and/or video content may be recorded during the session.

The GUI component 1830 may also include interactive elements that enable the patient to control whether the kinematic analytics are displayed to the clinician in the anonymized or non-anonymized mode, including sub-segments. For example, the patient may select to anonymize all video data by checking the interactive element labeled "Video" underneath the first "Anonymize" header. In such case, all available video options will be automatically checked. Alternatively, the patient may select specific video sub-components to be anonymized (e.g., "Face", "Hands", "Arms", "Legs," "Torso" and "Background"). Similarly, the patient may also choose to anonymize the voice communi- cation (if desired). The patient may choose to allow the clinician to view a full video presentation (such as the patient view in FIG. 18C, a completely anonymized view such as the patient view in FIG. 18B, or any variation thereof). It is noted that the GUI component 1830 is pro- vided by way of illustration, rather than by way of limitation and that the GUI 1820 may include other suitable interface configurations and components that provide functionality for allowing the patient to view and control aspects of audio and visual communications during a virtual clinic/remote programming session.

Referring to FIG. 19, a flowchart depicting exemplary operations for conducting a virtual clinic/remote program- ming session according to some embodiments is shown. In step 1901, a virtual clinic session is started (e.g., using the operations discussed herein). In step 1902, the patient's consent for AV communications is obtained. Obtaining the patient's consent may include obtaining user input for respective anonymizing options, as described above with reference to FIGS. 18C and 18D. In some aspects, the patient (or the clinician) may choose to remove the back- ground from the video communications or any bodily region or area from the video (including, optionally, one or more of the options from FIG. 18D). In step 1903, the initial AV communication for the virtual clinic/remote programming session begins according to the patient AV selections. In step 1904, options for kinematic and/or auditory analysis are received from the clinician to assist patient evaluation, as described above with reference to FIGS. 18A and 18B. In step 1905, the video/audio stream is augmented with ML/AI assisted kinematic and/or auditory analytics (including, optionally, one or more of the analytics discussed herein). In step 1906, the clinician or a computational therapy algo- rithm provides settings for the patient's neurostimulation therapy based on the processed video of the patient.

As discussed herein, some embodiments the kinematic analysis may be conducted while a patient performs a functional task (e.g., walking to permit evaluation of the patient by the clinician). In some embodiments, a patient physical therapy application is provided to the patient to assist management of the patient's neurological disorder. The physical therapy application may operate on a patient controller (e.g., the patient controller 150 of FIG. 1A, patient controller 800 of FIG. 8, or patient controller 1210 of FIG. 12) or another patient device (e.g., one or more of the patient devices 104 of FIG. 1B). In some embodiments, virtual reality (VR) devices may be used to assist the physical therapy operations. The physical therapy application may provide guided instructions for the patient to conduct physi- cal activities. The physical activities may include activities selected to improve the patient's health, improve motor function, accommodate the patient to changes in physical sensations during movement as a result of a neurostimula- tion therapy, and/or assist any suitable clinical improvement in the patient. Additionally, the physical therapy application may capture patient data while the patient performs respec- tive activities according to the instructions of the app. For example, physiological data, movement data, and other data may be captured using one or more patient devices (e.g., one or more of the patient devices 104 of FIG. 1B or another device). Additionally, video and/or audio data from the patient may be captured and analyzed as discussed herein.

The captured data may be reviewed by the clinician to evaluate the patient's response and progress to neurostimu- lation therapy.

Referring to FIG. 20, a flowchart depicting exemplary operations for conducting a physical therapy session in accordance with some embodiments is shown. In step 2001, the patient starts the physical therapy application on a patient controller (e.g., the patient controller 150 of FIG. 1A, patient controller 800 of FIG. 8, or patient controller 1210 of FIG. 12) or another patient device (e.g., one or more of the patient devices 104 of FIG. 1B). In some aspects, the physical therapy application may be the physical therapy application described above. In step 2002, patient activity is recorded using camera functionality and/or sensors of avail- able patient devices. As explained above, media content may be recorded during the patient's performance of the task(s) or activities using camera functionality and/or a microphone functionality of the patient's patient controller device, com- puter, or other suitable device. In some aspects, one or more external sensors may additionally or alternatively be employed to gather relevant patient data. For example, insole pressure sensors for quantifying balance, pressure distribution, or other information may be utilized. Also, wearable accelerometers and/or gyroscopes (e.g., embedded within bracelets, watches, gloves, shoes, and the like) may be used to capture information that may be used to quantify arm and leg movement, sleep, trajectory, and/or timing. In some aspects, the patients can opt to wear "markers" on key joints of their body and use an optic movement-tracking system (such as Kinect). In some embodiments, breathing sensors, such as strap-on chest pressure sensors may be employed to detect respiration activity. Also, any number of sensors for sensing cardiac related activity may be employed (e.g., heart rate/blood oxygen sensors, such as watches, or wearable EKG sensors to detect heart rate and oxygen level).

In step 2003, the patient is provided guided instructions for one or more physical tasks or activities to be completed by the patient. In some aspects, the guided instructions may include video and/or audio presentations. For example, a video or images and text may be displayed to the user to illustrate the types of tasks or activities the patient is to perform.

Patients with movement disorders such as Parkinson's disease often report difficulties with everyday tasks such as buttoning (e.g., a shirt), brushing, and/or writing. In some embodiments, the physical therapy application may be tai- lored to the specific condition or disorder of the patient in order to train the patient on activities impacted by their specific condition or disorder, which may provide substan- tial improvements in the patient's quality of life.

In some embodiments, the physical therapy application may provide instructions for suitable physical exercises, such as tai chi or mild to moderate effort treadmill training, aerobic training, and dance activities. Tai chi may be advan- tageous for patients with neurological disorders. There have also been clinical studies that investigated the benefit of exercising, particularly the ones that involve balance train- ing, such as tai chi, for movement disorders (e.g., Parkin- son's disease). For example, in a study (Tai Chi versus routine exercise in patients with early- or mild-stage Par- kinson's disease: a retrospective cohort analysis, Braz J Med Biol Res. 2020; 53(2): e9171) that involved 500 people with mild-to-moderate Parkinson's disease, one group received tai chi training 80 minutes per day, three days per week, for two months. The other group received regular exercising (including treadmill training, aerobic training, and dance) for 90 minutes per day, three days per week, for two months.

Participants in the tai chi group reported a significantly reduced number of falls (average of 3.45 vs. 7.45 over the past six months), and many of them discontinued or reduced the use of other therapies, such as levodopa.

Similarly, in another study (Tai Chi and Postural Stability in Patients with Parkinson's Disease, N Engl J Med 2012; 366:511-519) that recruited 195 men and women with mild to moderate Parkinson's disease, subjects were randomly assigned to twice-weekly sessions of either tai chi, strength-building exercises, or stretching. After six months, those who did tai chi were about two times better than those in the resistance-training group and four times better than those in the stretching group in terms of balance. The tai chi group also had significantly fewer falls, and slower rates of decline in overall motor control. These studies demonstrate that exercise that involves balance training as part of a physical therapy routine can provide additional benefits for people with balance/gait-related disorders, such as Parkinson's disease, in addition to the benefits exercising itself already brings.

In some embodiments, the patient may be provided a VR or AR viewing device to augment the user experience for the presentation of the guided instructions (and feedback described herein). Although optional, being immersed in a VR/AR-based environment can often encourage the trainee to consistently exercise by providing additional visual and audio stimuli. In the case of tai chi training, a pre-recorded VR/AR teacher can be presented in front of the trainee for learning. The VR/AR teacher can also be a persona (or hologram) based on adaptable chatbots to personalize the therapy experience. The teacher's body can be superimposed onto the trainee's body so that the trainee can mimic the teacher's exact movements. Here, the trainee would match the ideal movement trajectory/posture outlined by the digital teacher. In this case, the gaze of the patient or a slight change of EMG may cue the movement initiation.

In another aspect of exercising with a virtual reality or augmented reality experience according to the present disclosure, the VR or AR detects the intention of the subject, filters out the tremor, and displays undisturbed arm or leg movement. The rationale is that a tremor in Parkinson's disease patients may be caused by overcompensation of the posture in the body control while the postural information is erroneous because of the malfunction of thalamic relay neurons. By displaying the correct posture without the tremor using VR/AR, the patient may stop trying to compensate (or overcompensate) for the postural error, which hypothetically may reduce the occurrence of the tremor or the severity of the tremor. Because the tremor frequency is around 5 Hz, notch filtering may remove the tremor and show smooth motion.

In case of a freezing event, the display of the intended movement initiation may rescue a patient from freezing.

In some embodiments, a gesture training paradigm may also be implemented for patients who prefer gesture training over (or in addition to) balance and gait training. This training will leverage music or art "therapy." In other embodiments, the gesture training paradigm can also be disguised as games instead of music training. In embodiments using a music-based therapy paradigm, the patient will learn to control the notes and the pitch of the music via various common gestures they would use in real life, such as brushing, writing, buttoning, finger movements, and the like. Each gesture can code a note, and the relative positioning of the two hands/arms can control pitch. This paradigm could look very similar to playing the theremin, and an AI may be implemented to rate the performance and offer haptic feedback (as discussed herein). Gloves or arm sleeves with actuators embedded at the interface may be employed for haptic feedback in some embodiments.

A less specific version of this gesture training can also be implemented as "3D painting", where the patient is asked to paint with a VR device in a virtual 3D space. This would involve precise positioning of fine movements as well as localization in a 3D space. This can be done either via copying an existing 3D painting, or having the patient create their original painting. In either case, an AI can be used to judge the movement precision of the patients, instead of the paintings themselves.

In step 2004, feedback may be provided during patient performance of the task(s) or activities. Having this measurement in turn offers opportunities for the AI in the physical therapy application to offer feedback to the patient if the patient repetitively makes the wrong move or mistimes the move. The feedback can be achieved via actuators embedded into the fabrics of the patient's clothing, or special clothing articles (such as gloves, socks, shoes) that have embedded actuators. For example, if the patient is supposed to shift his weight to the left foot but failed to do so, a vibration can take place on the left foot to remind the patient. The cadence and frequency of the feedback can be driven by the AI or set by the patient. Presumably, as the patient gets better via practicing, the haptic feedback can change to a different vibration pattern to signal more complex feedback, such as to accelerate movements, deaccelerate movements, or even signaling a "good job".

In some aspects, exercise programs (moves) may have different difficulty levels. For patients who have more severe disease conditions or faster progressive severity, the program may start with the easiest level(s) and work their way up to higher difficulties. The AI can also correspondingly offer more feedback and support as the exercise difficulties increase.

In the case of a fall, or any situation of crisis, the sensors be configured to detect the adverse event and offer an "emergency intervention" by either switching to the most efficacious setting, or calling a care coordinator. Similarly, if the sensors detect that the patient is engaging in more dangerous movements, strong vibrations can also be sent via haptic feedback to remind/prevent the patient from performing movements that are out of the patient's comfort zone.

In step 2005, the stimulation parameters of the patient's neurostimulation therapy may be titrated during the performance of the tasks or activities. For example, if a patient has an implanted device such as DBS, the device can interact with the exercise platform in a closed-loop manner. The efficacy of neurostimulation for a neurological disorder can be state-dependent, as exercising could potentially change the efficacy of certain programmed settings. In such a situation, the implanted device can be controlled (e.g., by the patient controller device) to make small adjustments to programmed parameters to "explore" the therapeutic state space when patient performs various exercises, and the data can be used as training data for a deep learning algorithm to predict which parameter set is best suited for each exercise for this particular patient, thereby enabling an "exercise mode" to be individually developed for each patient. This can also include explorations of known and/or novel stimulation waveforms and paradigms that could be better suited for the patient given a specific exercise.

Additionally, based on how well the patient is progressing in their familiarity and control of their exercise, an AI can be trained to slowly decrease the current of the implanted device setting, and therefore offering less therapy. This will offer the patient more "challenge" in terms of not being able to control their movement due to movement disorder symptoms. This "rehab mode" can motivate the patient to be intentional with their exercise training. The percent deviation from the optimal programming parameter can be prescribed by a physician and be controlled within a configured safety limit based on the particular patient, such as to maintain the parameters within a therapeutic range. In this manner, a digital equivalent of physical therapy may be provided and enable patients to perform therapy tasks at increasing levels of difficulty (either due to the particular tasks selected, the speed at which the tasks are performed, or due to particular configurations of stimulation parameters).

Similarly, if the patient performs worse in the exercise over time, the AI can adjust to a more efficacious therapeutic amplitude or setting, to offer more assistance to the patients.

Further, exercise alters the plasticity of the brain, and therefore, with long term recordings of sensor data and neural data at the implanted devices, one can infer any long term changes in the patient's disease improvement/progression. A correlation can be helpful for the clinicians to understand the patient's disease states and can also instruct a change in the programming setting of the implanted device.

In step 2006, an analysis of patient video and/or sensor data is conducted to characterize the patient conducting. The analysis may include ML/AI processing as discussed herein. Kinematic data may be calculated or determined for the patient based on the video and sensor data using one or more of the techniques described herein.

In step 2007, the performance data and/or video data is provided to a clinician for review. For example and referring to FIG. 21, a screenshot of an exemplary graphical user interface for presenting performance data associated with a patient is shown as a user interface 2021. The user interface 2021 may be configured to present video of the patient conducting a task or activity (e.g., tai chi) with kinematic analysis as discussed herein. The video may be provided to the clinician after being previously recorded by the patient. Additionally or alternatively, the video may be provided to the clinician concurrently with the patient performance of the activity (e.g., streaming the video content during a virtual clinic/remote programming session). If deemed appropriate (e.g., by the clinician viewing the video of the patient or an AI/ML process), new or adjusted stimulation therapy settings may be provided for control the patient's neurostimulation system, in step 2008.

In FIG. 22, through a wearable device 2200 (e.g. a wearable watch), bio-signals such as heart rate, sleep quality, time standing, heart rate variability, flights of stairs climbed, distance of walking and running, count of step, location information using GPS, and posture information using accelerometer and gyroscope are measured for use in AI/ML processing to control neurostimulation according to some embodiments. The biosignal data will be collected and processed to generate or estimate a "pain score" indicative of the level of pain of the patient. The data may be collected and processed using one or more device management systems (for example, one or more of the system discussed herein). The data is collected for multiple users, aggregated, and processed to build a model correlating biosignal data to pain scores for patients. Traditionally, clinicians often request patients to rank their pain from 0 to 10 where 0 represents no pain and 10 represents the highest level of pain that the patient may contemplate. In some embodiments, the pain score model reflects this traditional scale to represent patient pain levels.

In FIG. 23, by combining various data measured in a wearable device, the pain level is estimated according to process 2300. First, data is collected with healthy people wearing a wearable device. For the data of healthy people, a significant amount can be collected because unsupervised learning that does not need label information is applied. In the step, autoencoder is used for feature extraction. Then, the weights go to the next step and it is used as the initial weights in the model of step 2. It gives prior knowledge to the machine. In the step 2, supervised learning is applied with the input data of a first set of clinical data of the patients of chronic pain in the one or more countries or localities. The trained weights go to the step 3 and is used as initial weights in the model of step 3. In step 3, by using the data measured using the wearable device with the patients with chronic pain living in another country or locality is used as the input and the pain level that they reported as label information, supervised learning is used.

Upon use of the AI/ML process to correlate biosignals to pain levels of patients through supervised learning, the patient activity/pain model may be provided in a neurostimulation system such as the systems described herein. In FIG. 24, system 2400 includes an implantable pulse generator for providing a neurostimulation system for the patient. System 2400 includes a wearable device (e.g., a watch device) that generates biosignal data for the patient on an on-going basis. The current biosignal data of the patient is processed by a suitable system component (e.g., the wearable device, a patient controller device, a remote server, and/or the like) to generate an estimated pain level of the patient based on the captured biosignal data. Based on the estimated patient pain level, the neurostimulation system modifies its operations by changing one or more therapy parameters to optimize the patient's neurostimulation therapy (when appropriate).

In some embodiments, patient data obtained system device 2200 (see FIG. 22) and/or other sensors described herein for AI/ML processing or other processing may exhibit periods of time with missing data. For example, a patient having device 2200 may decide to forgo wearing device 220 over certain periods of time, may turn off certain sensors, or otherwise experience circumstances where measurement of user activity is not possible or is possibly inaccurate. In some embodiments, for the missing data of the relevant signals, the missing data may be estimated using an optimal interpolation method. From the interpolated signals, the pain levels of a population of the patients are estimated using a machine learning algorithm (e.g., using one or more of the patient management systems described herein). Finally, using the estimated interpolation signals, the pain level of specific patients are estimated to control neurostimulation and/or manage therapy for the patients.

Severe injuries of lower extremities often lead to chronic pain and reduced walking abilities. Chronic pain has a negative impact on a patient's overall health. In some embodiments, gait analysis is conducted as an in-depth biomechanical assessment. In some embodiments, gait analysis confirms perception of pain and function and can be used for pain measurement to control operations of a neurostimulation system.

In some embodiments, spinal cord stimulation (SCS) or dorsal root ganglion (DRG) stimulation can help manage chronic pain when the cause cannot be removed, or the injury cannot be repaired. Using neurostimulation for chronic pain patient would help pain relief and therefore changes in gait that could be monitored over time.

In some embodiments, an IPG or neurostimulation system contains sensors for gait analysis with the ability of training a ML algorithm for reinforcement learning. The reinforcement learning will be particularly used to select the best programming setting for bringing patient to the state that has no or reduced pain.

FIG. 40 depicts system 4000 for providing a neurostimulation therapy to a patient. In some embodiments, neurostimulation system 4000 provides electrical stimulation for application to the spinal cord and/or one or more dorsal root ganglia to treat pain of the patient. System 4000 includes implantable pulse (IPG) generator 40001 and one or more stimulation leads 4002. System 4000 may include one or more wearable devices 4004 (such as a smartwatch device) with, possibly, one or more patient apps. System 4000 may include patient controller device 4003 with, possibly, one or more patient apps. Patient controller device 4003 and wearable device(s) 4004 may communicate with digital health infrastructure 4005 as discussed herein.

The patient may interact with one or more apps on patient controller device 4003 and may enter a "pain score" as respective times. System 4000 may employ entered pain scores to perform machine learning training operations to automatically control neurostimulation therapy for the patient.

In some embodiment as discussed herein, a patient controller app on patient device 4003 and/or wearable device 4004 provides pain level measurement (NRS) features which enable patient to enter the pain level every time he/she wants to change programming setting. The historical programming and pain info along with gait measurements over time are used to train a ML model for the neurostimulation system or IPG which learns over time through reinforcement learning. Specifically, the neurostimulation system 4000 or IPG 4001 with added gait component and ML capability is tuned over time according to some embodiments. The machine learning may be performed, in some embodiments, using executable instructions on one or more of IPG 4001, patient device 4003, wearable device 4004, and digital health infrastructure 4005. Any of the machine learning algorithms discussed in this application, generally known, or later developed may be employed according to some embodiments.

In some embodiments, the neurostimulation system 4000 or IPG 4001 will collect gait data from the SCS patient after SCS implant and analyze the gait data. In some embodiments, accelerometers may be included in the IPG 4001 or a patient device (such as wearable device 4004) to measure patient movement. The data from the one or more accelerometers is subjected to analysis to determine gait specific features 4006. The gait features such as Step Length, Stride length, Stance Phase, Swing phase, Single support, Total double support, Load response, Pre-swing, Step time, Gait cycle, Cadence, Speed[m/s] and average speed may be analyzed real time and be used toward predicting the programming setting and pain level of the patient.

In some embodiments, the patient enters the patient's current pain level on the patient controller application on one or more of devices 4003 and 4004 whenever the patient feels pain and desires a change of the programming setting(s). The pain and gait analysis along with the programming data are used for training a neural network model 4007. Model 4007 is trained for few days after patient has done the implant surgery and then the reinforcement learning algorithm is used to check the gait state of the patient and change the patient programing data to lower the pain and bring patient back to the no or reduced pain state. Model 4007 for a specific patient may be stored in the patient's IPG 4001, patient device 4003, wearable device 4004, or digital infrastructure 4005. One or more of these devices may provide current patient gait features through model 4006 to obtain stimulation parameters and/or patterns appropriate for the patient and provide such parameters to IPG 4001 for provision of the therapy to the patient.

FIG. 41 depicts operations for controlling a neurostimulation system according to some embodiments. In 4001, movement data is obtained from sensors of one or more patient devices. In 4002, movement data is processed to extract gait specific features. In 4003, variation of stimulation therapy is conducted (pulse parameters, pulse pattern, etc.). In 4004, ML training operations are performed to develop model between gait features and appropriate neurostimulation therapy parameters/patterns. In 4005, the ongoing neurostimulation therapy is controlled based on ongoing sensing/detection of gait features after the gait/therapy model for the patient is developed. In 4006, refinement of the ML gait/therapy model is continued between gait features or appropriate neurostimulation therapy.

In other embodiments, any additional sensor or patient data may be incorporated into the ML model along with gait features including any of the sensor data and patient data discussed herein.

In some embodiments, AI/ML processing is applied to EEG data to determine patient states to control neurostimulation. For example, EEG signals are measured in resting state for 5 minutes. In the resting state, the subjects sit upright in a comfortable chair with their eyes closed. Cortical activity is estimated using source localization method from the measured EEG signals. The cortical activity is estimated in 5 frequency bands of low theta (2-5 Hz), high theta (5-9 Hz), alpha (9-13 Hz), beta (13-30 Hz), and gamma (30-42 Hz) according to some embodiments. Any suitable source localization processing may be applied such as those disclosed in the following article: A systematic review of EEG source localization techniques and their applications on diagnosis of brain abnormalities, Journal of Neuroscience Methods, Volume 339, 1 Jun. 2020, 108740, by Shiva, Asadzadeha et al., which is incorporated herein by reference. After completion of the source localization computations, a set of data is created which represents the level of neural activity within each frequency band at different cortical locations. Each "vertex" of data in the set of source localization data represents the neural activity level at a defined cortical location within a defined frequency band.

Based on the AI/ML processing of the cortical activity, a suitable patient model is created and it is possible to determine how each pain patient is different from healthy control group in the pattern of the cortical activity. By determining differences between the EEG signals of a specific pain patient and the model of healthy controls, neurostimulation may be applied to adjust the pain patient's EEG signals of the pain patient towards the model of health controls.

FIG. 25 depicts EEG signal processing 2500 according to some representative embodiments. EEG signals are obtained for a set of patients including pain patients and healthy controls. Source localization is applied to the EEG signals. The source localization also analyzes the cortical activity at respective frequencies bands. The frequency bands (e.g., low theta, high theta, alpha, beta, and gamma) are employed to create multiple models (e.g., five models) to classify patients as healthy control subjects or patient subjects. Suitable machine learning processing is applied in this process. The machine learning may include application of random forest machine learning modeling. In accordance with some embodiments, machine learning model uses the cortical activity of healthy people and patient's group as the input. Based on the input of the cortical activity of each patient, it classifies whether the input is control or patient group. For 5 frequency bands, one model is generated and finally 5 machine learning models are used.

During initial processing of the EEG data from patients and health controls, suitable machine leaning processing (such as Random Forest processing) may be employed to determine feature importance. That is, within each frequency band, the localization data may be processed to determine the relevant differences between cortical activity for patients and cortical activity for healthy controls. After determining feature importance, the identified features may be used for classification activities to determine whether a given patient is experience pain or is in a "healthy" non-pain state.

In some embodiments, one or more features within the EEG localization data for each frequency band that exhibits the largest "importance" weight(s) are selected. For example, for the low theta band, ML/AI processing of EEG data by Applicant has identified insular cortex localized EEG data as having an "important" weight within that frequency band. Similarly, dorsolateral prefrontal cortex (DLPFC) localized EEG data was identified for the high theta band; medial prefrontal cortex localized EEG data was identified for the alpha band; medial prefrontal cortex localized EEG data and anterior cingulate cortex localized EEG data were selected for the beta band; and medial prefrontal cortex localized EEG data was identified for the gamma band.

The selected features for the respective frequency bands are used to generate a classification model as shown in model 2600 in FIG. 26. Classification model 2600 uses ML/AI processing to classify between pain patients (e.g., pain experiencing chronic pain such as neuropathic pain) and health controls (e.g., pains in a healthy, non-pain state). Classification model 2600 combines the features identified as important features in prior ML/AI processing as described herein. By combining the cortical activity features from the 5 frequency bands as one input layer, data for the cortical activity features may be used as the input of the machine learning algorithm. In this case, sufficiently abundant information is provided to the machine learning model to automatically select only useful information in classification.

In some embodiments, 10 vertexes (spatial locations in the EEG) data are identified (from the frequency band analysis discussed herein) which show the largest differences between the EEG localization, frequency band data for health controls and pain patients. Then, using only the cortical activity data on the selected 10 vertexes for the respective frequency bands, a new classifier is defined for classification of the state of a patient to control a neurostimulation therapy for the patient. In some embodiments, each vertex represents the cortical activity within one of the frequency bands for a cortical location from the EEG localization processing identified as showing one of the largest differences between heathy controls and pain patients (e.g., as determined using the random forest ML/AI processing discussed herein). A healthy control population profile or model may be defined using prior EEG location analysis of EEG data from a population of health controls. This profile or model may represent the statistical average, median, or other suitable representation of the EEG localization data for the frequency band for each selected vertex. A corresponding patient EEG localization data for the respective vertices within the representative frequency bands are then compared against this healthy control profile or model. A "distance" measure or metric may be calculated between the current state of the patient (as represented from the most recent EEG data) and the health control profile or model. The distance may be used to classify the current state of the patient (e.g., whether the patient is experiencing pain or is in a pain free or a low or lower pain state).

FIG. 27 depicts system 2700 which employs EEG localization data to optimize neurostimulation programming and/ or determine the correct placement of one or more stimulation leads. System 2700 includes EEG electrodes 2701 to measure EEG signals from the patient. The EEG signals are processed by EEG processing system 2705. EEG electrodes 2701 and EEG processing system 2705 may be implemented using commercially available products as is well known. EEG processing system 2705 performs EEG localization. During operation of system 2700, controller/programmer device 2702 communicates with EEG processing system 2705 to obtain the EEG localization data. Device 2702 performs AI/ML classification of the patient state using the EEG localization data according to some embodiments. Based on the classification, controller/programmer deice 2702 alters the neurostimulation parameters to control the operations of IPG 2703 (or the clinician may alter the implant position of the electrodes). The variation in parameters changes the pattern of pulses applied to the patient via electrodes of one or more stimulation leads 2704. One or more of the stimulation parameters may be varied including pulse amplitude, pulse width, pulse frequency, burst frequency, noise profile, electrode polarities, etc. In some embodiments, different pulse patterns are applied such as tonic stimulation, burst stimulation, high frequency stimulation, multi-frequency stimulation, and/or the like. As parameters and/or patterns are varied, the AI/ML classification of the patient is repeated to determine whether the change in the neurostimulation therapy causes the patient to be "closer" to a "healthy" state (e.g., without pain). When stimulation parameters are identified where the patient's EEG data more closely matches the EEG data of a healthy control population, the variation of the parameters may cease and the stimulation therapy may be considered optimized. Although control of neurostimulation is described using operations of device 2702, control of neurostimulation may be implemented in other locations such as IPG 2701 or elsewhere according to other embodiments.

FIG. 28 depicts graph 2800 of features of two populations groups to control neurostimulation therapy according to some embodiments. Graph 2800 includes points representing features of population 2801 which corresponds to patients having a neurological disorder such as chronic pain or a movement disorder. Graph 2800 includes points representing features of population 2802 which corresponds to healthy controls. In FIG. 28, the graph is necessarily two dimensional for presentation to a user via a computer/ smartphone/table user interface and, accordingly, the dimensionality of the graph has been reduced for the purposes of presentation. However, a multi-dimensional representation of patients and health controls could be constructed to maintain integrity of the population data. In some embodiments, the features include features from EEG data or EEG localization data as discussed herein. The multi-dimensional data may alternatively or additionally include image data using a camera, and the time series data of ECG, accelerometer, and/or gyroscope sensors, etc. The multi-dimensional data may alternatively or additionally include any of the data discussed herein including any suitable physiological data such as heart rate or cardiac activity data, blood pressure, respiration data, blood glucose data, and/or the like. Any of to the patient related data discussed herein may be used according to some embodiments for a multi-dimensional representation of patient(s) and/or graphs of populations.

In high dimension modeling of populations, it is possible to classify the healthy control and patient group with a high degree of accuracy. First, the center position (Pc) of healthy control group is found by calculating the average of each point for all dimensions of the multi-dimensional representative of each member of the population. Then, minimizing the distance between the center position Pc and the position of a respective patient is the goal of the neurostimulation therapy optimization process using the multi-dimensional representation of the respective patient. The distance between the position of a respective patient (Pp) and the center position of control group (Pc) is calculated by the norm between the two points as: $d(Pc, Pp)=\|Pc-Pp\|$.

In some embodiments, neurostimulation is controlled by minimizing the distance between the measured features of a patient and the center position of control group using the norm calculation discussed herein. Although the norm calculation provides a useful metric for control of neurostimulation, other relevant classification techniques may be applied including boundary condition classification techniques for patient and health control populations as examples.

FIG. 29 depicts system 2900 that controls neurostimulation using multi-dimensional data according to some embodiments. As shown in FIG. 29, system identification using neurostimulation (e.g., spinal cord stimulation, dorsal root ganglion stimulation, peripheral nerve stimulation, deep brain stimulation, cortical stimulation, etc.) as the input and the distance between the center position of healthy control group and the position of each patient as the output.

In order to implement a controller, first system identification is performed to find the matrix A, B, C, D in the state-space equation. While changing the amplitude, frequency, and pulse with of the stimulation signal of the neurostimulation system from minimum to maximum value, we measure the distance between the position of each patient (Pp) and the center position of healthy control group (Pc) in the high dimensional feature space. Using the input and output signals, system identification is conducted. To perform system identification, the Eigensystem realization algorithm (ERA) may be applied.

FIG. 30 depicts block diagram 2900 of a controller implementation according to some embodiments. The state update equation between the distance between Pc and Pp and input of spinal cord is defined by this equation. There is system disturbance in the system and at measurement, the distance between the center position of healthy control group (Pc) and position of each patient (Pp) is measured. At this point, measurement noise is added. From the noise added measurement signal, the true distance d is estimated using a Kalman filter. Then, the LQR controller multiplies the optimal gain −K to the estimated distance d and it generates the optimal spinal cord stimulation to reach the distance d to the desired value.

A controller for neurostimulation may be implemented in a number of system locations for any of the embodiments discussed herein. For example, a processor or suitable circuit may implement the operations of a suitable controller (using software instructions and/or embedded circuit logic) and the processor or suitable circuit may be included within an implantable pulse generator, a patient controller device, a clinician programmer device, a wearable electronic device, a remote health digital platform/server, or any other suitable computing system.

FIG. 31 shows example simulation 3100 as the controller attempts to reduce the distance between Pc and Pp. At time 100 (0.2 s), the controller begins and approximately 50 samples (0.1 s) are conducted to make the output of the controller (distance between Pc and Pp) to reach the goal value (namely, d=0). After 0.1 s, the output signal of the controller reaches the goal value d=0. In FIG. 31, neurostimulation parameters represents the input value that we give to the neurostimulation system. When the values are applied to the neurostimulation system, the controller controls the output to move measurement of the patient's multi-dimensional feature space to the center of the healthy control feature space.

In some embodiments, a patient's neurological disorder may prevent the patient from being brought completely within the feature space of healthy control population. In such cases, it may be appropriate to utilize similar control operations as discussed herein while allowing for less range in modification of the patient's measured features to control neurostimulation. In some embodiments, as shown in graph 3200 of FIG. 32, by collecting the data of control group, the center position, Pc is calculated as discussed herein. Also, when the patient feels weakest pain, the feature location Pl is identified, and when feeling the strongest pain, the feature location Ph is identified. Each of feature location may be a multi-dimensional vector with each constitute element of the vector representing the quantity of a measured patient physiological or other suitable feature. The distance between the center position Pc of healthy control group and the position Pl of weakest pain level of the patient is defined dl, and dh is defined as the distance between the position of Ph of strongest pain level of the patient and the center position Pc. While changing the pain level of individual chronic pain patient, it has the value between dl and dh. Between the two values, it have continuous values, and it is used as sensor value for the closed-loop control system.

FIG. 32 shows the block diagram of closed-loop control system 3200 to control the pain level of chronic pain patients proposed in this invention. Here, the system is the body of the patient, and the controller is implemented within a neurostimulation system including an implantable pulse generator (IPG). The sensor may represent EEG components, camera (video data), and wearable sensing components (accelerometer, gyroscope, and EKG, etc.), and/or the like, the feature of the data is located in the feature space. The distance dv is calculated using the center position Pc of the healthy control group and the position Pv of individual patient which changes based on the pain level, and the reference is the value to make dv equals 0. While repeating the closed-loop, the position Pv becomes close to the center position Pc of the health control group.

In some embodiments, EEG data may be combined with evoked compound action potential (ECAP) data to optimize neurostimulation according to some embodiments. Electrically evoked compound action potentials represent the synchronous firing of a population of electrically stimulated nerve fibers. Measurement of ECAPs has been utilized as a means of directly assessing the level of fiber recruitment in the dorsal columns of the spinal cord for neurostimulation. ECAP sensing may also be applied for other neural targets in a similar manner. ECAPs are signals elicited by electrical stimulation and recorded near a bundle of fibers. In particular, ECAPs usually arrive less than one millisecond (<1 ms) after a corresponding stimulation pulse and last in the range of approximately one half to one millisecond (0.5-1 ms). ECAPs may be measured and analyzed, for example, to evaluate and/or control the comfort and/or efficacy of a SCS treatment regimen (see e.g., US patent publication numbers 2020/0282208 A1 entitled "Neural Stimulation Dosing"; 2011/018448 A1 entitled "Spinal Cord Stimulation to Treat Pain"; and 2020/0391031 A1 entitled "System and Method to Managing Stimulation of Select A-Beta Fiber Components"; the disclosures of which are incorporated herein by reference).

In some embodiments, a process of extracting the information of pain and tingling from EEG signals ($d_{pain}$ includes pain data as a measure relative to the center of the healthy control population for pain, and $d_{sensation}$ includes sensation data as a measure relative to the center of the healthy control population for paresthesia (tingling) inducing stimulation) is performed. Also, by combining EEG data from two different types of patient states, the combined data set is used as the final EEG feature data to control neurostimulation. In an initial EEG analysis of a population of healthy control, from the EEG signals of healthy control and patient's group, the features of each group are defined in the feature space following the discussion herein (where using multi-dimensional representation of patient EEG location data within relevant frequency bands): $P_c$ is the center position of healthy control group, and $P_p$ represents the feature position of individual pain patient and $d_{pain}$ is the distance between the two points. Further, the EEG signals of resting state and the EEG signals are measured while inducing tingling (paresthesia) sensation to the subjects using electrical stimulation from an a neurostimulation system (e.g., an implanted device or external trial stimulator). For both cases, healthy control group participate as the subjects; $d_{rest}$ is the distance between the position of the individual patient ($P_p$) and the center position of resting state data ($P_c$), and $d_{tingling}$ is defined as the distance between the center position of tingling data ($P_t$) and the position of the individual patient ($P_p$). The ratio of the two distance is defined as $d_{sensation}$:

By calculating the average point of healthy control group (represented as $P_c$). The feature position of an individual pain patient is defined as $P_p$. The distance between $P_c$ and $P_p$ is defined as $d_{pain}$. For both cases, healthy control group participate as the subjects. The center position of resting state data is defined as $P_r$, and $P_t$ is defined as the center position of tingling sensation data. When we set the feature position of individual pain patient as $P_p$, the distance between $P_r$ and $P_p$ is defined as $d_{rest}$ and the distance between $P_p$ and $P_t$ is defined as $d_{tingling}$.

Using the two distances, we can calculate $d_{sensation}$:

$$d_{sensation} = d_{tingling}/d_{rest}$$

From this analysis, $d_{pain}$ is obtained and it is possible to get $d_{sensation}$. $d_{EEG}$ is defined as the combination of the two distances:

$$d_{EEG} = d_{pain} + d_{sensation}$$

FIG. 34 depicts processing 3400 of ECAP data to be combined with EEG data to define a stimulation therapy for a patient. As shown in FIG. 34, a stimulation waveform is provided to the patient and ECAP data is measured for the ECAPs generated by the applied stimulation. From the measured ECAP signal, the mean value of the signal is subtracted from it. Then, we take the absolute value of the signal. The sum of the absolute value of the ECAP signal is defined as ECAP area (AECAP).

The ECAP information is defined in the following in equation:

58

$$I_{ECAP} = \frac{1}{A_{ECAP}}$$

In some embodiments, the ECAP information is combined with the EEG data as discussed herein to control neurostimulation. FIG. 35 depicts system 3500 for providing a neurostimulation therapy to a patient using an implantable pulse generator. System 3500 includes control of the neurostimulation therapy in response to sensing of EEG and ECAP data. System 3500 using $d_{total}$ which is the sum of $d_{EEG}$ and $I_{ECAP}$ as the sensor signal. Based on $d_{total}$ information, the SCS generator generates an optimal stim waveform to reduce the value of $d_{total}$. System 3500 may be implemented using similar components as previously discussed herein and by sensing and processing the patient data as discussed in FIG. 34 (as an example) to optimize the patient's neurostimulation therapy.

In some embodiments, $d_{EEG}$ is defined as the sum of $d_{pain}$ and $d_{sensation}$, and $I_{ECAP}$ is obtained from ECAP signal, and a closed-loop system is implemented using $d_{total}$ information as the sensor signal. By measuring the value of $d_{EEG}$ from EEG signals and $I_{ECAP}$ from ECAP signal as the sensor signal, the closed-loop system repeats the loop to attempt to drive the value of $d_{total}$ as close to 0 as possible or practical. Then, the IPG generates an optimal stim waveform automatically to converge the value of $d_{total}$ as 0.

Whenever the pain level of a patient is changed, by measuring EEG data and ECAP signal again, an update may be applied to the stimulation waveform. By repeating this process, generation of optimal waveforms reflecting the body condition of the patient which changes every day may occur.

In some embodiment, weighting factors may be applied to the patient condition metric as follows:

$$d_{total} = a \times d_{pain} + b \times d_{sensation} + c \times I_{ECAP}$$

Other factors may be included within this patient condition metric. For example, another factor may be included for patient feature(s) for other sensors.

The patient condition metrics or biomarker may be used to converge to optimal therapies using a number of techniques. For example, the eigenvalue system characterization approach (as discussed herein) by be employed to select stimulation parameters and/or stimulation pattern. Alternatively, a systematic sweep of stimulation parameters and/or stimulation patterns may be applied automatically while measuring the patient response in the calculated patient condition metric and/or biomarker. The optimal parameter(s) and/or pattern may be selected based on the combination that most closely causes the patient response to approach the model/representation of the healthy control population.

In some embodiments, stimulation parameters and/or patterns are varied in a manner that depends upon the calculated difference between the distance from the patient's response to the representation or model of the healthy population for respective parameters and/or patterns. For example, the process may begin by setting all of the parameters to the mean value. It is defined as u0, and u0 is used as the parameters of the neurostimulation therapy which is used the input of the system. After applying stimulation with the mean stimulation parameters, the initial patient distance d, (defined as d0) is calculated between the patient feature vector and the health control population vector (model/representation). Then, after fixing a subset of parameters (parameters of frequency and pulse width) to the mean value, the process uses the maximum value of the amplitude and calculates the resulting distance d (defined as dmax) for the patient. After setting the value of the amplitude to the minimum value, the process calculates the distance d (defined as dmin). If the difference between dmax and d0 is 5 and that of between dmin and d0 is 2, the interval between dmax and d0 has more information for system identification. Therefore, with the mean value between the maximum and mean of the amplitude, we investigate the distance d. By identifying parameter region(s) that exhibit greater differences, the systematic analysis of stimulation parameters to converge to optimal parameters may occur in a more efficient manner according to some embodiments.

Although some embodiments that employ multi-dimensional analysis of patient features and measuring a distance from current patient features to multi-dimensional features obtained from a health population for pain, other embodiments may employ similar analysis for different neurological disorders. For example, multi-dimensional feature analysis may be conducted for patients with movement disorders, sleep disorders, epilepsy, and/or any other relevant neurological disorder.

FIG. 36 depicts system 3600 for treating sleep disorders according to some representative embodiments. System 3600 include one or more sensors (on one or more DBS leads and/or cortical leads) to observe the patient's natural sleep brain waves and system 3600 compares the sensed patient features to a model or representation of the healthy control. The brain waves of the patient having system 3600 are then analyzed for possible disorders. If there is a possible disorder, system 3600 applies neurostimulation consistent with characteristics consistent with neurological activity for a healthy population. For instance, if the frequency of a healthy k-complex is once every 1-1.3 minutes and the patient has a frequency of once every 0.9 minutes, system 3600 would stretch the theta wave sample to be within the 1-1.3 minute range while avoiding stimulation that would induce possible seizure activity. Another possible application for system 3600 would be inducing stage two sleep in chronic insomniacs after detecting (using one or more sensor(s)) stage 1 sleep for over 5 minutes by emitting neurostimulation with waveform characteristics that correspond to previously recorded healthy theta waves.

In FIG. 36, system 3600 controls neurostimulation using multi-input multi-output (MIMO) system control. The parameters (e.g., pulse frequency, pulse amplitude, pulse width, electrode polarities, etc.) represent the inputs to the MIMO control system and the outputs are represented by the waveform characteristics that correspond to health neurological sleep activity (e.g., sleep spindles, K-complexes, delta wave components, theta wave components, alpha wave components, and beta wave components).

In some embodiments, the patient is in awake, while giving the minimum and maximum value of the parameters of amplitude, frequency, and pulse width of deep brain stimulation, system 3600 measures the output signals of sleep spindles, k-complexes, delta wave component, theta wave component, alpha wave component, and beta wave components. Using the input and output signals, system 3600 conducts system identification (of the patient's physiological response to stimulation). System 3600 calculates the A, B, C, D matrix of the state space equation through system identification operations. In some embodiments, system 3600 used the eigensystem realization algorithm (ERA) method.

FIG. 37 depicts block diagram 3700 for implementation of system 3600. The state space equation of the output, i.e., sleep spindles, K-complexes, delta wave, theta wave, alpha wave, beta wave and the input of spinal cord is defined by the patient state equation in diagram 3700. At measurement, sleep spindles, K-complexes, delta wave, theta wave, alpha wave, beta wave are measured. At this point, measurement noise is added by the neurostimulation system. From the noise added measurement signal, the true sleep spindles, true K-complexes, true delta wave, true theta wave, true alpha wave, true beta wave are estimated using a Kalman filter. Then, the LQR controller multiplies the optimal gain –K to the estimated sleep spindle, K-complexes, delta wave, theta wave, alpha wave, beta wave and it generates the optimal deep brain stimulation to reach each output value to the desired value to control sleep stages.

Based on the calculation of the optimal gain parameters and system identification parameters, system 3600 may employ neurostimulation to correspond to waveform characteristics of table 3800 in FIG. 38. That is, when system 3600 detects neurological activity associated with a sleep disorder, system 3600 may generate electrical stimulation with characteristics corresponding to the profiles shown in table 3800 for the respective sleep stages. In some embodiments, each sleep stage stimulation generated by the LQR controller is controlled by controlling the ratio of power spectral density for sleep spindles, K-complexes, and each frequency band using deep brain stimulation signal. The control of sleep stages may be continued by monitoring sleep activity in a closed-loop manner by system 3600.

As discussed herein, neurostimulation systems may include multi-dimensional analysis of patient features in a closed loop system to control neurostimulation for a patient. In other embodiments, multi-dimensional analysis may be employed to assist clinician programming of a neurostimulation therapy for a patient. For example, during a remote programming session, the user interface of the clinician may display a graph that represents the multi-dimensional physiological of the patient during a remote programming session relative to a population of health controls and/or a population of other patients with the same or a similar neurological disorder. For example, the clinician programmer app on the clinician's device 130 may display (during remote or in person programming) graph 2800 (as one example). Graph 2800 projects the multi-dimensional measurement of the patient features and population features into two dimensions to accommodate display on a user device. The current patient may be shown in graph 2800. Also, the path in the change of the patient's "position" during programming may be displayed to assist the clinician. The clinician may observe improvement in the patient's response to changes in parameters of the neurostimulation therapy as the patient's "position" moves through the feature space toward the feature space associated with the health population portion of the graph.

FIG. 39 depicts operations for assisting programming of a neurostimulation therapy according to some embodiments. In 3901, a programming session is initiated (either a remote programming session as described herein or an in-person programming session). In 3902, neurostimulation is applied to the patient at suitable parameters. In 3903, patient features are measured using one or more sensors. For example, sensors integrated with the patient's implanted system, sensors of device 2200, EEG sensors, and/or the like may be employed to measure patient physiological condition. In 3904, a multi-dimensional representation of the state of the patient is constructed using the data from the one or more sensors. Suitable processing may occur on the sensor data for the multi-dimensional representation such as frequency band analysis, feature extraction, and/or the like. The projection of the multi-dimensional representation occurs into two-dimensional space is calculated in 3905. The projection may also occur according to clinician preferences. For example, the clinician may select certain features to be grouped for the "X" axis and the remaining features to be grouped for the "Y" axis. Also, the projection of population state representations may be calculated similarly.

In 3906, the patient's current "position" within the two-dimensional space is displayed relative to the projection of population representations into the same two-dimensional space. Optionally, the path of the patient through the space over time as a result of prior programming steps may be displayed (3907) as the iterations of the programming process occurs. In 3908, the distance between the patient's current position and the center position of the healthy population is calculated and displayed (optionally). In 3909, neurostimulation parameters are modified. The clinician may modify the parameters according to the clinician's judgment. Alternatively, automated changes may be applied using any suitable automated programming methodology (including methods and operations described herein). The process returns to 3902 to apply neurostimulation according to the modified parameters and additional iterations of the process may be performed if deemed appropriate by the clinician.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

The invention claimed is:

1. A method of providing a neurostimulation therapy to a patient, comprising:

applying electrical pulses to a neural target of a patient according to a plurality of stimulation parameters;

obtaining movement data from one or more sensors implanted in or worn by the patient while electrical pulses are applied to the patient;

processing the movement data to extract a plurality of gait features corresponding to characteristics of the patient's gait while electrical pulses are applied to the patient;

obtaining patient reported pain levels from the patient using one or more patient applications on a patient therapy controller device corresponding to time intervals in which the electrical pulses are applied to the patient;

training a machine learning (ML) model using the plurality of stimulation parameters, the plurality of gait features, and the patient reported pain levels;

after training the ML model, controlling application of electrical pulses to the patient to treat pain of the patient in accordance with extracted gait features of the patient;

determining a sensor-driven score associated with the patient;

determining an evaluator-driven score associated with the patient based on patient reported outcomes;

determining a rigidity score associated with the patient based on the sensor-driven score and the evaluator-driven score;

modifying the plurality of stimulation parameters based on the rigidity score; and applying electrical pulses to the neural target of the patient according to the modified plurality of stimulation parameters.

2. The method of claim 1, wherein the neurostimulation therapy is selected from the list consisting of: spinal cord stimulation and dorsal root ganglion stimulation.

3. The method of claim 1, wherein movement data is obtained by one or more sensors of a wearable device of the patient.

4. The method of claim 1, wherein movement data is obtained by one or more sensors of an implantable pulse generator (IPG) of the patient.

5. The method of claim 1, wherein the training is performed by one or more software applications executed on the patient therapy controller device.

6. The method of claim 1, wherein the training is performed by one or software applications executed by one or more processors of an implantable pulse generator (IPG) of the patient.

7. The method of claim 1, wherein the training is performed by one or software applications executed by one or more processors of a server platform of a medical device management system.

8. The method of claim 1, wherein one or more features associated with the training include at least one feature selected from the list consisting of: step length, stride length, stance phase, swing phase, single support, total double support, load response, pre-swing, step time, gait cycle, cadence, and speed.

9. The method of claim 1, wherein:

the sensor-driven score is determined based on the movement data from the one or more sensors implanted in or worn by the patient;

the evaluator-driven score is determined based on the patient reported outcomes and an assessment performed by a clinician, the patient reported outcomes including the patient reported pain levels, patient reported well-being scores, and patient reported activity levels; and the rigidity score represents a quantified measure of involuntary muscle tone or resistance to movement in one or more regions of the patient's body.

10. The method of claim 1, further comprising:

obtaining the patient reported outcomes from the patient using the one or more patient applications on the patient therapy controller device, the patient reported outcomes including the patient reported pain levels, patient reported well-being scores, and patient reported activity levels, wherein the training the ML model includes training the ML model using the plurality of stimulation parameters, the plurality of gait features, and the patient reported outcomes.

* * * * *